US007495092B2

(12) United States Patent
Barrangou et al.

(10) Patent No.: US 7,495,092 B2
(45) Date of Patent: Feb. 24, 2009

(54) COMPOSITIONS COMPRISING PROMOTER SEQUENCES AND METHODS OF USE

(75) Inventors: Rodolphe Barrangou, Madison, WI (US); Andrea Azcarate-Peril, Raleigh, NC (US); Eric Altermann, Apex, NC (US); Tri Duong, Raleigh, NC (US); Todd R. Klaenhammer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/330,471

(22) Filed: Jan. 12, 2006

(65) Prior Publication Data

US 2006/0166323 A1 Jul. 27, 2006

Related U.S. Application Data

(60) Provisional application No. 60/644,189, filed on Jan. 14, 2005.

(51) Int. Cl.
*C07H 21/04* (2006.01)
*C12N 15/00* (2006.01)
*C12N 15/74* (2006.01)
*C12N 1/00* (2006.01)
*C12N 1/20* (2006.01)
*C12N 1/21* (2006.01)

(52) U.S. Cl. .................. 536/24.1; 435/320.1; 435/471; 435/243; 435/252.1; 435/252.9

(58) Field of Classification Search ....................... None
See application file for complete search history.

(56) References Cited

U.S. PATENT DOCUMENTS

| | | | |
|---|---|---|---|
| 5,837,509 A | 11/1998 | Israelsen et al. | |
| 6,451,584 B2 | 9/2002 | Tomita et al. | |
| 6,476,209 B1 | 11/2002 | Glenn et al. | |
| 6,544,772 B1 | 4/2003 | Glenn et al. | |
| 6,635,460 B1 | 10/2003 | Van Hijum et al. | |
| 2002/0159976 A1 | 10/2002 | Glenn et al. | |
| 2003/0138822 A1 | 7/2003 | Glenn et al. | |
| 2004/0009490 A1 | 1/2004 | Glenn et al. | |
| 2004/0208863 A1 | 10/2004 | Versalovic et al. | |
| 2005/0003510 A1 | 1/2005 | Chang et al. | |
| 2005/0112612 A1 | 5/2005 | Klaenhammer et al. | |
| 2005/0123941 A1 | 6/2005 | Klaenhammer et al. | |
| 2006/0166323 A1* | 7/2006 | Barrangou et al. | 435/69.1 |

FOREIGN PATENT DOCUMENTS

| | | |
|---|---|---|
| EP | 0 888 118 B1 | 1/1999 |
| WO | WO 02/12506 A1 | 2/2002 |
| WO | WO 02/074798 A2 | 9/2002 |
| WO | WO 03/084989 A2 | 10/2003 |
| WO | WO 2004/031389 A1 | 4/2004 |
| WO | WO 2004/020467 A2 | 5/2004 |
| WO | WO 2004/069178 A2 | 8/2004 |
| WO | WO 2004/096992 A2 | 11/2004 |
| WO | WO 2005/001057 A2 | 1/2005 |
| WO | WO 2005/012491 A2 | 2/2005 |
| WO | WO 2005-001057 A2 | 6/2005 |

OTHER PUBLICATIONS

Altermann, E., et al., "Complete Genome Sequence of the Probiotic Lactic Acid Bacterium *Lactobacillus acidophilus* NCFM," *PNAS*, 2005, pp. 3906-3912, vol. 102 (11).
Arsenijevic, S., and L. Topisirovic, "Molecular Analysis of Mutated *Lactobacillus acidophilus* Promoter-Like Sequence P15," *Can. J. Microbiol.*, 2000, pp. 938-945, vol. 46.
Barrangou, R., et al., "Functional and Comparative Genomic Analyses of an Operon Involved in Fructooligosaccharide Utilization by *Lactobacillus acidophilus*," *PNAS*, 2003, pp. 8957-8962, vol. 100 (15).
Kullen, M. J., and T. R. Klaenhammer, "Identification of the pH-Inducible, Proton-Translocating $F_1F_0$-ATPase (*atpBEFHAGDC*) Operon of *Lactobacillus acidophilus* by Differential Display: Gene Structure, Cloning and Characterization," *Molecular Microbiology*, 1999, pp. 1152-1161, vol. 33 (6).
McCracken, A., et al., "Analysis of Promoter Sequences from *Lactobacillus* and *Lactococcus* and their activity in several *Lactobacillus* Species," *Arch Microbiol*, 2000, pp. 383-389, vol. 173.
Abee, et al., "Kinetic Studies of the Action of Lactacin F, A Bacteriocin Produced by *Lactobacillus johnsonii* that Forms Poration Complexes in the Cytoplasmic Membrane," *Appl. Environ. Microbiol.*, 1994, pp. 1006-10013, vol. 60.
Allison and Klaenhammer, "Functional Analysis of the Gene Encoding Immunity to Lactacin F, *Lafi*, and its Use as a *Lactobacillus*-Specific, Food-Grade Genetic Marker," *Appl. Environ. Microbiol.*, 1996, pp. 4450-4460, vol. 62.
Allison and Klaenhammer, "Genetics of Bacteriocins Produced by Lactic Acid Bacteria and their Use in Novel Industrial Applications," *Manual of Industrial Microbiology and Biotechnology*, 1999, pp. 789-808, ASM Press, Washington, D.C.
Allison, et al., "Expansion of Bacteriocin Activity and Host Range Upon Complementation of Two Peptides Encoded with the Lactacin F Operon," *J. Bacteriol.*, 1994, pp. 2235-2241, vol. 176.
Altermann, et al., "Identification and phenotypic characterization of the cell-division protein CdpA," *Gene*, 2004, pp. 189-197, vol. 342.
Altermann, et al., "Complete Genome Sequence of the Probiotic Lactic Acid Bacterium *Lactobacillus acidophilus* NCFM" *Proc. Natl. Acad. Sci. U.S.A.*, 2005, Early Edition 10.1073/pnas. 0409188102, online publication date Jan. 25, 2005.
Azcarate-Peril, et al., "Identification and Inactivation of Genetic Loci Involved with *Lactobacillus acidophilus* Acid Tolerance," *Appl. Environ. Microbiol.*, 2004, pp. 5315-5322, vol. 70.
Barefoot and Klaenhammer, "Detection and Activity of Lactacin B, A Bacteriocin Produced by *Lactobacillus acidophilus*," *Appl. Environ. Microbiol.*, 1983, pp. 1808-1815, vol. 45.

(Continued)

*Primary Examiner*—Michael Burkhart
(74) *Attorney, Agent, or Firm*—Alston & Bird LLP

(57) ABSTRACT

Nucleic acid molecules, fragments and variants thereof having promoter activity are provided in the current invention. The invention also provides vectors containing a nucleic acid molecule of the invention and cells comprising the vectors. Methods for making and using the nucleic acid molecules of the invention are further provided.

10 Claims, 6 Drawing Sheets

OTHER PUBLICATIONS

Barefoot and Klaenhammer, "Purification and Characterization of the *Lactobacillus acidophilus* Bacteriocin Lactacin B," *Antimicrob. Agents Chemother.*, 1984, pp. 328-334, vol. 26.

Barefoot, et al., "Identification and Purification of a Protein that Induces Production of the *Lactobacillus acidophilus* Bacteriocin Lactacin B," *Appl. Environ. Microbiol.*, 1994, pp. 3522-3528, vol. 60.

Barrangou, et al., "Functional and Comparative Genomic Analyses of an Operon Involved in Fructooligosaccharide Utilization by *Lactobacillus acidophilus*," *Proc. Natl. Acad. Sci. U.S.A.*, 2003, pp. 8957-8962, vol. 100.

Boels, et al., "Functional Analysis of the *Lactococcus lactis Gal*u and *Gal*e Genes and Their Impact on Sugar Nucleotide and Exopolysaccharide Biosynthesis," *Appl. Environ. Microbiol.*, 2001, pp. 3033-3040, vol. 67.

Bruno-Barcena, et al., "Expression of Heterologous Manganese Superoxide Dismutase Gene in Intestinal *Lactobacilli* Provides Protection Against Hydrogen Peroxide Toxicity," *Appl. Environ. Microbiol.*, 2004, pp. 4702-4710, vol. 70.

Christensen, et al., "Peptidases and Amino Acid Catabolism in Lactic Acid Bacteria," *Antonie van Leeuwenhoek*, 1999, pp. 217-246, vol. 76.

Coconnier, et al., "Protein-Mediated Adhesion 0f *Lactobacillus acidophilus* bg2fo4 on Human Enterocyte and Mucus-Secreting Cell Lines in Culture," *Appl. Environ. Microbiol.*, 1992, pp. 2034-2039, vol. 58.

Contreras, et al., "Isolation, Purification and Amino Acid Sequence of Lactobin A, One of the Two Bacteriocins Produced by *Lactobacillus amylovorus* LMG P-13139," *Appl. Environ. Microbiol.*, 1997, pp. 13-20, vol. 63.

De Vuyst and Degeest, "Heteropolysaccharides from Lactic Acid Bacteria," *FEMS Microbiol. Rev.*, 1998, pp. 153-177, vol. 23.

Dodd and Gasson, "Bacteriocins of Lactic Acid Bacteria," *Genetics and Biotechnology of Lactic Acid Bacteria*, 1994, pp. 211-251, Blackie Academic and Professional, London.

Fremaux, et al., "Molecular Analysis of the Lactacin F Operon" *Appl. Environ. Microbiol.*, 1993, pp. 3906-3915, vol. 59.

GenBank Accession No. AAA19050; Prolinase; Source: *Lactobacillus helveticus*.

GenBank Accession No. AAA25250; Aminopeptidase C.; Source: *Lactobacillus helveticus*.

GenBank Accession No. AAB52540; Endopeptidase; Source: *Lactobacillus helveticus*.

GenBank Accession No. AAB66326; GroEL; Source: *Lactobacillus zeae*.

GenBank Accession No. AAC29003; Cochaperonin GroES; Source: *Lactobacillus helveticus*.

GenBank Accession No. AAC99363; D-lactate Dehydrogenase; Source: *Lactobacillus johnsonii*.

GenBank Accession No. AAF22492; F1F0-ATPase Subunit A; Source: *Lactobacillus acidophilus*.

GenBank Accession No. AAF22494; F1F0-ATPase Subunit B; Source: *Lactobacillus acidophilus*.

GenBank Accession No. AAF22495; F1F0-ATPase Subunit Delta; Source: *Lactobacillus acidophilus*.

GenBank Accession No. AAF22496; F1F0-ATPase Subunit Alpha; Source: *Lactobacillus acidophilus*.

GenBank Accession No. AAF22497; F1F0-ATPase Subunit Gamma; Source: *Lactobacillus acidophilus*.

GenBank Accession No. AAF22498; F1F0-ATPase Subunit Beta; Source: *Lactobacillus acidophilus*.

GenBank Accession No. AAF22499; F1F0-ATPase Subunit Epsilon; Source: *Lactobacillus acidophilus*.

GenBank Accession No. AAF75593; GroEL; Source: *Lactobacillus johnsonii*.

GenBank Accession No. AAK97217; Cochaperonin GroES; Source: *Lactobacillus acidophilus*.

GenBank Accession No. AAK97218; Chaperonin GroEL; Source: *Lactobacillus acidophilus*.

GenBank Accession No. AAK97220; Cochaperonin GrpE; Source: *Lactobacillus acidophilus*.

GenBank Accession No. AAK97221; Heat Shock Protein DnaK; Source: *Lactobacillus acidophilus*.

GenBank Accession No. AAQ72431; Endopeptidase E2; Source: *Lactobacillus helveticus*.

GenBank Accession No. AAR25444; Tuf; *Lactobacillus johnsonii*.

GenBank Accession No. AAT09141; Amino Acid Permease La995; Source: *Lactobacillus acidophilus*.

GenBank Accession No. AF010281; *Lactobacillus zeae* GroES; Source: *Lactobacillus zeae*.

GenBank Accession No. AF031929; *Lactobacillus helveticus* Cochaperonin Groes and Chaperonin Groel Genes, Complete Cds and Dna Mismatch Repair Enzyme (Hexa) Gene, Partial Cds; Source: *Lactobacillus helveticus*.

GenBank Accession No. AF071558; *Lactobacillus johnsonii* D-Lactate Dehydrogenase (IdhD) Gene, Complete Cds; Source: *Lactobacillus johnsonii*.

GenBank Accession No. AF098522; *Lactobacillus acidophilus* Uracil Phosphoribosyltransferase; Source: *Lactobacillus acidophilus*.

GenBank Accession No. AF214488; *Lactobacillus johnsonii* Groesl Operon, Complete Sequence and Unknown Gene; Source: *Lactobacillus johnsonii*.

GenBank Accession No. AF300645; *Lactobacillus acidophilus* Groesl Operon, Complete Sequence; Source: *Lactobacillus acidophilus*.

GenBank Accession No. AF300646; *Lactobacillus acidophilus* Repressor Protein Hrca (Hrca) Gene, Partial Cds; Cochaperonin Grpe (Grpe) and Heat Shock Protein Dnak (Dnak) Genes, Complete Cds, and Dnaj (Dnaj) Gene, Partial Cds; Source: *Lactobacilus*.

GenBank Accession No. B59088; Prolyl Aminopeptidase; Source: *Lactobacillus helveticus*.

GenBank Accession No. CAA42781; D-lactate dehydrogenase; Source: *Lactobacillus delbrueckii*.

GenBank Accession No. CAA59019; Heat Shock Induced Protein HtpI; Source: *Lactobacillus leichmannii*.

GenBank Accession No. CAA61561; SB-Protein; *Lactobacillus acidophilus*.

GenBank Accession No. CAA86210; Dipeptidase; Source: *Lactobacillus helveticus*.

GenBank Accession No. CAB72938; Tripeptidase Enzyme; Source: *Lactobacillus helveticus*.

GenBank Accession No. NP_964658; Probable Xylulose-5-Phosphate/Fructose-6-Phosphate Phosphoketolase; Source: *Lactobacillus johnsonii* NCC 533.

GenBank Accession No. NP_964694; RecA Protein; Source: *Lactobacillus johnsonii* NCC 533.

GenBank Accession No. NP_964728; Phosphoglycerate Kinase; Source: *Lactobacillus johnsonii* NCC 533.

GenBank Accession No. NP_964948; DNA-Binding Protein HU; Source: *Lactobacillus johnsonii* NCC 533.

GenBank Accession No. NP_965314; 50S Ribosomal Protein L19; Source: *Lactobacillus johnsonii* NCC 533.

GenBank Accession No. NP_965472; thioredoxin; Source: *Lactobacillus johnsonii* NCC 533.

GenBank Accession No. NP_966600; Hypothetica Protein LJ1693; Source: *Lactobacillus johnsonii* NCC 533.

GenBank Accession No. O07684; Beta-Galactosidase Large Subunit; Source: *Lactobacillus acidophilus*.

GenBank Accession No. O07685; Beta-Galactosidase Small Subunit; Source: *Lactobacillus acidophilus*.

GenBank Accession No. O32755; Glyceraldehyde-3-Phosphate Dehydrogenase; Source: *Lactobacillus delbrueckii* Subsp. *bulgaricus*.

GenBank Accession No. O32756; Phosphoglycerate kinase; Source: *Lactobacillus delbrueckii* Subsp. *bulgaricus*.

GenBank Accession No. O32765; L-lactate Dehydrogenase; Source: *Lactobacillus helveticus*.

GenBank Accession No. O68324; 60 kDa Chaperonin; Source: *Lactobacillus helveticus*.

GenBank Accession No. O84913; Xaa-Pro Dipeptidase; Source: *Lactobacillus helveticus*.

GenBank Accession No. P26297; D-Lactate Dehydrogenase; Source: *Lactobacillus delbrueckii* Subsp. *bulgaricus*.

GenBank Accession No. P30901; D-Lactate Dehydrogenase; Source: *Lactobacillus helveticus*.
GenBank Accession No. P34038; Pyruvate kinase; Source: *Lactobacillus delbrueckii* Subsp. *bulgaricus*.
GenBank Accession No. P35829; S-Layer Protein Precursor; Source: *Lactobacilus acidophilus*.
GenBank Accession No. P43451; ATP Synthase Beta Chain; Source: *Enterococcus hirae*.
GenBank Accession No. P94870; Aminopeptidase E.; Source: *Lactobacillus helveticus*.
GenBank Accession No. Q00052; Galactokinase; Source: *Lactobacillus helveticus*.
GenBank Accession No. Q10730; Aminopeptidase N; Source: *Lactobacillus helveticus*.
GenBank Accession No. Q10744; Aminopeptidase C.; Source: *Lactobacillus helveticus*.
GenBank Accession No. Q48558; Dipeptidase A.; Source: *Lactobacillus helveticus*.
GenBank Accession No. Q9Z4H7; Serine Protease Do-Like htrA; Source: *Lactobacillus helveticus*.
GenBank Accession No. S47274; Membrane Alanyl Aminopeptidase; Source: *Lactobacillus helveticus*.
GenBank Accession No. S47276; Prolinase; Source: *Lactobacillus helveticus*.
GenBank Accession No. X60220; *L. delbrueckii* Subsp. *bulgaricus* 1dhA Gene for D-Lactate Dehydrogenase; Source: *Lactobacillus delbrueckii*.
GenBank Accession No. X84261; *L. leichmannii* xerC, hslU and hslV; Source: *Lactobacillus leichmannii*.
GenBank Accession No. X89376; *L. acidophilus* DNA for SB-Protein Gene; Source: *Lactobacillus acidophilus*.
GenBank Accession No. ZP_00046537; COG0124: Histidyl-tRNA Sythetase; Source: *Lactobacillus ggasseri*.
GenBank Accession No. ZP_00046557; COG0148: Enolase; Source: *Lactobacillus gasseri*.
GenBank Accession No. ZP_00046583; COG0195: Transcription Elongation Factor; Source: *Lactobacillus gasseri*.
GenBank Accession No. ZP_00047305; COG4690: Dipeptidase; Source: *Lactobacillus gasseri*.
GenBank Accession No. ZP_00341831; COG0522: Ribosomal Protein S4 and Related Proteins; Source: *Lactobacillus gasseri*.
GenBank Accession No. Q03234; ATP Synthesis Beta Chain; *Lactobacillus casei*.
Girgis, et al., "Stress Adaptations of Lactic Acid Bacteria," *Microbial Adaptation to Stress and Safety of New-Generation Foods*, 2002, pp. 159-212, CRC Press, NY.
Greene and Klaenhammer, "Factors Involved In Adherence Of Lactobacilli To Human Caco-2 Cells," *Appl. Environ. Microbiol.*, 1994, pp. 4487-4494, vol. 60.
Holzapfel, et al., "Taxonomy and Important Features of Probiotic Microorganisms in Food and Nutrition" *Am J of Clil Nutr*, 2001, pp. 365S-373S, vol. 73 Suppl.
Hugenholtz, "Metabolic Engineering of Lactic Acid Bacteria: Overview of the Approaches and Results of Pathway Rerouting Involved in Food Fermentations," *Current Opinion in Biotechnology*, 1999, pp. 492-497, vol. 10.
Joerger and Klaenhammer, "Characterization And Purification Of Helveticin J And Evidence For A Chromosomally Determined Bacteriocin Produced By *Lactobacillus helveticus*," *J. Bacteriol.*, 1986, pp. 439-446, vol. 167.
Joerger, et al., "Cloning, Expression, And Nucleotide Sequence Of The *Lactobacillus helveticus* 481 Gene Encoding The Bactericin Helveticin J," *J. Bacteriol.*, 1990, pp. 6339-6347, vol. 172.
Jolly, et al., "Exploiting Exopolysaccharides from Lactic Acid Bacteria," Antonie van Leeuwenhoek, 2002, pp. 367-374, vol. 82.
Klaenhammer, "Bacteriocins of Lactic Acid Bacteria," *Biochimie*, 1988, pp. 337-349, vol. 70.
Klaenhammer, "Genetics of Bacteriocins Produced By Lactic Acid Bacteria," *FEMS Microbiol. Rev.*, 1993, pp. 39-85, vol. 12.
Klaenhammer, "Probiotic Bacteria: Today And Tomorrow," *J. Nutr.*, 2000, pp. 415S-416S, vol. 130(2S Suppl.).
Klaenhammer and Kullen, "Selection and Design of Probiotics," *Int. J. Food Microbiol.*, 1999, pp. 45-57, vol. 50.

Klaenhammer and Sutherland, "Detection of Plasmid Deoxyribonucleic Acid in an Isolate of *Lactobacillus acidophilus*," *Appl. Environ. Microbiol.*, 1980, pp. 671-674, vol. 39.
Klaenhammer, et al., "Discovering lactic acid bacteria by genomics," Antonie van Leeuenhoek, 2002, pp. 29-58, vol. 82.
Klaenhammer and Kullen (1999) "Selection and design of probiotics" *Int. J. Food Microbiol*. 50:45-57.
Klaenhammer and Sutherland (1980) "Detection of plasmid deoxyribonucleic acid in an isolate of *Lactobacillus acidophilus*" *Appl. Environ. Microbiol*. 39:671-674.
Klaenhammer et al. (2005) "*Lactobacillus acidophilus* Nucleic Acid Sequences Encoding Protease Homologues and Uses Therefore" U.S. Appl. No. 11/062,665, filed Feb. 22, 2005.
Klaenhammer et al. (2005) "*Lactobacillus acidophilus* Nucleic Acid Sequences Encoding Carbohydrate Utilization-Related Proteins and Uses Therefor" U.S. Appl. No. 11/074,226.
Kleeman and Klaenhammer, "Adherence of *Lactobacillus* Species to Human Fetal Intestinal Cells" *J. Dairy Sci.*, 1982, pp. 2063-2069, vol. 65.
Kleerebezem, et al., "Exopolysaccharides Produced by *Lactococcus lactis*: from Genetic Engineering to Improved Rheological Properties?," Antonie van Leeuwenhoek, 1999, pp. 357-365, vol. 76.
Kleerebezem, et al., "Complete genome sequence of *Lactobacillus plantarum* WCFS1," *Proc. Natl. Acad. Sci. U.S.A.*, 1990-1995, pp. 2003, vol. 100.
Kok, et al., "The Proteolytic System of Lactic Acid Bacteria," *Genetics and Biotechnology of Lactic Acid Bacteria*, 1994, pp. 169-210.
Konigs, et al., "The Role of Transport Processes in Survival of Lactic Acid Bacteria," Antonie van Leeuwenhoek, 1997, pp. 117-128, vol. 71.
Konigs, et al., "Lactic Acid Bacteria: The Bugs of a New Millennium," *Curr. Opin. Microbiol.*, 2000, pp. 276-282, vol. 3.
Kuipers, et al., "Current Strategies for Improving Food Bacteria," *Res Microbiol*, 2000, pp. 815-822, vol. 151.
Kullen and Klaenhammer, "Identification of the pH-Inducible, Proton-Translocating $F_1f_0$-Atpase (atpbefhagdc) Operon of *Lactobacillus acidophilus* by Differential Display: Gene Structure, Cloning and Characterization," *Mol. Microbiol.*, 1999, pp. 1152-1161, vol. 33.
Kullen and Klaenhammer, "Genetic Modification of Intestinal *Lactobacilli* and *Bifidobacteria*," *Curr. Issues Mol. Biol.*, 2000, pp. 41-50, vol. 2.
Kullen, et al., "Use of the DNA Sequence of Variable Regions of the 16s Rrna Gene for Rapid and Accurate Identification of Bacteria in the *Lactobacillus acidophilus* Complex," *J. Appl. Microbiol.*, 2000, pp. 511-516, vol. 89.
Law, et al., "Proteolytic Enzymes of Lactic Acid Bacteria" *Int Dairy Journal*, 1997, pp. 1-11, vol. 7.
Luchansky, et al., "Application of Electroporation for Transfer of Plasmid DNA to *Lactobacillus, Lactococcus, Leuconostoc, Listeria, Pediococcus, Bacillus, Staphylococcus, Enterococcus* and *Propionobacterium*" *Mol. Microbiol.*, 1988, pp. 637-646, vol. 2.
Luchansky, et al., "Genetic Transfer Systems for Delivery of Plasmid Deoxyribonucleic Acid to *Lactobacillus acidophilus* Adh: Conjugation, Electroporation, and Transduction," *J. Dairy Sci.*, 1989, pp. 1408-1417, vol. 72.
Luchansky, et al., "Molecular Cloning and Deoxyribonucleic Acid Polymorphisms in *Lactobacillus acidophilus* and *Lactobacillus gasseri*," *J. Dairy Sci.*, 1991, pp. 3293-3302, vol. 74.
Majhenic, et al., "DNA Analysis of the Genes Encoding Acidocin Lf221 A and Acidocin Lf221 B, Two Bacteriocins Produced by *Lactobacillus gasseri* LF221," *Appl. Microbiol. Biotechnol.*, 2004, pp. 705-714, vol. 63.
Mohamadzadeh, et al., "*Lactobacilli* Activate Human Dendritic Cells That Skew T Cells Toward T Helper 1 Polarization," *Proc. Nat. Acad. Sci. USA*, 2005, pp. 2880-2885, vol. 102.
Muriana and Klaenhammer, "Cloning, Phenotypic Expression, and DNA Sequence of the Gene For Lactacin F, An Antimicrobial Peptide Produced By *Lactobacillus* Spp.," *J. Bacteriol.*, 1991, pp. 1779-1788, vol. 173.
Muriana and Klaenhammer, "Purification and Partial Characterization of Lactacin F, A Bacteriocin Produced by *Lactobacillus acidophilus* 11088," *Appl. Environ. Microbiol.*, 1991, pp. 114-121, vol. 57.

Pao, et al., "Major Facilitator Superfamily," *Microbiol. Mol. Biol. Rev.*, 1998, pp. 1-34, vol. 62.

Poolman, "Transporters and Their Roles in LAB Cell Physiology," *Antonie van Leeuwenhoek*, 2002, pp. 147-164, vol. 82.

Pridmore, et al. "The Genome Sequence of the Probiotic Intestinal Bacterium *Lactobacillus johnsonii* NCC 533," *Proc. Natl. Acad. Sci. U.S.A.*, 2004, pp. 2512-2517, vol. 101.

Putman, et al., "Molecular Properties Of Bacterial Multidrug Transporters," *Microbiol. Mol. Biol. Rev.*, 2000, pp. 672-693, vol. 64.

Rastall, et al., "Modulation of the Microbial Ecology of the Human Colon by Probiotics, Prebiotics and Synbiotics to Enhance Human Health: An Overview of Enabling Science and Potential Applications," *FEMS Microbiol. Ecol.*, 2005, pp. 145.

Roy, et al., "Cloning and Expression of the Manganese Superoxide Dismutase Gene of *Escherichia coli* in *Lactococcus lactis* and *Lactobacillus gasseri*," *Mol. Gen. Genet.*, 1993, pp. 33-40, vol. 239.

Russell and Klaenhammer, "Efficient System for Directed Integration into the *Lactobacillus acidophilus* and *Lactobacillus gasseri* Chromosomes Via Homologous Recombination," *Appl. Environ. Microbiol.*, 2001, pp. 4361-4364, vol. 67.

Russell and Klaenhammer, "Identification and cloning of *gus*A, encoding a new β-glucuronidase from *Lactobacillus gasseri* ADH," *Appl. Environ. Microbiol.*, 2001, pp. 1253-1261, vol. 67.

Sablon, et al., "Antimicrobiol Peptides of Lactic Acid Bacteria: Mode of Action, Genetics and Biosynthesis," *in Advances in Biochemical Engineering/Biotechnology.*, 2000, pp. 21-60, vol. 68, Springer-Verlag, Berlin.

Sanders and Klaenhammer, "Invited Review: The Scientific Basis of *Lactobacillus acidophilus* ncfm Functionality as a Probiotic," *J. Dairy Sci.*, 2001, pp. 319-331, vol. 84.

Sanders, et al., "Performance of Commercial Cultures in Fluid Milk Applications," *J. Dairy Sci.*, 1996, pp. 943-955, vol. 79.

Steidler et al., "Functional Display of a Heterologous Protein on the Surface of *Lactococcus lactis* by Means of the Cell Wall Anchor of *Staphylococcus aureus* Protein A," *Appl. Environ. Microbiol.*, 1998, pp. 342-345, vol. 64.

Sturino and Klaenhammer, "Bacteriophage Defense Systems for Lactic Acid Bacteria," *Adv. Appl. Microbiol.*, 2004, pp. 331-378, vol. 56.

Ventura, et al., "Analysis, Characterization, and Loci tf *Tuf* Genes in *Lactobacillus* and *Bifidobacterium* Species and Their Direct Application for Species Identification," *Appl. Environ. Microbiol.*, 2003, pp. 6908-6922, vol. 69.

Walker, et al. "The groESL Chaperone Operon of *Lactobacillus johnsonii*," *Appl. Environ. Microbiol.*, 1999, pp. 3033-3041, vol. 65.

Yother, et al., Genetics of *Streptococci, Lactococci*, and *Enterococci*: Review of the Sixth International Conference, *J. Bacteriol.*, 2002, pp. 6085-6092, vol. 184.

Barrangou, R., et al., "Global Analysis for Carbohydrate Utilization by *Lactobacillus acidophilus* using cDNA Microarrays", Mar. 7, 2006, *PNAS*, vol. 103, No. 10, pp. 3816-3821.

McCracken, A., and Timms, P., "Efficiency of Transcription from Promoter Sequence Variants in *Lactobacillus* is both Strain and Context Dependent", *Journal of Bacteriology*, Oct. 1999, vol. 181, No. 20, pp. 6569-6572.

\* cited by examiner

* - GUS activity not detected at 0 hrs post induction

COMPOSITIONS COMPRISING PROMOTER SEQUENCES AND METHODS OF USE

CROSS-REFERENCE TO RELATED APPLICATION

This application claims the benefit of U.S. Provisional Application No. 60/644,189, filed Jan. 14, 2005, which is herein incorporated by reference in its entirety.

FIELD OF THE INVENTION

The present invention is directed to promoters in general, as well as, nucleic acid constructs comprising such promoters operably associated with a nucleic acid of interest in a recombinant nucleic acid molecule, cells containing the same, and methods of making and using the same.

BACKGROUND OF THE INVENTION

The gastrointestinal tract is the most densely colonized region of the human body (Savage, Ann. Rev. Microbiol. 31, 107 (1977); Tannock, Normal microflora (Chapman and Hall, London 1995)) and the accumulated evidence indicates that this collection of microbes has a powerful influence on the host in which it resides. Comparisons between germ free and conventional animals have shown that many biochemical, physiological and immunological functions are influenced by the presence of the diverse and metabolically active bacterial community residing in the gastrointestinal tract (Marteau and Rambaud, FEMS Microbiol. Rev. 12, 207 (1993); Norin et al., Appl. Environ. Microbiol. 74, 1850 (1991); Tannock, supra). Lactobacilli are important residents of the microflora (Ahrne et al., J. Appl. Microbiol. 85, 88 (1998); Kimura et al., Appl. Environ. Microbiol. 63, 3394 (1997)), and have been the subject of intense and growing interest because of their possible role in the maintenance of gastrointestinal health (Bengmark, Gut 42, 2 (1998)). Of immense importance to lactobacilli functioning in this role is the ability to endure in the harsh conditions of the gastrointestinal tract, where the gastric pH frequently falls below 2.0 in healthy individuals (McLauchlan et al., Gut 30, 573 (1998)).

The identification of conditionally expressed genes provides a wealth of insight into the physiological consequences of and responses to a given stimulus. In the case of Lactobacillus acidophilus, a significant challenge has been in understanding the intestinal roles and activities of this organism. An important element in this regard is the determination of which characteristics are important for the survival and success of this organism in the gastrointestinal tract. While differential display (Liang and Pardee, Science 257, 967 (1992); Welsh et al., Nucleic Acids Res. 20, 4965 (1992)) has been used extensively to identify conditionally expressed genes in eukaryotes, the application of this methodology in prokaryotes has not been explored to a comparatively significant extent (Abu Kwaik and Pederson, Mol. Microbiol. 21, 543 (1996); Fislage, Electrophoresis 19, 613 (1998); Fislage et al., Nucleic Acids Res. 25, 1830 (1997); Wong and McClelland, Proc. Natl. Acad. Sci. USA 91, 639 (1994); Zhang and Normark, Science 273, 1234 (1996)). Some of the practical problems in employing these methods in prokaryotes include the relatively large proportion of structural RNA species in the total RNA, the low level of polyadenylation of mRNA (Sarkar, Ann. Rev. Biochem. 66, 173 (1997)), which prohibits the use of 3' dT anchored primers and the structural instability and short half life of low abundance mRNA species of prokaryotes as compared to eukaryotes (Higgins et al., Curr. Opin. Genet. Dev. 2:739 (1992)).

The present invention contributes to the art by providing promoters as compositions and for use in methods of expressing nucleic acids in a variety of conditions.

SUMMARY OF THE INVENTION

Figure 1:
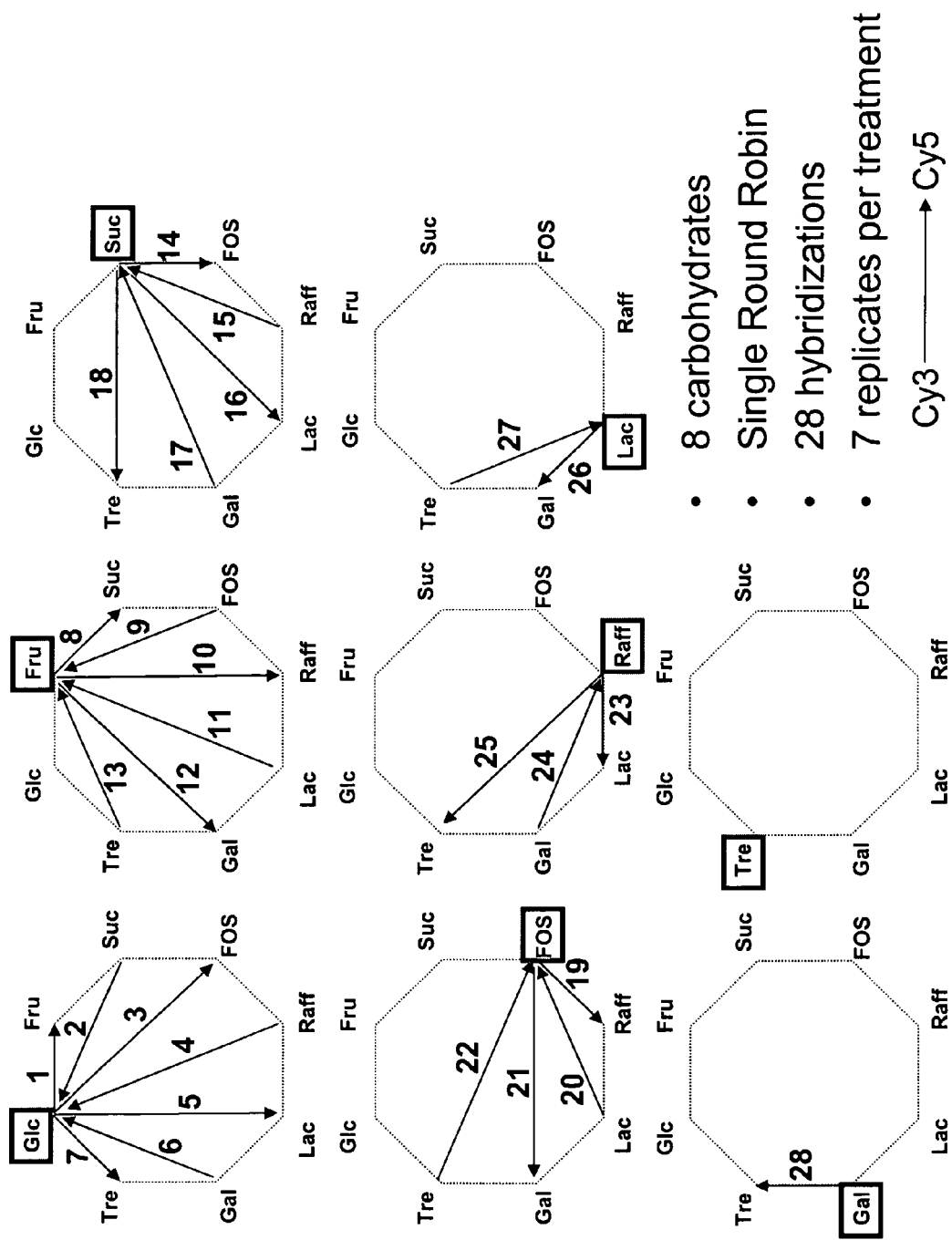
FIG. 1 is a schematic of the experimental design of the microarray assays described herein.

Methods and compositions for regulating gene expression are provided.

Compositions comprise isolated nucleic acid molecules comprising (a) a nucleic acid comprising a nucleotide sequence as set forth in any one of SEQ ID NOS:1-80 or a fragment thereof; (b) a nucleic acid that hybridizes to the complement of the nucleic acid of (a) under stringent conditions, wherein the sequence has promoter activity; and (c) a nucleic acid having at least 70%, 80%, 90%, 95% or greater sequence identity to the nucleotide sequence set forth in any one of SEQ ID NOS:1-80, wherein the sequence has promoter activity.

Further provided are recombinant nucleic acid molecules of SEQ ID NOS:1-80 or biologically active variants or fragments thereof, wherein the molecules are operably linked to a heterologous nucleic acid of interest. Vectors having such recombinant nucleic acid molecules are also provided, as are cells having a heterologous nucleic acid molecule comprising the sequence of SEQ ID NOS:1-80 and biologically active variants thereof.

Further provided are methods for controlling the transcription of a nucleic acid of interest. One method comprises (a) providing or maintaining the cell under non-inducing conditions, wherein the cell comprises at least one of the recombinant nucleic acid molecules of any one of SEQ ID NOS:1-80 or a biologically active variant or fragment thereof or a vector having the same, and (b) subjecting the cell to inducing conditions whereby transcription of the nucleic acid of interest is increased as compared to the level of transcription of the nucleic acid of interest under non-inducing conditions. Inducing conditions can be produced by increasing or decreasing the pH of the cell relative to the pH of the cell under non-inducing conditions; by administering or delivering the cell to a body cavity of the subject, wherein the body cavity has an acidic pH environment; by the fermentative production of an acid by the cell in a cell culture; by an increase or decrease in temperature of the cell relative to the temperature of the cell under non-inducing conditions; by an increase or decrease in the concentration of a sugar in the cell relative to the concentration of the sugar in the cell under non-inducing conditions; or, by the presence of a stress response protein.

Further included is a method to express a nucleotide sequence of interest in a cell comprising introducing into the cell a heterologous nucleic acid molecule comprising any one of SEQ ID NOS:1-80 or a biologically active variant or fragment thereof, wherein the nucleic acid molecule is operably linked to a nucleotide sequence of interest.

The foregoing and other objects and aspects of the invention are described herein and the specification set forth below.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides isolated nucleic acid molecules comprising, consisting essentially of and/or consisting of the nucleotide sequences as set forth in SEQ ID NOS:1-80. Also provided are isolated nucleic acid molecules having promoter activity, wherein the nucleic acid molecule is selected from the group consisting of: (a) a nucleic acid molecule comprising, consisting essentially of, and/or consisting of a nucleotide sequence as set forth in SEQ ID NOS: 1-80 or a fragment thereof; (b) a nucleic acid molecule that hybridizes to the complement of the nucleic acid molecule of (a) under stringent conditions and has promoter activity; and (c) a nucleic acid molecule having at least 70%, 80%, 90%, 95% or greater sequence identity to the nucleic acid molecule of (a) or (b) and has promoter activity. A nucleic acid molecule having a nucleotide sequence that is complementary to any one of the nucleic acid molecules described herein is also provided in this invention.

In other embodiments, the present invention provides isolated nucleic acid molecules comprising the nucleotide sequences as set forth in SEQ ID NOS: 6, 72, or 73. Also provided are isolated nucleic acid molecules having promoter activity, wherein the nucleic acid molecule is selected from the group consisting of: (a) a nucleic acid molecule comprising, consisting essentially of, and/or consisting of a nucleotide sequence as set forth in SEQ ID NOS: 6, 72, or 73 or a fragment thereof; (b) a nucleic acid molecule that hybridizes to the complement of the nucleic acid molecule of (a) under stringent conditions and has promoter activity; and (c) a nucleic acid molecule having at least 70%, 80%, 90%, 95% or greater sequence identity to the nucleic acid molecule of (a) or (b) and has promoter activity.

Variant nucleic acid molecules sufficiently identical to the nucleotide sequences set forth herein are also encompassed by the present invention. Additionally, fragments and sufficiently identical fragments of the nucleotide sequences are encompassed. Nucleotide sequences that are complementary to a nucleotide sequence of the invention, and/or that hybridize to a nucleotide sequence, or complement thereof, of the invention are also encompassed.

Compositions of this invention further include vectors and cells for recombinant expression of the nucleic acid molecules described herein, as well as transgenic microbial and/or cell populations comprising the nucleic acids and/or vectors. Also included in the invention are methods for the recombinant production of heterologous peptides and/or polypeptides and methods for their use.

Another aspect of the present invention is an isolated nucleic acid comprising: (a) a first nucleotide sequence having promoter activity, wherein the promoter can be a constitutively active promoter or an inducible promoter, wherein the latter can be induced by a variety of factors, including but not limited to, pH, growth temperature, oxygen content, a temperature shift, the composition of the growth medium (including the ionic strength/NaCl content), the presence or absence of essential cell constituents or precursors, the growth phase and/or the growth rate of a cell or cell population, and any of a variety of inducing compounds and/or chemicals that are well known in the art, as described herein; and (b) a second nucleotide sequence having a position, orientation, presence and/or sequence which imparts a regulatory effect on the expression of a nucleic acid sequence operably linked to the first nucleotide sequence having promoter activity. A nucleic acid molecule of this embodiment can be, for example, a nucleic acid having a nucleotide sequence as set forth in SEQ ID NOS:1-80 or SEQ ID NO:6, 72, or 73 as provided herein, and/or a nucleic acid that hybridizes with the complement of a nucleic acid having the nucleotide sequence as set forth in SEQ ID NOS:1-80 or SEQ ID NO:6, 72, or 73 and has the promoter and regulatory activity described herein. The nucleic acid molecule of this embodiment can also be a nucleic acid molecule having at least 70% homology to a nucleic acid molecule having a nucleotide sequence of SEQ ID NOS:1-80 or SEQ ID NO: 6, 72, or 73 and having promoter and regulatory activity as described herein.

In one embodiment, the nucleic acid molecule according to the present invention may be induced by sugar (including, but not limited to, glucose, fructose, sucrose, trehalose, fructooligosaccharide, raffinose, lactose and/or galactose) and may be referred to herein as a "sugar-induced" promoter. Suitably at least SEQ ID NOS:70-80 may be sugar-induced promoters.

In another embodiment, the nucleic acid molecule according to the present invention may be induced by exposure to a stress response (including, but not limited to, change in pH, exposure to bile, oxalate and/or ethanol alone or in various combinations) or to a stress response protein and may be referred to herein as a "stress-induced" promoter. Suitably at least SEQ ID NOS:44-69 may be stress-induced promoters. In other embodiments, exposure to a stress response contributes to repression of a promoter.

In another embodiment, the nucleic acid molecule according to the present invention may be induced by growth temperature or a shift in temperature (and may be referred to herein as a "temperature-induced" promoter).

In another embodiment, the nucleic acid molecule according to the present invention may be induced by Fos (and may be referred to herein as a "Fos-induced" promoter). Suitably at least SEQ ID NO: 72.

The nucleic acid molecules comprising promoters of the present invention have applications in a number of scenarios. The promoters of this invention can be used for the expression of nucleic acid molecules to yield gene products, for example, during the normal course of fermentation by cells such as bacterial cells, particularly lactic acid bacteria, in dairy, meat, vegetable, cereal, and other bioconversions. The promoters of this invention can also be used for the production of gene products upon exposure of lactic acid bacteria to certain environmental stimuli (e.g., acid environments), including, for example, suspension into acidified foods or entry into the gastrointestinal tract or other body cavities as probiotic bacteria.

The nucleic acid molecules of this invention can be used in some embodiments for the expression of nucleic acid molecules encoding enzymes, antigens, proteins, peptides, etc., from lactic acid and/or other bacteria that can be used, for example, as delivery or production systems.

Accordingly, a further aspect of the invention is a recombinant nucleic acid comprising a promoter of this invention operably associated with a nucleic acid of interest. In some embodiments, the nucleic acid of interest can encode a protein or peptide, the production of which can be upregulated, e.g., upon induction of the promoter. In other embodiments, the nucleic acid of interest can encode an antisense oligonucleotide that can suppress or inhibit the production of a protein in a cell, e.g., upon induction of the promoter. In other embodiments, the nucleic acid of interest can encode a ribozyme, an interfering RNA (RNAi), etc., that would be useful, for example, in situations where regulation of gene expression and/or protein production is desired.

As noted above, in some embodiments, the nucleic acid of interest can encode an antisense RNA. In general, "antisense" refers to the use of small, synthetic oligonucleotides to inhibit protein production by inhibiting the function of the target mRNA containing the complementary sequence (Milligan et al. (1993) *J. Med. Chem.* 36(14):1923-1937). Protein production is inhibited through hybridization of the antisense sequence to coding (sense) sequences in a specific mRNA target by hydrogen bonding according to Watson-Crick base pairing rules. The mechanism of antisense inhibition is that the exogenously applied oligonucleotides decrease the mRNA and protein levels of the target gene (Milligan et al. (1993) *J. Med. Chem.* 36(14):1923-1937). See also Helene and Toulme(1990) *Biochim. Biophys. Acta* 1049:99-125; (Cohen, J. S., ed. (1987) *Oligodeoxynucleotides as antisense inhibitors of gene expression* (CRC Press:Boca Raton, Fla.)).

An additional aspect of the invention includes vectors and cells for recombinant expression of the nucleic acid molecules described herein, as well as transgenic cell populations comprising the vectors and/or nucleic acids of this invention. Also included in the invention are methods for the expression of nucleic acids of interest of this invention, resulting, for example, in the production of heterologous polypeptides and/or peptides, and methods for their use.

It is to be understood that in some embodiments of this invention, the nucleic acids of this invention encoding either a promoter or a nucleic acid of interest can be present in any number, in any order and in any combination, either on a single nucleic acid construct or on multiple nucleic acid constructs. For example, a promoter sequence and/or a nucleotide sequence of interest can be present as a single copy or as multiple copies on the same construct and/or on multiple constructs. Also, different promoter sequences and/or different nucleotide sequences of interest can be present on the same construct and/or on multiple constructs in any combination of multiple and/or single copies.

Further aspects of the invention include a method of transforming a cell with a nucleic acid and/or vector of this invention, comprising introducing the nucleic acid and/or vector of this invention into the cell according to methods well known in the art for transformation of cells with nucleic acid molecules. Where the nucleic acid of interest is to be transcribed within the cell, the cell can be one in which the promoter is operable (e.g., inducible by some stimulus such as acid pH or constitutively active). The nucleic acid of interest can be from a different organism than the transformed cell (e.g., a heterologous nucleic acid of interest), or the nucleic acid can be from the same organism as is the transformed cell, although in a recombinant nucleic acid molecule (in which case the nucleic acid of interest is heterologous in that it is not naturally occurring in the transformed cell).

A still further aspect of the invention is a method of controlling the transcription of a nucleic acid of interest, comprising: (a) providing a cell under non-inducing conditions, wherein the cell comprises a recombinant nucleic acid molecule that comprises an inducible promoter of this invention operably associated with a nucleic acid of interest; and (b) exposing, subjecting or introducing the cell to inducing conditions, e.g., an inducing environment whereby the promoter is induced to activate transcription of the nucleic acid of interest. The inducing environment can be an environment having a specific pH (e.g., an acidic pH) due to an increase or decrease in the pH as compared to non-inducing conditions, or having a specific temperature due to an increase or decrease of temperature as compared to non-inducing conditions, or containing an inducing element (e.g., a molecule or compound) that acts to induce the promoter to activate or increase transcription, resulting in a level of transcription that is greater than the level of transcription when the inducing environment or inducing element is not present, i.e., under non-inducing conditions. Thus, a non-inducing condition is meant to include conditions wherein the inducible promoter is not active or is not fully active in directing transcription.

Examples of inducing elements include, but are not limited to, organic acids (lactate, acetate, oxalate), pH, sodium chloride, oxygen, hydrogen peroxide, bile, ethanol, and carbohydrates (monosaccharides, disaccharides, oligosaccharides, and galactosides such as glucose, fructose, sucrose, trehalose, fructooligosaccharide, raffinose, lactose, and galactose).

In embodiments wherein the promoter is induced by exposure to an acidic pH, the inducing step can be carried out by any suitable means, including but not limited to, adding an exogenous acid to a cell in a culture, administering or delivering a cell to an acidic body cavity of a subject, producing an acid by fermentation in a cell culture, etc.

The nucleic acid of interest can encode various products, including but not limited to, a protein and/or peptide (e.g., an enzyme, a hormone, a growth factor, a cytokine, an antigen, a pro-drug, etc.) which can be both transcribed and translated in the cell), an antisense oligonucleotide, a ribozyme and/or an interfering RNA, etc. Suitable nucleic acids of interest can be of prokaryotic or eukaryotic origin.

As used herein, "a," "an" or "the" can be singular or plural. For example, "a cell" can mean a single cell or a multiplicity of cells.

The present invention provides promoters. Thus, in some embodiments of the invention, a nucleic acid molecule having promoter activity is provided comprising, consisting essentially of and/or consisting of a nucleotide sequence as set forth in SEQ ID NOS:1-80 or SEQ ID NO: 6, 72, or 73 or fragments (e.g., active fragments) or active variants thereof. Also provided is a nucleic acid molecule comprising, consisting essentially of and/or consisting of a nucleic acid having promoter activity operatively associated with a nucleic acid having activity as a regulatory element as described herein, which regulates the ability of the promoter sequence to activate transcription.

The nucleic acids of this invention are isolated and/or substantially purified. By "isolated" or "substantially purified" is meant that the nucleic acid, and/or fragments or variants, are substantially or essentially free from components normally found in association with nucleic acid in its natural state. Such components can include cellular material, culture medium from recombinant production, and/or various chemicals and reagents used in chemically synthesizing nucleic acids. An "isolated" nucleic acid of the present invention is free of nucleotide sequences that flank the nucleic acid of interest in the genomic DNA of the organism from which the nucleic acid was derived (such as coding sequences present at the 5' or 3' ends). However, the nucleic acid molecule of this invention can, in some embodiments, include additional bases and/or moieties that do not deleteriously affect the basic characteristics and/or activities of the nucleic acid. Identification of such additional bases and/or moieties that do not have such a deleterious effect can be carried out by methods well known in the art.

In certain embodiments, the nucleic acid molecules of the present invention can be used to modulate the function of molecules. By "modulate," "alter," or "modify" is meant the up- or down-regulation of a target activity. Up- or down-regulation of expression of a nucleic acid of the present invention is encompassed. Up-regulation can be accomplished, for example, by 1) providing multiple copies of the nucleic acids of this invention, 2) modulating expression by modifying regulatory elements, 3) promoting transcriptional or translational mechanisms and 4) any other means known to upregulate expression of nucleic acid. Down-regulation can be accomplished, for example, by using well-known antisense and gene silencing techniques. "modify" is intended the up- or down-regulation of a target biological activity.

By "lactic acid bacteria" is meant bacteria from a genus selected from the following: Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus, and Weissella (Holzapfel et al. (2001) Am. J. Clin. Nutr. 73:365S-373S; Williams and Wilkins (1986) Bergey's Manual of Systematic Bacteriology 2: 1075-1079 Baltimore).

By "Lactobacillus" is meant any bacteria from the genus Lactobacillus, including but not limited to L. casei, L. paracasei, L. rhamnosus, L. johnsonni, L. gasserei, L. acidophilus, L. crispatus, L. galinarum, L. plantarum, L. fermentum, L. salivarius, L. helveticus, L. bulgaricus, and numerous other species outlined by Wood et al. (Holzapfel, W. H. N. The Genera of Lactic Acid Bacteria, Vol. 2. 1995. Brian J. B. Wood, Ed. Aspen Publishers, Inc.)

The nucleic acid molecules of the present invention are also useful in modifying milk-derived products. These uses include, but are not limited to, modulating the growth rate of a bacterium, modifying the flavor of a fermented dairy product, modulating the acidification rate of a milk product fermented by lactic acid bacteria, and altering products produced during fermentation.

In addition to the isolated nucleic acid molecules comprising nucleotide sequences as set forth in SEQ ID NOS:1-80 or SEQ ID NOS: 6, 72, or 73, the present invention also provides fragments and variants of these nucleotide sequences. By "fragment" of a nucleotide sequence is meant a nucleic acid molecule that is made up of a nucleotide sequence that is the same as a portion of a nucleotide sequence of SEQ ID NOS: 1-80, but has fewer nucleotides than the entire nucleotide sequence as set forth in SEQ ID NOS:1-80, as well as, a nucleic acid molecule that is made up of a nucleotide sequence that has fewer nucleotides than the entire nucleotide sequence of a nucleic acid that has substantial homology to a nucleotide sequence of SEQ ID NOS:1-80 as described herein and also including a nucleic acid molecule that is made up of nucleotide sequence that has fewer nucleotides than the entire nucleotide sequence of a nucleic acid that hybridizes to a nucleotide sequence of SEQ ID NOS:1-80 or the complement thereof, under the conditions described herein.

In one embodiment of the invention, fragments of the polynucleotides of SEQ ID NOS:1-80 are provided. A biologically active fragment of a polynucleotide of SEQ ID NOS:1-80 can comprise, for example, 5, 10, 15, 20, 25, 30, 40, 50, 75, 100, 150, 200, 300, 400, or 500 contiguous nucleotides in length, including any number between 5 and 500 not specifically recited herein, or up to the total number of nucleotides present in a full-length polynucleotide of the invention. Such biologically active fragments can continue to be biologically active (i.e., have promoter activity).

In another embodiment of the invention, fragments of the polynucleotides of SEQ ID NOS: 6, 72 or 73 are provided. A biologically active fragment of a polynucleotide of SEQ ID NOS:6, 72, or 73 can comprise, for example, 5, 10, 15, 20, 25, 30, 40, 50, 75, 100, 150, 200, 300, 400, or 500 contiguous nucleotides in length, including any number between 5 and 500 not specifically recited herein, or up to the total number of nucleotides present in a full-length polynucleotide of the invention. Such biologically active fragments can continue to be biologically active (i.e., have promoter activity).

An "active fragment" of this invention is a fragment of a nucleotide sequence of this invention that has activity, such as promoter activity and/or promoter-regulating activity as determined by any well-known protocol for detecting and/or measuring promoter activity and/or promoter-regulating activity. An active fragment can also include a fragment that is functional as a probe and/or primer. For example, fragments of the nucleic acids disclosed herein can be used as hybridization probes to identify nucleic acids in a sample having varying degrees of homology to the nucleic acid molecules of this invention, and/or can be used as primers in amplification protocols (e.g., polymerase chain reaction (PCR) or other well-known amplification methods) and/or to introduce mutations into a nucleotide sequence. In some embodiments, fragments of this invention can be bound to a physical substrate to comprise a macro- or microarray (see, for example, U.S. Pat. No. 5,837,832; U.S. Pat. No. 5,861, 242; U.S. Pat. No. 6,309,823, and International Publication Nos. WO 89/10977, WO 89/11548, and WO 93/17126). Such arrays of nucleic acids can be used to study gene expression and/r to identify nucleic acid molecules with sufficient identity to the target sequences.

A "variant" of a nucleic acid of this invention includes a nucleotide sequence that is substantially homologous to, but not identical to, a nucleic acid of this invention and that retains activity as described herein. By "substantially homologous" is meant that the variant nucleic acid has at least 50, 60, 70, 80, 85, 90, 91, 92, 93, 94, 95, 96, 97, 98 or 99% sequence identity with a nucleic acid of this invention, as further described herein.

In one embodiment of the invention, variants of polynucleotides of SEQ ID NOS:1-80 are provided. A variant of a polynucleotide of SEQ ID NOS:1-80 can comprise, in general, nucleotide sequences that have at least about 45%, 55%, 65%, 70%, 75%, 80%, 85% or 90%, 91%, 92%, 93%, 94%, 95%, 95%, 96%, 97%, 98%, or 99% sequence identity to SEQ ID NOS:1-80. Biologically active variants can continue to be biologically active (i.e., have promoter activity).

In another embodiment of the invention, variants of polynucleotides of SEQ ID NOS:6, 72 or 73 are provided. A variant of a polynucleotide of SEQ ID NOS:6, 72, or 73 can comprise, in general, nucleotide sequences that have at least about 45%, 55%, 65%, 70%, 75%, 80%, 85% or 90%, 91%, 92%, 93%, 94%, 95%, 95%, 96%, 97%, 98%, or 99% sequence identity to SEQ ID NOS:6, 72, or 73. Biologically active variants can continue to be biologically active (i.e., have promoter activity).

The present invention further encompasses homologous nucleic acid sequences identified and/or isolated from other organisms or cells by hybridization with entire or partial nucleic acid sequences of the present invention, as well as, variants and/or fragments thereof. Such hybridization protocols are standard in the art and some examples are provided herein.

An active nucleotide fragment of this invention can be prepared by various methods known in the art, such as by 1) chemical synthesis, 2) restriction digestion, 3) selective amplification and 4) selective isolation of a desired fragment. The activity of the fragment can be determined by well-known methods as described herein. In some embodiments, a fragment of a nucleic acid of this invention can comprise at least about 5, 10, 15, 20, 25, 30, 35, 40, 45, 50, 75, 100, 125, 150, 175, or 200 contiguous nucleotides, including any number between 5 and 200 not specifically recited herein, or up to the total number of nucleotides present in a full-length nucleotide sequence of this invention. The term "about", as used herein when referring to a measurable value such as a number of nucleotides, is meant to encompass variations of ±20%, ±10%, ±5%, ±1%, ±0.5%, or even ±0.1% of the specified amount.

The present invention further provides nucleic acids comprising promoters and promoter elements that direct expression of the nucleic acids of this invention according to the methods described herein. Bacterial promoters are identified as comprising various elements that facilitate ribosome binding on the messenger RNA in the region upstream of the first initiation codon of an open reading frame. These elements can include a hexamer region centered around nucleotide −10 and/or another hexamer centered around nucleotide −35, counting upstream from the first nucleotide of the initiation codon in negative numbers. An example of a −10 hexamer is TATAAT (SEQ ID NO: 109) and an example of a −35 hexamer is TTGACA ((SEQ ID NO: 110)e.g., as part of TCT-TGACAT) (SEQ ID NO: 111). These hexamers are recognized by the σ subunit of the RNA polymerase. There is also a spacer region connecting these two hexamers, the length of which is commonly conserved in most bacteria to be 17±5 base pairs. A TG motif upstream of the −10 hexamer is also commonly found in bacterial promoters, as well as an UP element, which is an AT-rich sequence upstream of the −35 hexamer (e.g., commonly around −40 to −60). This latter element is contacted by the C-terminal domain of the RNA polymerase α-subunit. Nonlimiting examples of a consensus sequence for an UP element of a bacterial promoter of this invention include nnAAA(A/T)(A/T)T(A/T)TTTTT nAAAAn (SEQ ID NO: 81),
NNAWWWWWTTTTTN (SEQ ID NO:82),
AAAAAARNR (SEQ ID NO:83),
NNAAAWWTWTTTTNNNAAANNN (SEQ ID NO:84),
AAAWWWTWTTTTNNNAAA (SEQ ID NO:85) and
GNAAAAATWTNTTNAAAAAAMNCTTGMA(N)$_{18}$TATAAT (SEQ ID NO:86), where W is A or T; M is A or C; R is A or G; and N is any base. Also included are complements of these sequences.

Thus, in certain embodiments, the present invention provides an isolated nucleic acid comprising from about 50 or 75 to about 100, 125, 150, 175, or 200 contiguous nucleotides, including any number between 50 and 200 not specifically recited herein (e.g., 60, 75, 96, 179, etc.), said nucleotides being located immediately upstream of the initiation codon of an open reading frame of this invention or upstream of a sequence corresponding to tRNA or rRNA, and numbered from between −1 to −200 in the nucleotide sequence, starting with the first nucleotide of the initiation codon or tRNA or rRNA sequence and numbering backwards in negative numbers, and further wherein said sequence of contiguous nucleotides comprises one or more of the promoter elements described herein and/or one or more nucleotide sequences having substantial similarity to a promoter element described herein and wherein said nucleic acid has promoter activity and/or potential promoter activity as detected according to methods standard in the art. (See, e.g., McCracken et al. (2000) "Analysis of promoter sequences from *Lactobacillus* and *Lactococcus* and their activity in several *Lactobacillus* species" *Arch. Microbiol.* 173:383-389; Estrem et al. (1998) "Identification of an UP element consensus sequence for bacterial promoters" *Proc. Natl. Acad. Sci. USA* 95:9761-9766; Ross et al. (1998) "*Escherichia coli* promoters with UP elements of different strengths: Modular structure of bacterial promoters" *J. Bacteriol.* 180:5375-5383; U.S. Pat. No. 6,605, 431 to Gourse et al., entitled "Promoter elements and methods of use"; and PCT publication number WO 2004/067772, published Aug. 12, 2004 and entitled "Method for the identification and isolation of strong bacterial promoters.") Each of these references is incorporated herein in its entirety for teachings regarding bacterial promoters and bacterial promoter elements and for additional examples of nucleotide sequences of bacterial promoter elements described herein.

The nucleic acid molecules of this invention comprising promoters and/or promoter elements have practical utility in the regulation of expression of homologous and/or heterologous nucleic acids, for example, to produce proteins for use in the various embodiments of this invention, as well as in any commercial application, such as, e.g., bacterial fermentation processes (e.g., production of insulin, blood coagulation proteins, etc.)

In some embodiments, the nucleic acid molecules of this invention comprise a regulatory element that modulates the ability of the promoter to activate transcription. Regulatory elements of the present invention are generally located within the approximately 0.2 kb of DNA 5' to the open reading frames of the *Lactobacillus acidophilus* NCFM genome. It will be apparent that other sequence fragments, longer or shorter than the foregoing sequence, or with minor additions, deletions, or substitutions made thereto, as those that result, for example from site-directed mutagenesis, as well as from synthetically derived sequences, are included within the present invention.

In one embodiment of the invention, a nucleic acid molecule of this invention comprises a regulatory element that is a catabolite response element (cre). By "catabolite response element," "cre sequence" or "cre-like sequence" is meant a cis-acting DNA sequence involved in catabolite repression. Expression of many catabolic enzymes in gram-positive bacteria is subject to repression by glucose and other rapidly metabolizable sources of carbon (Stewart (1993) *J. Cell. Biochem.* 51:25-28; Hueck and Hillen (1995) *Mol. Microbiol.* 143:147-148). This catabolite repression of such genes in gram-positive bacteria, notably *Bacillus subtilis*, is under the control of cis-acting nucleotide sequences described as cre sequences. These sequences contain a 2-fold axis of symmetry, are generally located in the region of promoter elements, can be present in multiples (e.g., pairs), and can vary in sequence location relative to the transcription start site for the transcription product under control of a given promoter element. Consensus nucleotide sequences for cre sequences are known in the art. Nonlimiting examples of consensus cre sequences include TGWAANCGNTNWCA (SEQ ID NO:87) (Weickert and Chambliss. 1990 *Proc. Natl. Acad. Sci. USA* 87:6238-6242); WWWWTGWAARCGYTWNCW-WWW (SEQ ID NO:88) (Zallieckas et al. (1998) *J. Bacteriol.* 180:6649-6654); and WWTGNAARCGNWWWCAWW (SEQ ID NO:89) (Miwa et al. (2000) *Nucleic Acids Res.* 28:1206-1210). Thus, in some embodiments, the present invention provides promoter sequences comprising one or more cre sequences. In certain embodiments, a promoter sequence of this invention can comprises one, two, or more than two cre sequences. Furthermore, the present invention provides fragments of the promoters of this invention, wherein the fragment comprises and/or consists essentially of a consensus cre sequence and/or a sequence that can be up to 70%, 75%, 80%, 85%, 90%, 95%, or 99% homologous to a consensus cre sequence.

The regulatory elements of this invention that enhance activation of transcription can increase nucleic acid transcription by at least 50%, 60%, 70%, 80%, 90%, 100%, 150%, 200%, 300% or more. The regulatory elements of this invention that suppress transcription can do so by at least 25%, 35%, 50%, 60%, 75%, 85%, 95% or more, up to and including 100%.

In other embodiments, the sequence of the nucleic acid encoding the regulatory element can correspond to a portion of the nucleotide sequence of a nucleic acid of this invention, such as the nucleotide sequences as set forth in SEQ ID NOS:1-80 or SEQ ID NO: 6, 72, or 73. Also included herein are fragments of a nucleotide sequence that is a regulatory element, wherein the fragment retains activity of the regulatory element. Nucleic acids of this invention that are fragments of a promoter or regulatory element can comprise, consist essentially of and/or consist of at least 15, 20, 25, 30, 35, 40, 45, 50, 75, 100, 125, 150, 175, or 200 contiguous nucleotides of the full-length sequence. Particular fragment lengths will depend upon the objective and will also vary depending upon the particular promoter or regulatory sequence.

The nucleotides of such fragments will usually comprise the TATA recognition sequence of the particular promoter sequence. Such fragments can be obtained by use of restriction enzymes to cleave the naturally occurring promoter nucleotide sequence disclosed herein; by synthesizing a nucleotide sequence from the naturally occurring sequence of the promoter nucleic acid sequence; or through the use of amplification protocols, such as PCR. See, for example, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis, are also encompassed in the present invention, as such variants are described herein.

Regulatory elements of the present invention can also include nucleic acids that regulate expression of nucleic acids and have a sequence that is substantially homologous to a nucleotide sequence comprising a regulatory element as disclosed herein, and particularly a nucleotide sequence comprising a regulatory element as disclosed herein as SEQ ID NOS:1-80.

Thus, a nucleic acid encoding a regulatory element of this invention includes a nucleic acid that is at least about 75%, 80%, 85%, 90%, 91%, 92%, 93%, 94%, 95%, 96%, 97%, 98% or 99% homologous to a nucleic acid encoding a regulatory element as described herein, and in particular a nucleic acid encoding a regulatory element and having the nucleotide sequence set forth herein as SEQ ID NOS: 1-80 or SEQ ID NOS: 6, 72, or 73. Regulatory elements from other species are also encompassed herein and include those that are at least about 75%, 80%, 85%, 90% or 95% homologous to a continuous segment of a regulatory element of the present invention, and which are capable of regulating the activation of transcription of nucleic acids.

As used herein, two nucleotide sequences are "substantially homologous" when they have at least about 50%, 60%, 70%, 80%, 85%, 90%, 91%, 92%, 93%, 94%, 95%, 96%, 97%, 98% or 99% homology with one another.

The term "homology" as used herein refers to a degree of similarity between two or more sequences. There can be partial homology or complete homology (i.e., identity). A partially homologous nucleic acid sequence that at least partially inhibits a complementary nucleic acid sequence from hybridizing to a target nucleic acid is referred to using the finctional term "substantially homologous." The inhibition of hybridization to the target sequence can be examined using a hybridization assay (Southern or Northern blot, solution hybridization and the like) under conditions of varying stringency, as that term is known in the art. A substantially homologous sequence or hybridization probe will compete for and inhibit the binding of a completely complementary sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding can be tested by the use of a second target sequence, which lacks even a partial degree of complementarity (e.g., less than about 30%). In the absence of non-specific binding, the probe will not hybridize to the second non-complementary target sequence.

Alternatively stated, in particular embodiments, nucleic acids that hybridize under the conditions described herein to the complement of the sequences specifically disclosed herein can also be used according to the present invention. The term "hybridization" as used herein refers to any process by which a first strand of nucleic acid binds with a second strand of nucleic acid through base pairing.

The term "stringent" as used here refers to hybridization conditions that are commonly understood in the art to define the conditions of the hybridization procedure. Stringency conditions can be low, high or medium, as those terms are commonly know in the art and well recognized by one of ordinary skill. High stringency hybridization conditions that will permit a complementary nucleotide sequence to hybridize to a nucleotide sequence as given herein are well known in the art. As one example, hybridization of such sequences to the nucleic acid molecules disclosed herein can be carried out in 25% formamide, 5×SSC, 5×Denhardt's solution and 5% dextran sulfate at 42° C., with wash conditions of 25% formamide, 5×SSC and 0.1% SDS at 42° C., to allow hybridization of sequences of about 60% homology. Another example includes hybridization conditions of 6×SSC, 0.1% SDS at about 45° C., followed by wash conditions of 0.2×SSC, 0.1% SDS at 50-65° C. Another example of stringent conditions is represented by a wash stringency of 0.3M NaCl, 0.03M sodium citrate and 0.1% SDS at 60-70° C. using a standard hybridization assay (see Sambrook et al., eds., *Molecular Cloning: A Laboratory Manual* 2d ed. (Cold Spring Harbor, N.Y. 1989, the entire contents of which are incorporated by reference herein). In various embodiments, stringent conditions can include, for example, highly stringent (i.e., high stringency) conditions (e.g., hybridization to filter-bound DNA in 0.5 M NaHPO$_4$, 7% sodium dodecyl sulfate (SDS) and 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

As is known in the art, a number of different programs can be used to identify whether a nucleic acid or amino acid has homology (e.g., sequence identity or similarity) to a known sequence. Homology can be determined using standard techniques known in the art, including, but not limited to, the local sequence identity algorithm of Smith and Waterman (1981) *Adv. Appl. Math.* 2:482, the sequence identity alignment algorithm of Needleman and Wunsch (1970) *J. Mol. Biol.* 48:443, the search for similarity method of Pearson and Lipman (1988) *Proc. Natl. Acad. Sci. USA* 85:2444, computerized implementations of these algorithms (GAP, BESTFIT, FASTA, and TFASTA in the Wisconsin Genetics Software Package, Genetics Computer Group, 575 Science Drive, Madison, Wis.) and/or the Best Fit sequence program described by Devereux et al. (1984) *Nuc. Acid Res.* 12:387-395, preferably using the default settings, or by inspection.

An example of a useful algorithm is PILEUP, which creates a multiple sequence alignment from a group of related sequences using progressive, pairwise alignments. It can also plot a tree showing the clustering relationships used to create the alignment. PILEUP uses a simplification of the progressive alignment method of Feng and Doolittle (1987) *J. Mol. Evol.* 35:351-360; which is similar to that described by Higgins and Sharp (1989) *CABIOS* 5:151-153.

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program that was obtained from Altschul et al., *Methods in Enzymology,* 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity. An additional useful algorithm is gapped BLAST as reported by Altschul et al. *Nucleic Acids Res.* 25, 3389-3402.

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix or any equivalent program thereof. Other equivalent programs can also be used. By "equivalent program" is meant any sequence comparison program that, for any two sequences in question, generates an alignment having identical nucleotide or amino acid residue matches and an identical percent sequence identity when compared to the corresponding alignment generated by GAP Version 10.

In addition, for sequences that contain either more or fewer nucleotides than the nucleic acids disclosed herein, it is understood that in one embodiment, the percentage of sequence homology will be determined based on the number of identical nucleotides in relation to the total number of nucleotide bases. Thus, for example, sequence homology of sequences shorter than a sequence specifically disclosed herein can be determined using the number of nucleotide bases in the shorter sequence, in one embodiment. In percent homology calculations, relative weight is not assigned to various manifestations of sequence variation, such as, insertions, deletions, substitutions, etc.

The present invention also provides a recombinant nucleic acid comprising a nucleic acid encoding a regulatory element operably associated with a nucleic acid of interest. The nucleic acid encoding the regulatory element is operably associated with the nucleic acid of interest such that the regulatory element can modulate transcription of the nucleic acid of interest as directed by a nucleic acid having promoter activity. Typically, the nucleic acid encoding the regulatory element and/or the nucleic acid having promoter activity will be located 5' to the nucleic acid of interest, but either or both can also be located 3' to the nucleic acid of interest as long as they are operably associated therewith. There are no particular upper or lower limits as to the distance between the nucleic acid encoding the regulatory element and/or the nucleic acid having promoter activity and the nucleic acid of interest, as long as the nucleic acids are operably associated with one another.

The nucleic acid molecules of the present invention can also be included in vectors, which in some embodiments can be expression vectors. A vector of this invention can include one or more regulatory sequences to direct the expression of nucleic acids to which they are operably linked or operatively associated. The term "regulatory sequence" is meant to include, but is not limited to, promoters, operators, enhancers, transcriptional terminators, and/or other expression control elements such as translational control sequences (e.g., Shine-Dalgarno consensus sequence, initiation and termination codons). These regulatory sequences will differ, for example, depending on the cell into which the vector is to be introduced.

The vectors of this invention can be autonomously replicated in a cell (episomal vectors), or they can be integrated into the genome of a cell, and replicated along with the cell's genome (non-episomal vectors). Integrating vectors in prokaryotes typically contain at least one sequence homologous to the bacterial chromosome that allows for recombination to occur between homologous nucleic acid in the vector and the bacterial chromosome. Integrating vectors can also comprise bacteriophage or transposon sequences. Episomal vectors, or plasmids are typically circular double-stranded nucleic acid loops into which additional nucleic acid sequences can be ligated.

The vectors of this invention can comprise a nucleic acid of this invention in a form suitable for expression of the nucleic acid in a cell, which can be a eukaryotic or prokaryotic cell. It will be appreciated by those skilled in the art that the design of the vector can depend on such factors as the choice of the cell to be transformed, the level of expression of nucleic acid and/or production of protein desired, etc.

A promoter of this invention can be regulated in its transcription activity in various ways, as are known to one of ordinary skill in the art. For example, regulation can be achieved in some embodiments when a gene activator protein sequence is present. When present, such a sequence is usually proximal (5') to the RNA polymerase binding sequence.

An example of a gene activator protein is the catabolite activator protein (CAP), which helps initiate transcription of the lac operon in *Escherichia coli* (Raibaud et al. (1984) *Annu. Rev. Genet.* 18:173). Regulated expression can therefore be either positive or negative, thereby either enhancing or reducing transcription. Other examples of positive and negative regulatory elements are well known in the art. Various other promoters besides the promoters of this invention can be included in the vectors of this invention. Examples of such other promoters include, but are not limited to, a T7/LacO hybrid promoter, a trp promoter, a T7 promoter, a lac promoter, and a bacteriophage lambda promoter. Such other promoters can be constitutively active or inducible.

It is also contemplated that the promoters of the present invention can be combined with synthetic promoters that do not occur in nature, and/or such synthetic promoters can be present in a vector of this invention, in combination with a promoter of this invention. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac (Amann et al. (1983) *Gene* 25:167; de Boer et al. (1983) *Proc. Natl. Acad. Sci.* 80:21) and trc (Brosius et al. (1985) *J. Biol. Chem.* 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG).

Furthermore, a vector of this invention can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some nucleic acids in prokaryotes. The bacteriophage T7 RNA polymerase/promoter system is an example of a coupled promoter system (Studier et al. (1986) *J. Mol. Biol.* 189:113; Tabor et al. (1985) *Proc. Natl. Acad. Sci.* 82:1074). In addition, a hybrid promoter is also provided, which can comprise a bacteriophage promoter and a promoter or active region of a promoter of the present invention.

The vector of this invention can additionally comprise a nucleic acid sequence encoding a repressor (or inducer) for the promoter provided in the vector. For example, an inducible vector of the present invention may regulate transcription from the Lac operator (LacO) by expressing the gene encoding the Lacd repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., λCI857, rendering λpL thermo-inducible, or λCI+, rendering λpL chemo-inducible) may be employed.

In addition to a functioning promoter sequence, an efficient ribosome-binding site is also useful for the expression of nucleic acid sequences from the vectors of this invention. In prokaryotes, the ribosome binding site is called the Shine-Dalgarno (SD) sequence and includes an initiation codon (ATG) and a sequence 3-9 nucleotides in length located 3-11 nucleotides upstream of the initiation codon (Shine et al. (1975) *Nature* 254:34). The SD sequence is thought to promote binding of mRNA to the ribosome by the pairing of bases between the SD sequence and the 3' end of bacterial 16S rRNA (Steitz et al. (1979) "Genetic Signals and Nucleotide Sequences in Messenger RNA," in *Biological Regulation and Development: Gene Expression* (ed. R. F. Goldberger, Plenum Press, NY).

The nucleic acid of interest provided in this invention can encode a peptide and/or polypeptides that can be secreted from the cell. Such a peptide or polypeptide is produced by creating chimeric nucleic acid molecules that encode a protein or peptide comprising a signal peptide sequence that provides for secretion of polypeptides in bacteria (U.S. Pat. No. 4,336,336). The signal sequence typically encodes a signal peptide comprised of hydrophobic amino acids that direct the secretion of the protein or peptide from the cell. The protein or peptide is either secreted/exported into the growth medium (gram-positive bacteria) or into the periplasmic space, located between the inner and outer membrane of the cell (gram-negative bacteria). In some embodiments, processing sites can be introduced, where cleavage can occur, either in vivo or in vitro, located between the signal peptide sequence and the peptide or polypeptide.

Nucleic acids encoding suitable signal sequences can be derived from genes encoding secreted bacterial proteins, such as the *E. coli* outer membrane protein gene (ompA) (Masui et al. (1983) *FEBS Lett.* 151(1):159-164; Ghrayeb et al. (1984) *EMBO J.* 3:2437-2442) and the *E. coli* alkaline phosphatase signal sequence (phoA) (Oka et al. (1985) *Proc. Natl. Acad. Sci.* 82:7212). Other prokaryotic signal sequences can include, for example, the signal sequence from penicillinase, Ipp, or heat stable enterotoxin II leaders.

The vectors of this invention can further comprise a transcription termination sequence. Typically, transcription termination sequences recognized by bacteria are regulatory regions located 3' to the translation stop codon and thus, together with the promoter, flank the coding sequence of a nucleic acid of interest. These sequences direct the transcription of a mRNA that can be translated into the polypeptide or peptide or other gene product encoded by the nucleic acid of interest. Transcription termination sequences frequently include nucleic acid sequences (of about 50 nucleotides) that are capable of forming stem loop structures that aid in terminating transcription. Examples include transcription termination sequences derived from genes with strong promoters, such as the trp gene in *E. coli* as well as other biosynthetic genes.

The vectors of this invention can also comprise at least one, and typically a plurality of restriction sites for insertion of the nucleic acid(s) of interest so that it is under transcriptional regulation of the regulatory regions. Selectable marker genes that ensure maintenance of the vector in the cell can also be included in the vector. Examples of selectable markers include, but are not limited to, those that confer resistance to drugs such as ampicillin, chloramphenicol, erythromycin, kanamycin (neomycin), and tetracycline (Davies et al. (1978) *Annu. Rev. Microbiol.* 32:469). Selectable markers can also allow a cell to grow on minimal medium, or in the presence of toxic metabolites and can include biosynthetic genes, such as those in the histidine, tryptophan, and leucine biosynthetic pathways.

Regulatory regions present in the vector of this invention can be native (homologous), or foreign (heterologous) to the host cell and/or to the promoter and/or nucleic acid of interest of this invention. The regulatory regions can also be natural or synthetic. By "operably linked" is meant that the nucleotide sequence of interest is linked to the regulatory sequence(s) such that expression of the nucleotide sequence is allowed (e.g., in an in vitro transcription/translation system or in a cell when the vector is introduced into the cell). As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. In another example, where the region is "foreign" or "heterologous" to the host cell, it can mean that the region is not found in the native cell into which the region is introduced. Alternatively, where the region is "foreign" or "heterologous" to the promoter and/or nucleic acid of interest of the invention, it is meant that the region is not the native or naturally occurring region for the operably linked promoter and/or nucleic acid of interest of the invention. For example, the regulatory region can be derived from phage. While it may be preferable to express the nucleic acid of interest using heterologous regulatory regions, native regions can also be used. Such constructs would be expected in some cases to alter expression levels of nucleic acids in the host cell. Thus, the phenotype of the host cell could be altered.

In preparing the vector of this invention, the various nucleotide sequences can be manipulated, so as to position the promoter and/or nucleic acid of interest and/or other regulatory elements in the proper orientation in the vector and, as appropriate, in the proper reading frame. Toward this end, adapters or linkers can be employed to join the nucleotide sequences or other manipulations can be employed to provide for convenient restriction sites, removal of superfluous nucleic acid, removal or addition of restriction sites, and the like as would be well known in the art. For this purpose, in vitro mutagenesis, primer repair, restriction, annealing, resubstitutions, e.g., transitions and transversions, can be employed, according to art-known protocols.

The invention further provides a vector comprising a nucleic acid molecule of this invention cloned into the vector in an antisense orientation. That is, the nucleic acid is operably linked to a promoter of this invention in a manner that allows for expression (by transcription of the nucleic acid molecule) of an RNA molecule that is antisense to a messenger RNA in a cell into which the vector is introduced. The promoter operably linked to the nucleic acid cloned in the antisense orientation can be chosen to direct the continuous or inducible expression of the antisense RNA molecule. In some embodiments, the antisense vector can be in the form of a recombinant plasmid or phagemid in which antisense nucleic acids are produced under the control of a high efficiency regulatory region comprising a promoter of this invention, the activity of which can be determined by the cell type into which the vector is introduced. For a discussion of the regulation of protein production in a cell using antisense sequences, see Weintraub et al. (1986) *Reviews—Trends in Genetics*, Vol. 1(1).

In some embodiments of the present invention, the production of bacteria containing the recombinant nucleic acid sequences of this invention, the preparation of starter cultures of such bacteria, and methods of fermenting substrates, particularly food substrates such as milk, can be carried out in accordance with known techniques. (See, for example, Gilliland, S. E. (ed) *Bacterial Starter Cultures for Food*, CRC Press, 1985, 205pp.; Read, G. (Ed.). *Prescott and Dunn's Industrial Microbiology*, 4$^{th}$ Ed. AVI Publishing Company, Inc. 1982, 883 pp.; Peppler, J. J. and Perlman, D. (Eds.). *Microbiol Technology: Volume II, Fermentation Technology*, Academic Press, 1979, 536 pp.)

By "fermenting" is meant the energy-yielding, metabolic breakdown of organic compounds by microorganisms that generally proceeds under anaerobic conditions and with the production of organic acids (lactate, acetate) as major end products and minor end products, such as ethanol, carbon dioxide and diacetyl.

By "introducing" as it pertains to nucleic acid molecules is meant introduction into cells, such as prokaryotic cells via conventional transformation or transfection techniques, or by phage-mediated infection. As used herein, the terms "transformation," "transduction," "conjugation," and "protoplast fusion" are meant to refer to a variety of art-recognized techniques for introducing foreign nucleic acid (e.g., DNA) into a eukaryotic or prokaryotic host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals. By "introducing" or "delivering" as it pertains to cells such as bacterial cells of the invention, is meant introduction into a subject by ingestion, topical application, nasal, urogenital, suppository, and/or oral application of the microorganism.

Bacterial cells of this invention are cultured in suitable medium, as described generally in Sambrook et al. (1989) *Molecular Cloning, A Laboratory Manual* (2d ed., Cold Spring Harbor Laboratory Press, Plainview, N.Y.). The nucleic acids and/or vectors of this invention can be used to transform cells, which can be in vitro or in vivo. Thus, the present invention further provides a method of transforming a cell, comprising introducing a nucleic acid and/or vector of this invention into the cell according to well-known methods for transforming cells, as described herein. The cell of this invention can be a prokaryotic cell or a eukaryotic cell.

As indicated herein, in some embodiments, the nucleic acid and/or vector of this invention can be introduced into a bacterial cell and the bacterial cell can be administered to a subject that can safely receive the bacterial cell.

In embodiments wherein the cell of this invention is in vivo, the nucleic acid and/or vector of this invention can be delivered to or introduced into a subject comprising the cell.

A subject of this invention can be any animal having cells that can be transformed by the nucleic acids and/or vectors of this invention and/or having the capability of receiving transformed bacterial cells of this invention. The animal can be a mammal, an avian species, a reptile, or any other type of animal. In some embodiments, the animal is a mammal, which can be a domesticated animal (e.g., cat, dog, horse, cow, goat), a human or a non-human primate.

EXPERIMENTAL

Microarray Construction. A whole genome DNA microarray based on the PCR products of predicted ORFs from the *L. acidophilus* genome was used for global gene expression analysis. PCR primers for 1,966 genes were designed using GAMOLA software (Altermann and Klaenhammer 2003 "GAMOLA: a new local solution for sequence annotation and analyzing draft and finished prokaryotic genomes" *OMICS* 7:161-169) and purchased from Qiagen Operon (Alameda, Calif.). Total genomic DNA from *L. acidophilus* NCFM was used as a template for 96-well PCR amplifications. To amplify gene-specific PCR products, a 100 µl reaction mix contained: 1 µl *L. acidophilus* DNA (100 ng/ml), 10 µl specific primer pairs (10 µM), 0.5 µl of dNTP mix (10 mM), 10 µl PCR buffer (10×), and 1 µl Taq DNA polymerase (5 U/µl [Roche Molecular Biochemicals]). The following PCR protocol was used: an initial denaturation step for 5 min at 94° C. followed by 40 cycles of denaturation at 94° C. for 15 sec, annealing at 50° C. for 30 sec and polymerization at 72° C. for 45 sec. Approximately 95% of open reading frames (ORFs) produced a unique PCR product between 100-800 bp. The size of fragments was confirmed by electrophoresis in 1% agarose gels. DNA from 96-well plates was purified using the Qiagen Purification Kit. In general, the total quantity of each PCR product was greater than 1 µg.

The purified PCR fragments were spotted three times in a random pattern on glass slides (Coming, Acton, Mass.) using the Affymetrix® 417™ Arrayer at the NCSU Genome Research Laboratory. To prevent carry-over contaminations, pins were washed between uses in different wells. Humidity was controlled at 50-55% during printing. DNA was cross-linked to the surface of the slide by UV (300 mJ) and posterior incubation of the slides for 2 h at 80° C. The reliability of the microarray data was assessed by hybridization of two cDNA samples prepared from the same total RNA, labeled with Cy3 and Cy5. Hybridization data revealed a linear correlation in the relative expression level of 98.6% of 5685 spots (each gene by triplicate) with no more than a two-fold change.

Culture treatment/growth conditions. The strain used in this study is *L. acidophilus* NCFM (NCK56) (Altermann et al. 2004 "Identification and phenotypic characterization of the cell-division protein CdpA" *Gene* 342:189-197). For the studies examining growth on varying carbohydrates, cultures were propagated at 37° C., aerobically in MRS broth (Difco). A semi-synthetic medium consisted of: 1% bactopeptone (w/v) (Difco), 0.5% yeast extract (w/v) (Difco), 0.2% dipotassium phosphate (w/v) (Fisher), 0.5% sodium acetate (w/v) (Fisher), 0.2% ammonium citrate (w/v) (Sigma), 0.02% magnesium sulfate (w/v) (Fisher), 0.005% manganese sulfate (w/v) (Fisher), 0.1% Tween 80 (v/v) (Sigma), 0.003% bromocresol purple (v/v) (Fisher) and 1% sugar (w/v). The carbohydrates added were either: glucose (dextrose) (Sigma), fructose (Sigma), sucrose (Sigma), FOS (raftilose P95) (Orafti), raffinose (Sigma), lactose (Fisher), galactose (Sigma) or trehalose (Sigma). Without carbohydrate supplementation, the semi-synthetic medium was unable to sustain bacterial growth. Cells underwent at least five passages on each sugar prior to RNA isolation, to minimize carryover between substrates (Chhabra et al. "Carbohydrate-induced differential gene expression patterns in the hyperthermophilic bacterium *Thermotoga maritima*." *J Biol Chem*. (2003) 278(9):7540-52). In the final culture, *L. acidophilus* cells were inoculated into semi-synthetic medium supplemented with 1% (w/v) select sugars and propagated to mid-log phase (OD$_{600\ nm}$~0.6). Cells were harvested by centrifugation (2 minutes, 14,000 rpm) and immediately cooled on ice prior to RNA isolation.

For studies on cells exposed to varying stresses, *L. acidophilus* NCFM was grown from a 2% inoculum in MRS broth to OD$_{600}$ of 0.25-0.3 (pH>5.8). Cultures were centrifuged and resuspended in the same volume of MRS adjusted to pH 5.5 or 4.5 with lactate, MRS containing 5% bile, 70 mM ammonium oxalate or 15% ethanol (v/v) and incubated at 37° C. for 30 min. After incubation, cells were harvested by centrifugation and frozen immediately in a dry ice/ethanol bath.

Measurement of GUS activity. *L. acidophilus* cultures were grown to mid-log phase (OD=0.5) in MRS, harvested and resuspended in SSM+1% carbohydrate, incubated at 37° C. for up to three hours and then the cells were harvested by centrifugation. Cell pellets were resuspended in 1 mL GUS assay buffer (100 mM sodium phosphate, 2.5 mM EDTA, pH 6.0) and transferred to tubes containing glass beads for bead beating (3×1 min with 1 min rest on ice between cycles). Cell debris was pelleted and protein concentration was determined via the Bradford method. GUS activity for 1 mg of protein was then determined spectrophometrically using MUG as the substrate under the following conditions: 100 mM Na-phosphate, 2.5 mM EDTA 1 mM MUG, pH 6.0 at 37° C. Fluorescence was measured using a Fluostar Optima microplate reader with excitation at 355 nm and emission at 460 nm. A standard curve for 4-methylumbelliferone (10 to 600 nM) in GUS lysis buffer also was generated, and GUS activity was expressed in pmol 4-methylumbelliferone produced per minute per milligram of protein. Such methods were carried out to obtain the data appearing in Table 1 and FIGS. 2 and 3.

RNA isolation. Total RNA was isolated using TRIzol (GibcoBRL) by following the manufacturer's instructions. Pellets were resuspended in TRIZOL, by vortexing and underwent five cycles of 1 min bead beating and 1 min on ice. Nucleic acids were purified using three chloroform (Fisher) extractions, and precipitated using isopropanol (Fisher) and centrifugation for 10 min at 12,000 rpm. The RNA pellet was washed with 70% ethanol (AAPER Alcohol and Chemical co.) and resuspended into DEPC-(Sigma) treated water. RNA samples were treated with DNAse I according to the manufacturer's recommendations (Boehringer Mannheim).

cDNA target preparation and microarray hybridization. For each hybridization, RNA samples (25 µg of DNase treated) were amino-allyl labeled by reverse transcription using random hexamers (Invitrogen Life Technologies, Carlsbad, Calif.) as primers, in the presence of amino-allyl dUTP (Sigma, Town, state), by a SuperScript II reverse transcriptase (Invitrogen Life Technologies, Carlsbad, Calif.), as described previously (Hedge et al. 2000 "A concise guide to cDNA microarray analysis" *Biotechniques* 29(3):548-50; Azcarate-Peril et al. 2004 "Identification and inactivation of genetic loci involved with *Lactobacillus acidophilus* acid tolerance" *Appl. Environ. Microbiol.* 70:5315-5322). Labeled cDNA samples were subsequently coupled with either Cy3 or Cy5 N-hydroxysuccinimidyl-dyes (Amersham Biosciences Corp., Piscataway, N.J.), and purified using a PCR purification kit (Qiagen). The resulting samples were hybridized onto microarray slides and further processed as described previously (Azcarate-Peril et al. 2004), according to the TIGR protocol (Hedge et al. 2000). Briefly, combined Cy5- and Cy3-labeled cDNA probes were hybridized to the arrays for 16 h at 42° C. After hybridization, the slides were washed twice in low stringency buffer (1×SSC containing 0.2% SDS) for 5 min each. The first wash was performed at 42° C. and the second one at room temperature. Subsequently, the slides were washed in a high stringency buffer (0.1×SSC containing 0.2% SDS, for 5 min at room temperature) and finally in 0.1×SSC (2 washes of 2.5 min each at room temperature).

For stress microarray hybridizations a Reference Sample design was used, where each sample was compared using a dye swap to a common reference sample (early log-phase *L. acidophilus* cultures resuspended in fresh MRS [pH ~6.8]), so that experiments could be extended to assay several samples collected over a period of time, all comparisons were made with equal efficiency and every new sample in a reference experiment was managed in the same way.

Hybridizations in sugar experiments were performed according to a single Round-Robin design, so that all possible direct pair-wise comparisons were conducted (See Figure below). With 8 different sugars, a total of 28 hybridizations were performed. Each treatment was labeled 7 times, and every-other treatment was labeled with either Cy3 or Cy5, 4 and 3 times, alternatively.

Microarray data collection and analysis. Microarray images were acquired using a Scanarray 4000 Microarray Scanner (Packard Biochip Bioscience, Mass.). Signal fluorescence, including spot and background intensities were subsequently quantified and assigned to genomic ORFs using Quantarray 3.0 (Packard BioChip Technologies LLC, Billerica, Mass.).

Data normalization and gene expression analysis. Immediately after washing of the arrays, fluorescence intensities were acquired at 10 µm resolution using a ScanArray 4000 Microarray Scanner (Packard Biochip BioScience, Biochip Technologies LLC, Mass.) and stored as TIFF images. Signal intensities were quantified, the background was subtracted and data were normalized using the QuantArray 3.0 software package (Perkin Elmer). Two slides (each containing triplicate arrays) were hybridized reciprocally to Cy3- and Cy5-labeled probes per experiment (dye swap). Spots were analyzed by adaptive quantitation. Data were median normalized. When the local background intensity was higher than the spot signal (negative values) no data were considered for those spots. The median of the six ratios per gene was recorded. The ratio between the average absolute pixel values for the replicated spots of each gene with and without treatment represented the fold change in gene expression. All genes belonging to a potential operon were considered for analysis if at least one gene of the operon showed significant expression changes and the remaining genes showed trends toward that expression. Confidence intervals and P values on the fold change were also calculated with the use of a two-sample t test. P values of 0.05 or less were considered significant.

Table 3 provides the nucleotide sequence of promoters as identified from the sequencing and characterization of the genome of *Lactobacillus acidophilus* NCFM. The sequences are shown to be identified by the open reading frame with which the promoter sequence is associated in the genome and the expression conditions studied, with results described. A predicted ribosome binding site (RBS) is underlined for each promoter sequence in the figure. The expression characteristics of various genes and their corresponding ORF# under control of the promoters of this invention are shown under each sequence appearing in Table 3. Genes that are "consistently highly", the genes expressed by promoters responsive to the "stress" conditions described herein, and the genes that are expressed under the control of the promoters responsive to the sugars described herein are summarized in Table 3.

Table 4 provides a listing of all promoters shown in Table 3 that have cre elements as described herein, as well as a summary of the number of promoters described in Table 3 and the number of genes that are expressed by the various promoters classified as "high" (the genes are highly expressed), "stress" (the genes are expressed by activation of the promoter or their expression is repressed by exposure to a stress response (e.g., change in pH, exposure to bile, oxalate or ethanol alone or in various combinations) and "sugar" [the genes are expressed in the presence of sugars such as glucose (glu), fructose (fru), sucrose (suc), trehalose (tre), fructooligosaccharide (fos), raffinose (raf), lactose (lac) and galactose (gal)].

As shown in Table 4, ORFs 1467-1468 are induced in the presence of lactose and galactose. SEQ ID NO:79 comprises the nucleotide sequence of the promoter for ORFs 1467-1468 from LacL up through the cre sequences that are upstream of LacR. SEQ ID NO:80 also comprises the nucleotide sequence of the promoter for ORFs 1467-1468, but further includes both the sequences of LacR and the sequences in front of LacR. Accordingly, SEQ ID NO:80 includes the repressor sequence. Our data has demonstrated that SEQ ID NO:80 allows for the tight transcriptional control (promoter off) in the absence of the inducing sugar.

Table 5 lists the genes (designated by ORF#, see Table 3) expressed by the promoters responsive to the stress conditions described herein and the particular conditions for induction of their expression (pH, bile, oxalate, ethanol). Numbers and shades represent induction of expression levels from high (15) to low (2). The conditions for exposure were log phase cells in MRS broth (OD600 nm of 0.3) for 30 mins. FIG. 1 is a schematic of the experimental design of the microarray assays described herein.

Figure 2:
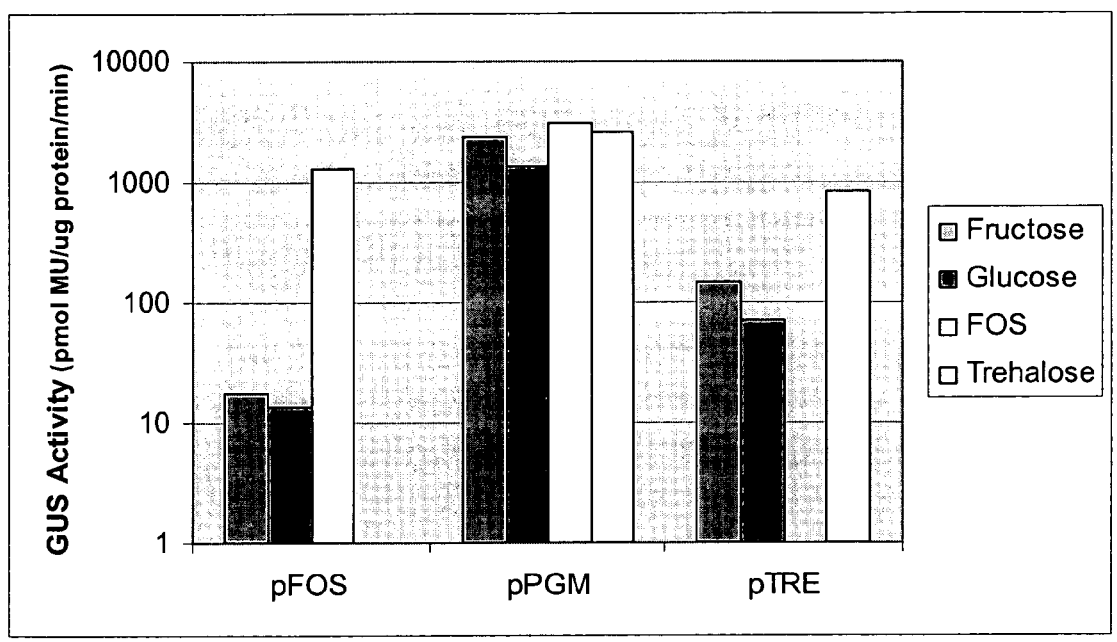
FIG. 2 provides an overview of expression data from a GUS reporter gene assay. pFOS refers to the 502_sugar promoter sequence set forth in SEQ ID NO: 72; pTRE refers to the 1012_sugar promoter sequence set forth in SEQ ID NO:73; and, pPGM refers to the 185_high promoter set forth in SEQ ID NO:6.

FIG. 2 is an overview of the expression data from GUS (reporter gene) assays that were carried out, investigating gene expression in constructs including three promoters disclosed herein, as examples. pFOS includes the sequence of the 502_sugars promoter (SEQ ID NO:72) ; pTRE includes the sequence of the 1012_sugars promoter (SEQ ID NO:73); pPGM includes the sequence of the 185_high promoter (SEQ ID NO:6). This covers examples for both the "highly expressed genes category" (PGM-185) and the "inducible by carbohydrates category (FOS-502 and TRE-1012). The graph shows that (1) (foremost left) in the presence of FOS as a substrate, the FOS promoter is inducible (when compared to glucose and fructose); (2) (center) the PGM promoter provides high gene expression regardless of the conditions tested; (3) (foremost right) the TRE promoter is inducible in the presence of trehalose as as substrate (when compared to FOS and fructose).

Table 1 provides a summary table of the data provided in FIG. 2.

TABLE 1

GUS Activity (pmol MU/ug protein/min)

| Carbohydrate | pFOS | pPGM | pTRE |
|---|---|---|---|
| MRS | — | 1662.40 | — |
| Fructose | 17.94 | 2428.10 | 147.61 |
| Glucose | 13.83 | 1359.90 | 69.91 |
| FOS | 1299.60 | 3105.30 | — |
| Trehalose | — | 2554.00 | 833.10 |

Figure 3:
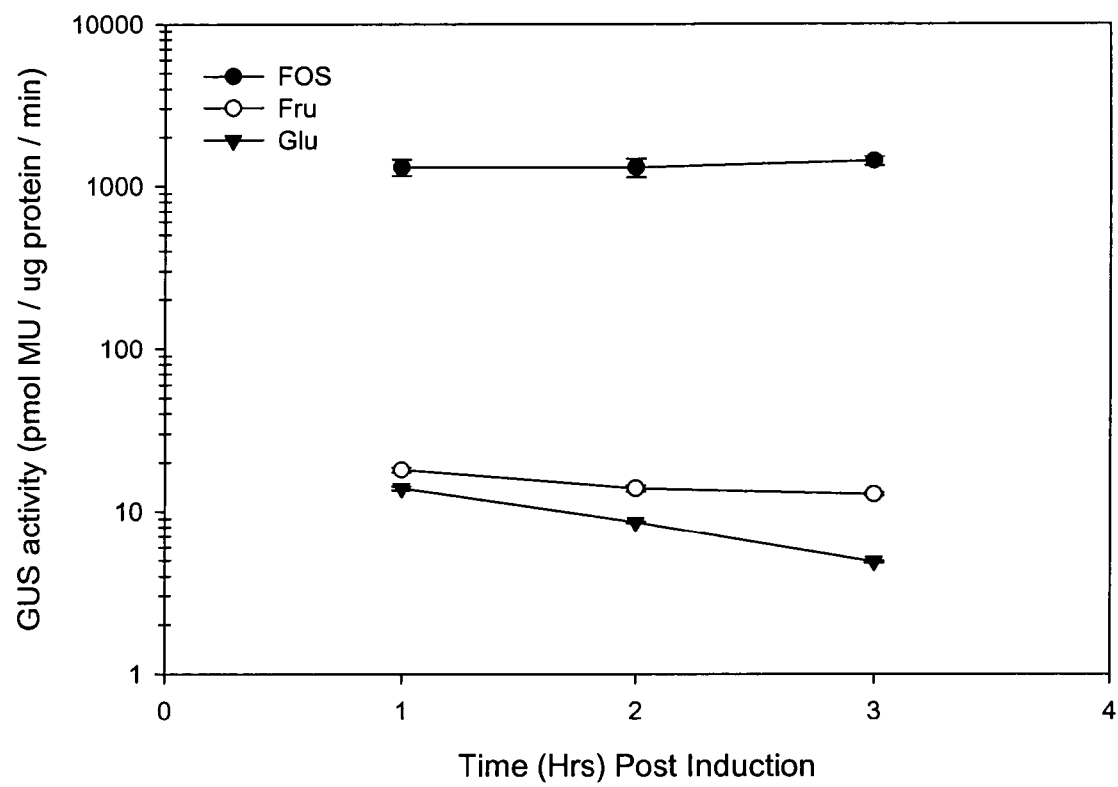
FIG. 3 is a detailed representation (through time) of the pFOS (promoter 502_sugars) (SEQ ID NO:72) data. It shows that this promoter is inducible in the presence of FOS when compared to glucose and fructose.
Figure 4:
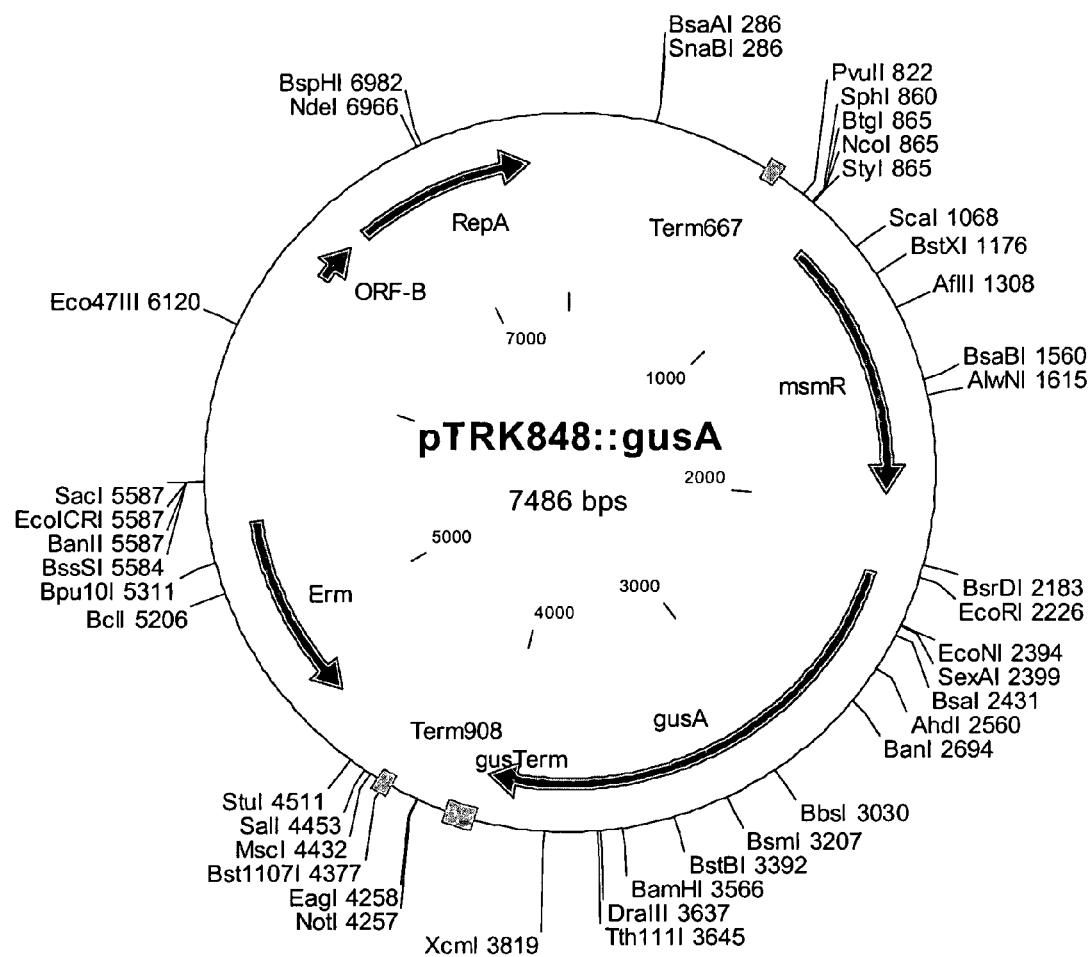
FIG. 4 provides a non-limiting schematic of an expression vector for the pFOS promoter (SEQ ID NO:72).
Figure 5:
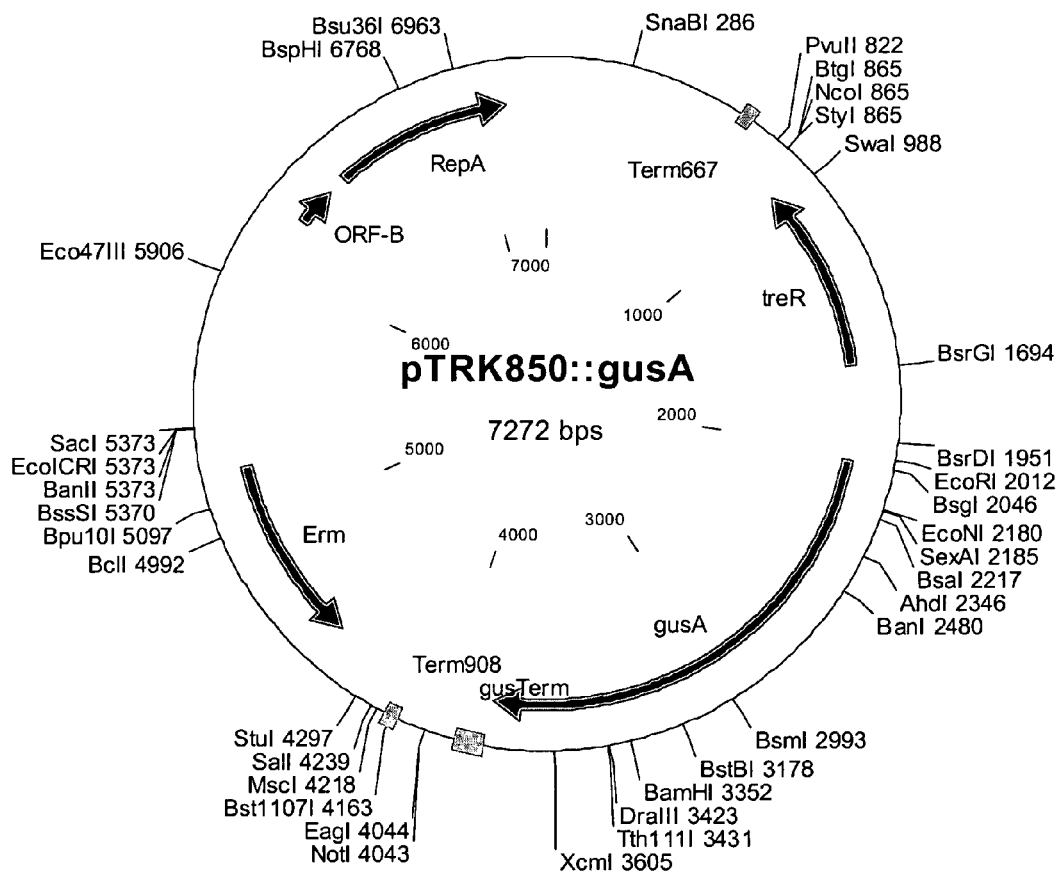
FIG. 5 provides a non-limiting schematic of an expression vector for the pTRE promoter (SEQ ID NO:73).
Figure 6:
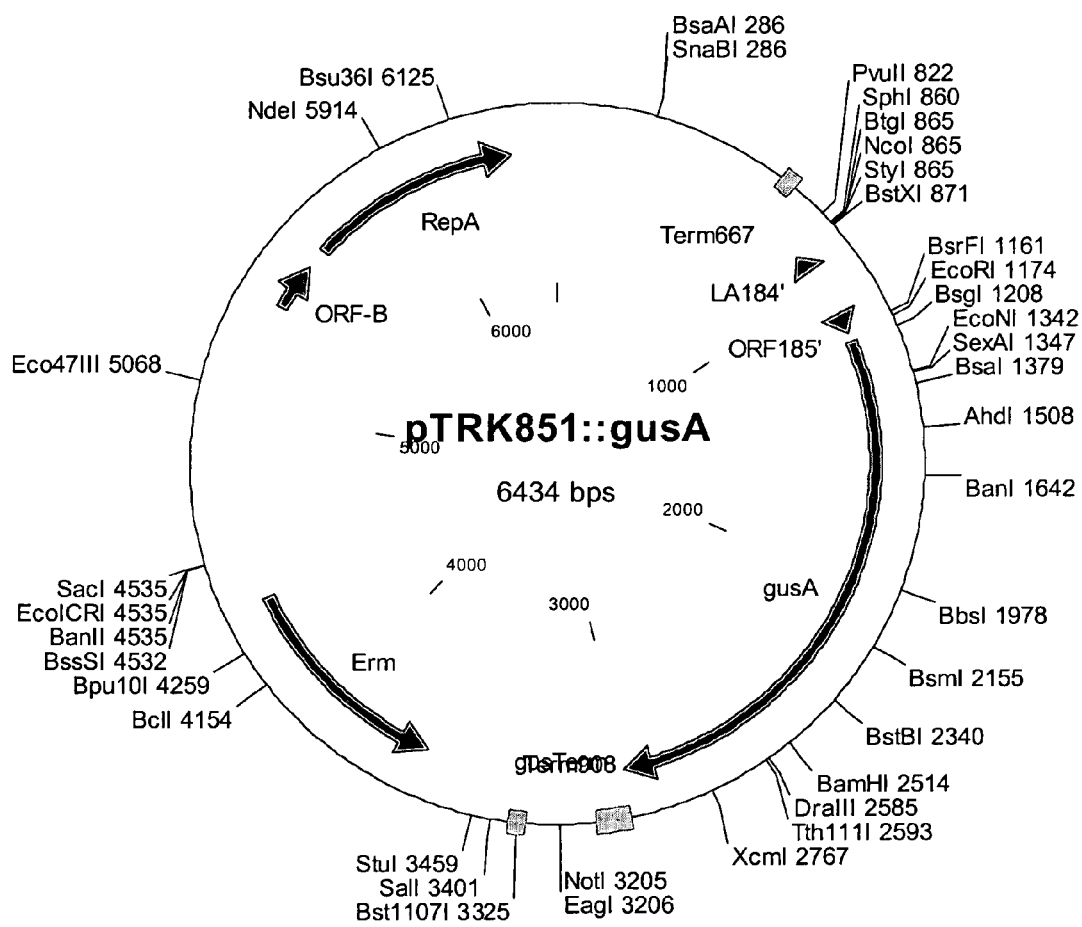
FIG. 6 provides a non-limiting schematic of an expression vector for the pPGM promoter (SEQ ID NO:6).

FIG. 3 is a detailed representation (through time) of the pFOS (promoter 502_sugars) ( SEQ ID NO: 72) data. It shows that this promoter is inducible in the presence of FOS when compared to glucose and fructose.

TABLE 2

Promoters of the present invention and associated genes.

| SEQ ID NO | ORF#(s)[a] | Gene(s) controlled | Expression/Response |
|---|---|---|---|
| 1 | 8 | single stranded DNA binding protein | High |
| 2 | 55 | D-lactate dehydrogenase | High |
| 3 | 151-154 | alkyl phosphonate ABC transporter | High |

TABLE 2-continued

Promoters of the present invention and associated genes.

| SEQ ID NO | ORF#(s)[a] | Gene(s) controlled | Expression/Response |
|---|---|---|---|
| 4 | 169 | s-layer protein (slp-A) | High |
| 5 | 175 | s-layer protein (slp-B) | High |
| 6 | 185 | phosphoglycerate mutase | High |
| 7 | 271 | L-lactate dehydrogenase | High |
| 8 | 278 | FtsH cell division protein | High |
| 9 | 280-281 | lysyl-tRNA synthetase | High |
| 10 | 284-285 | RNA polymerase subunits | High |
| 11 | 287-289 | 30S S12, S7 ribosomal proteins, elongation factor ef-G | High |
| 12 | 290-294 | 30S S10 and 50S L3, L4, L23, L2 ribosomal proteins | High |
| 13 | 295-298 | 30S S19, S3 and 50S L22 ribosomal proteins | High |
| 14 | 317-318 | RNA polymerase | High |
| 15 | 360 | 50S ribosomal protein L11 | High |
| 16 | 369 | 50S ribosomal protein L1 | High |
| 17 | 452-456 | mannose-specific PTS system component IIC | High |
| 18 | 639-640 | phosphocarrier protein HPr pthP, p-enolpyruvate protein ptI | High |
| 19 | 655-656 | phosphotransferase system enzyme II pthA | High |
| 20 | 697 | transcriptional regulator ygaP | High |
| 21 | 698 | glyceraldehyde 3-phosphate dehydrogenase | High |
| 22 | 699 | 3-phosphoglycerate kinase | High |
| 23 | 752 | glucose 6-phosphate isomerase | High |
| 24 | 772-779 | H+ ATPase a, c, b chains, delta, alpha, beta, gamma subunits | High |
| 25 | 817 | isoleucyl-tRNA synthetase | High |
| 26 | 845 | translation elongation factor ef-Tu | High |
| 27 | 846 | trigger factor protein cell division | High |
| 28 | 889 | phosphoglycerate dehydratase | High |
| 29 | 956-957 | phosphofructokinase, pyruvate kinase | High |
| 30 | 958 | Hypothetical protein | High |
| 31 | 968 | 30S ribosomal protein S1 | High |
| 32 | 1199-1196 | glycyl-tRNA synthetase alpha, beta chains, DNA primase, RNA polymerase sigma factor | High |
| 33 | 1204-1201 | PhoH, ef-Tu, GTPase | High |
| 34 | 1237-1238 | homoserine O-succinyltransferase MetA | High |
| 35 | 1511 | N-acetylglucosamine kinase | High |
| 36 | 1559-1559 | FGAM synthesis | High |
| 37 | 1599 | fructose bisphosphate aldolase | High |
| 38 | 1641 | glycerol-3-phosphate ABC transporter | High |
| 39 | 1645-1642 | ABC sugar transport | High |
| 40 | 1763 | oligoendopeptidase F | High |
| 41 | 1779 | fructose operon repressor | High |
| 42 | 1783-1782 | ABC transport, ATP-binding protein, permease | High |
| 43 | 1892-1891 | adenylosuccinate synthase and lyase | High |
| 44 | 40-38 | ribonucleotide reductase/cobalamin adenosyltransferase | Stress |
| 45 | 83 | protease | Stress |
| 46 | 96-97 | protease/chaperone, tricaboxylate transporter | Stress |
| 47 | 166 | K+ Transporter | Stress |
| 48 | 204 | aminopeptidase C | Stress |
| 49 | 329 | cell division protein ftsK | Stress |
| 50 | 396-395 | oxalyl-CoA decarboxylase | Stress |
| 51 | 397 | ABC transporter ATP binding | Stress |
| 52 | 405-406 | cochaperonin GroES, chaperonin GroEL | Stress |
| 53 | 555 | myosin-cross-reactive antigen | Stress |
| 54 | 638 | ATP-dependent Clp protease ATP-binding subunit CplE | Stress |
| 55 | 847 | clpX | Stress |
| 56 | 912 | 2-oxoglutarate/malate translocator | Stress |
| 57 | 913 | Peroxidase | Stress |

TABLE 2-continued

Promoters of the present invention and associated genes.

| SEQ ID NO | ORF#(s)[a] | Gene(s) controlled | Expression/Response |
|---|---|---|---|
| 58 | 914 | citrate lyase ligase | Stress |
| 59 | 1119 | hypothetical inner membrane protein | Stress |
| 60 | 1234 | Cd/Mn transport ATPase or H$^+$ ATPase | Stress |
| 61 | 1246 | heat shock protein DnaJ | Stress |
| 62 | 1249-1247 | heat-inducible transcription repressor HrcA, cochaparonin GrpE, Hsp70 cofactor, heat shock protein DnaK | Stress |
| 63 | 1339 | | Stress |
| 64 | 1429-1427 | transporter-membrane protein | Stress |
| 65 | 1432-1430 | | Stress |
| 66 | 1433 | dihydroxyacetone kinase | Stress |
| 67 | 1446 | multidrug resistance protein | Stress |
| 68 | 1683 | cation-transporting ATPase | Stress |
| 69 | 1910 | ATP-dependent protease ClpE | Stress |
| 70 | 400 | Sucrose 6-phosphate hydrolase ScrB | Sugar |
| 71 | 401 | PTS system II ABC ScrA | Sugar |
| 72 | 502-507 | ABC transporter substrate-binding protein | Sugar |
| 73 | 1012 | PTS system beta-glucoside-specific (trehalose) IIABC component | Sugar |
| 74 | 1013-1014 | trehalose operon transcription repressor | Sugar |
| 75 | 1442-1437 | sugar ABC transporter, sugar-binding protein | Sugar |
| 76 | 1459-1457 | galactokinase | Sugar |
| 77 | 1463-1462 | lactose permease | Sugar |
| 78 | 1467-1468 | beta-galactosidase large subunit | Sugar |
| 79 | 1469 | UDP-glucose 4-epimerase | Sugar |
| 80 | 1467-1468 | beta-galactosidase large subunit | Sugar |

[a]ORF# designation is as shown in FIG. 2.

TABLE 3A

| Sequence/Expression Profile | SEQ ID NO: |
|---|---|
| >8_high<br>gtcgtttcgcatatgaaattgataagtatcgtgaaggtacttaccac<br>attatgactttcactgctgacaacgctgacgcagttaacgaaTttag<br>ccgtttgtcaaagatcgacaacgctatcttgcgttcaatgaccgtta<br>agttagacaagtaattttaatttattgttttcgtgatttaggaa<u>agg</u><br><u>atgg</u>acaaaggt<br>following gene (8) is consistently highly expressed | 1 |
| >55_high<br>atcatctctatttgttgcgttgttttttgttatgagtatatattaca<br>ttttaaatgacaatgtgtcaccatttatttacttgtcttaataaatt<br>ctttatagttttcatttgttttcaatgatgtttcacgtgcaactgc<br>tttttttagaaaaattgttttttgtgttttttgttgaacaaacggaagt<br>gtat<u>aatgagga</u><br>following gene (55) is consistently highly expressed | 2 |
| >151_high<br>agcaatttaaaggttttaatgaaaaatttattgctttgggcaagtct<br>tccactcgtgaggacgttttttctgttcgtttgattaataatatcgt<br>taacaagcaggcttaattactgatcgttttttgacgacccgtaattaa<br>gccttttttgtgggcgaatagtttgttttatcactattttatgttttt<br><u>atggagga</u>cata<br>following genes (151, 152, 153, 154) are consistently highly expressed | 3 |
| >169_high<br>atatgaatcgtggtaagtaataggacgtgcttcaggcgtgttgcctg<br>tacgcatgctgattcttcagcaagactactacctcatgagagttata | 4 |
| gactcatggatcttgctttgaagggttttgtacattataggctccta<br>tcacatgctgaacctatggcctattacattttttttatatttca<u>agga</u><br><u>gg</u>aaaagaccac<br>following gene (169) is consistently highly expressed | |
| >175_high<br>ctcccacccaagacaattaataggacgcgcttcaggcgtgttgcctg<br>tacgcatgctgattcttcagcaagactactacctcatgagagttata<br>gactcatggatcttgctttgaagggttttgtacattataggctccta<br>tcacatgctgaacctatggcctattacattttttttatatttca<u>agga</u><br><u>gg</u>aaaagaccac<br>following gene (175) is consistently highly expressed | 5 |
| >185_high<br>aaaacaactacaaaatatttcttttttgtttttcatgattttttacact<br>tctcttagtatgcttttgttataagttagcacaaaaaagcagaaaat<br>aaaaagtagaaataaaaaaagatgttttttttgcccatatctctatga<br>aaaaaactgtgaaatgtgtaaaatatggatgaaacattgaatttaaa<br><u>aggaga</u>tatttc<br>following gene (185) is consistently highly expressed | 6 |
| >271_high<br>accagtattatgtttggtcttatcatatttttgacccggattaccca<br>aacctgcaattatcttcatcttatttacccctcattaataataatct<br>caactataatagcacaaacacaaaataataattttattaatgctctt<br>caacatggtataattttctttgttaaaattatcactaataaaaa<u>agg</u><br><u>ag</u>acttattgtt<br>following gene (271) is consistently highly expressed | 7 |
| >278_high<br>tgtttagcaatttatgctgatcgagaaccaattttcgttgaaaatac<br>gtatcaaaatcaaaattggataaaaaatggcaaacattattttctat<br>atgctaattaatttatcagtaaatatagttgaaaatattagtggtcg<br>gaacttgttttgtgataaaattttaaacgtataacttaaagactttg<br><u>cggagg</u>tttttt<br>following gene (278) is consistently highly expressed | 8 |

TABLE 3B

| Sequence/Expression Profile | SEQ ID NO: |
|---|---|
| >280-281_high<br>agatatgatcaatgaagatcatggagcagaacttatttgcaacttct<br>gtggtaacaaataccattacactgaagatgaattgaaagagattta<br>gctaagaaaaaagacgataaagattattaattaaatttaaagaggcc<br>taaggttttaaccttagggcttttttgatattataataaagtattt<br>tgaa<u>aggatgat</u><br>following genes (280 and 281) are consistently highly expressed | 9 |
| >284-285_high<br>aaaaataaaaaaatattatacaattttttgctgatttaaaaagactga<br>gattcaggattttgctgatctattgtccagcaaaatgataaggacaa<br>aaacgacacttgttgtttttgtctttttttatgcctaaaattgcggtt<br>ttttgaatttgtaacagaaatgtaatatttgcttcttagacagaaa<br><u>ggatg</u>ttttcc<br>following genes (284-285) are consistently highly expressed | 10 |
| >287-289_high<br>aattaagtaaaaaatatattgagttcaaaaaatcacctcattgttta<br>ttacgcaaaattcaaaaaattcttttttaaaaagtttgatttctatta<br>aaaccgagtacaatagtctttgtatgttttgaacagtctattcgcg<br>agtataaaaagaaactcccggatgtgtgaacaaaatagtattttta<u>ag</u> | 11 |

TABLE 3B-continued

| Sequence/Expression Profile | SEQ ID NO: |
|---|---|
| gagga aaaatta<br>following genes (287, 288, 289) are consistently highly expressed | |
| >290-294_high<br>ttgtaaccctt gatatttaagga cataccaagta caatagtctttgt gcttaaggggc gattgcgccct aagcgagtaa tattgttgtagagcg ttgacgcaaaa aggttgcggca cgccaggctgc attgccacagtggcg tgcgggaattt ttgccgagcga gtcatctttt aaagaagacgtta aggaggtaattta<br>following gene (290, 291, 292, 293 and 294) are consistently highly expressed | 12 |
| >295-298_high<br>taaggctccag ttggtcgtcca caacctatgac tccatggggtaaga aggctcgtgg tattaagacta gagatgtcaa gaaggctagcgagaag ttaatcattcg tcaccgtaagg tagcaagtaa tagaaggagggtta attaatgagcc gtagtattaa aaaaaggtcc ttttgctgatgcgtcat tgttaaagaagg<br>following genes (295, 296, 297 and 298) are consistently highly expressed | 13 |
| >317-318_high<br>aacatgtaga agtttctgtt aaaggtcctg gtgctggtcgtgaatct gctattagat cacttcaagc aactggtctt gaaattactgcaattcg tgacgttacg ccagttccccaca atggttccag accaccaaaacgtc gtcgtgctta atttttgtccatgatatt ataggacgtt acgttttgaa agggqcccagta<br>following genes (317, 318) are consistently highly expressed | 14 |
| >360_high<br>agaccaagtc aaggaaattg ctgagactaa gatgaaagaccttaacg ctgctgatat tgaagctgct atgcgcatggttgaaggt accgctaga agtatgggta tcgaagtcga agactaatcctgttatt tagttaacac attaggtggg agagttaaga gaagctcgtttgaccac atatacaagg agqaattcacac<br>following gene (360) is consistently highly expressed | 15 |
| >369_high<br>tttatccttg ctatctttga taatgcctgc tacaatagttaattgta aattctacct aagactcggg tggcatgacgcctcaaaa tcccgccga ggccagaaga taatgaagat ttttatgctccatgtctt tcggcatgg agttttgctt taaaaggcct tatagaatttattaatgcgatta tgg aggtgaaattaa<br>following gene (369) is consistently highly | 16 |

TABLE 3C

| Sequence/Expression Profile | SEQ ID NO: |
|---|---|
| following gene (369) is consistently highly expressed | |
| >452-456_high<br>aaaatcccttt ttatgacaaa ataaagggat ttttttattagacta atttgagcat ttggcttgaa ccgcaaggctttt cgtcttatttgaaa tttatttatatt gtatgaaatt atttccaaaaagtactttgtaaaag tgtgtatttat cgtataataa aagcggattcattttttt gatctaga gqaggaaattac<br>following genes (452, 455, 456) are consistently highly expressed | 17 |
| >639-640_high<br>gaaattatgg caaacgacaa tatattaccg gcagggccgaaagaggc ggatctatcg tctatactgc gacaaatacc gatgattgaatgatgta | 18 |

TABLE 3C-continued

| Sequence/Expression Profile | SEQ ID NO: |
|---|---|
| aactgttaca ttattgttgt ctaaactgtaaaaacatgataatctat tactcgaatg ggtatttatt accagtttaatttttttcaatttaaag gagatattcata<br>following genes (639-640) are consistently highly expressed | |
| >655-656_high<br>ttaataacat tttcaatact gtgccgctgaatggggtagactggttg tttctcttcc ttcttcctat tccgctagttctattagatgaagtaag aaagtggtta atgtattaca acaaaaatattaattaatttttatgta acttaagtgt ttaactgacc tttcttatgctagaattgactttaagg agatataatt<br>following genes (655, 656) are consistently highly expressed | 19 |
| >697_high<br>aattatttca ctcttcttag gatatttttaaaatagcacatctttttt cttgaattac taaaaatacc ttgttatactaacagtgtcgattggga aatgtatgaa ttgaagaatc gtacgtttctcttatattttaagtaa tctgggacag aaagtgacac aggggtggtcaatatacgtcccaggga aaggagggaacg<br>following gene (697) is consistently highly expressed | 20 |
| >698_high<br>aatctatata aaatacccca catatttgcctttgcttgcggtgctaa aaaagctaaa gcaattaaag catatatgcccaatgcacctcatcaaa cctggttaat tactgatgaa ggggcctcaaatatgatttttaagggg aaatgaaatc ccgttaaaat aaattgttgtttatagttcttaagga ggactttaggtt<br>following gene (698) is consistently highly expressed | 21 |
| >699_high<br>ttagttaaga ctgttgcttg gtacgacaatgaatactcattcacttg ccaaatggtt cgtactttgt tacactttgctactctttaatcattaa ttttaattaa ctgattatag ttaagtggtaatcgagaaggcggaggg agattcttcc ttccgccttt ttttgaagaaaaaataaatattttttg aggagaatatta<br>following gene (699) is consistently highly expressed | 22 |
| >752_high<br>gaaacgctac agttttttat taatgacaggtgttagtgatattgatga cgtgttttt taacacttgt ggcgctatttaggctatttaatatata ttcttttcaa aaaaaggtga atgcgcttataattggtactggtattc aagaaataag attgttaaaa taaaaatgttaaaattttaatagtta ggaaagcagattt<br>following gene (752) is consistently highly expressed | 23 |
| >772-779_high<br>gatgataaat tgctggacaa tggttacatttcccctggtttgggaga tgccggtgac agactcttcc ggtactaagtaaacacctttcacaaaa aatatttact ctaatgcgct ttcattttacacaaagaagatatttgg tgttaagatg atttacgtgt tcgagttttattcaacacgagaaggga ggtcacgaagta | 24 |

TABLE 3D

| Sequence/Expression Profile | SEQ ID NO: |
|---|---|
| following genes (772, 773, 774, 775, 776, 777, 778, 779) are consistently highly expressed | |
| >817_high<br>tagtggcgat tcagcgagtt agagatggtgtgagactaacataagtg cccaaaagtt gatcggctgc catattgatctaagcgtttttttgcacg | 25 |

TABLE 3D-continued

| Sequence/Expression Profile | SEQ ID NO: |
|---|---|
| ttacgcaaaagtaagtggaattctttttagaattcaatttaggtggt accacgattaacctcgtcctaatttggacgaggttttcttttt<u>agaa aggat</u>ttatta<br>following gene (817) is consistently highly expressed | |
| >845_high<br>taccaaattaaaataataagcaaaaaaggtttacattttcgaactat ttagtataattagcaaaggatattttcgttaggcatatcgcttaatc tttttactaggcatttgccgaagaaagtagtacaatattcaacaga gaattatcctttaacttatctcaacggacttcttgcaaatttac<u>agg agggt</u>cattttа<br>following gene (845) is consistently highly expressed | 26 |
| >846_high<br>ccgtgaaggtggtcgtaccgttggtgccggtcaagttactgaaatcc ttgactaatttctaacgatatagttaaaaaagatgcacttcttcact ggagcgcatcttttttcttttatattttgttttttgtgctagtttaag gtaagataaacttagtatgcaagaagcaaactcaaaattgacatt<u>tgga ggt</u>attttatta<br>following gene (846) is consistently highly expressed | 27 |
| >889_high<br>agttacgttatacatatattatagctctttgatatagcattttttac tgtgctttactattttttaaaatgtaaaccgctttcatatgtttaca cgatcacaaagttaggctaaaatttgtgttgtaaagcggagcaaaaa ttgttccgtatggcatgcaaaattttttgttacatgccataatttttg <u>aggaggt</u>ttata<br>following gene (889) is consistently highly expressed | 28 |
| >956-957_high<br>aaccaatttacgtaaagtaaactttaaagaataattgtctactttaa agaattgaattatcaatatatgtaagtgctaacataaactctgaagt gagaaacaataaattagcccaattttttgtgagattttttggtctaaaa aatgttaatatttacttgatgtgagaaattacacaaaataatcatg<u>a tgaggt</u>gaattc<br>following genes (956, 957) are consistently highly expressed | 29 |
| >958_high<br>agatttctgacggttcaactattactgttgatgctcgtcgtggtgct atttaccaaggtgaaatctcaaaccttttaataatatataaataaac agattagctaatcaaaaaatagtcagcttttgagctggctattttat tttgttcgaatatctcttatacttatatataaagaatatgtaaagt<u>a ggagа</u>tttttа<br>following gene (958) is consistently highly expressed | 30 |
| >968_high<br>ctcatcgcaaggtttcaccactaaaaaaggcagatgatgctattgaa attgatactacaaatatgtcaattgaccaggttgtagatgcaatttt agctaaaatcaaagaaaattaaaaaatttttttaaaaaaacagcaca aaatagtagaaaaatatcacagtttcctttaaaatgggacatgatat <u>tgggaggt</u>acat<br>following gene (968) is consistently highly expressed | 31 |
| >1199-1196_high<br>ataatgaggattagaaaagtactagttcagcgaatgtcgtttggtga gaggacatctaggaaaaggcccctctagtcatactcaattaagtgca ggaagaagacttcctgaattagggtggaaccgcgagatattcgtcc ctatgcaaaattttgcataggcttttttttatggcctagt | 32 |

TABLE 3E

| Sequence/Expression Profile | SEQ ID NO: |
|---|---|
| gc<u>aggaggag</u>aataaggaaa<br>following genes (1199, 1198, 1197, 1196) are consistently highly expressed | |
| >1204-1201_high<br>taacaaaatttaaaaatatattagtagtcataaaataagataatctgg tattaagtatttaagccttgaataaaggatacaataatttagttttc aataaaaatattccatataatagtaaataatcaatagttttatttta gttatgtagatagtttgttataatactattgggtttttaatagaaa<u>g aaggat</u>accaga<br>following genes (1204, 1203, 1202, 1201) are consistently highly expressed | 33 |
| >1237-1238_high<br>actaatgaatatttcgcccaacaatcatcttggttgaagttcaagca atacttctctagactactttcacctattttttaataatatatttcaa actgacaaaatattttgtcagtttttttctttaagtgtttttccttta cttaattttt aataagctgtataattaacccaactattaataagt<u>aa ggaggt</u>aaaatc<br>following genes (1237, 1238) are consistently highly expressed | 34 |
| >1511_high<br>tacccttgtttatatcccgtggatattcttagttggtatcctaatta gcctcttaactattataatttttattaagaattggataaaaagcaggc atgataacgctaacagcaaaaataatgctggaccaaccacccaaaaa tgtaataaaatgtatacgttatcattcggataaattaataacagaa<u>a gaag</u>tttgaat<br>following gene (1511) is consistently highly expressed | 35 |
| >1559-1552_high<br>ctttgaaaaagagagctataaagctctcttttttgttcaattctta caaaacacgaacgattatttatactatcattttttaatattcaataaa tcattgacattacagacacttattgataatattgttagcataaaagt gaacgaataattattcgcttgccagaaatgttcgtgtttttttacca<u>a ggagaaa</u>gaaaa<br>following genes (1559, 1558, 1557, 1556, 1554, 1553, 1552) are consistently highly expressed | 36 |
| >1599_high<br>ttggtgctcgccttgctttagttcaggctacatcaatcgttttgact gaatcacttagactttttaggtgtaaatgctcctaaggaaatgtaaag atttcaatgaaaagtaaaaaaatagcgcttacattttgtgaaaaattg ttcataatcgaattaataaggtacaatatgcatgtaagatatt<u>t agg aggt</u>atttttta<br>following gene (1599) is consistently highly expressed | 37 |
| >1641_high<br>catgctgatgaaggagaactcaaagaaattattggcgggattcagcc agctgttttggtaccggtgcacacactgcatccggagctggaagaga atccatttggagaacggatttttacctaaacgtggccaaactgtcacg ctttagtgaatcaaaaaatatattgttgtttagttttatttttt<u>agg agga</u>tttatcca<br>following gene (1641) is consistently highly expressed please note the RBS is one base shorter than that shown in the genome file | 38 |
| >1645-1642_high<br>aaatacgaacaaaaagacaaaaaagtagttttttgatttataaaatac gaaccagatacgaatgctaagtgaaaaatatttcatcaataagggat | 39 |

TABLE 3E-continued

| Sequence/Expression Profile | SEQ ID NO: |
|---|---|
| aactacgaattttttacatgaaatatttgtgattttttgtccatatag ctagaattaataaggaattttataaaaataaatcaatatatagtgg tgtgtgaaactt<br>following gene (1645, 1644, 1643, 1642) are consistently highly | |

TABLE 3F

| Sequence/Expression Profile | SEQ ID NO: |
|---|---|
| expressed<br>Please note a RBS was not found | |
| >1763_high<br>taatcttctctacgtttggaatttggatccattctttgtatcgtttc ccttcaaaattaatacaagtttatttgtatcacttttaatctctatg ataaaataaaattatcgataattaataataacttagtttttgagtta aattctacatcgaaatgcatctttaacaaagatggaatatttttc<u>ag gagg</u>aaacaaat<br>following gene (1763) is consistently highly expressed | 40 |
| >1779_high<br>attcttagtcaaaaccaaaaaaatgactaagaataattcaaaatgac gaagaaaagatgtcgtttcaatcaaaaaacggcatcttttttgcata taaatgaattttattgaatgataataaataaaaatgacgcttttga agaaaaatggttgattttgatggagaaagcgaatacaatgtttatcg <u>aggtgag</u>aaata<br>Also note the RBS does not appear on the genome file | 41 |
| >1783-1782_high<br>ggtaatgcgacacaaaacatcggatggttatcaactaagatttactc gtaaatctaccaaagtatatcctcattttttggcaagcatattggtgt caagcgttgctgatattttggatgtatgtgatattttatttctata taattaaaatttagatactaaaaatatcgaatcaatatcaaaaaag<u>tt gagg</u>aaaaaatc<br>following genes (1783, 1782) are consistently highly expressed please note the RBS is one base shorter than that of the genome file | 42 |
| >1892-1891_high<br>aatttgatttgctcccttttattttctgcttaccaaacgagaactact atatttgataaaagtattttttgtcaatataaaaatcgaactatgaaa taaattaaaaataaaataattcggttttttgcattgactaataattaa caaattgctagactatcatacgtaatatttatagagatttttt<u>atga ggtg</u>aatttcaa<br>following genes (1892, 1891) are consistently highly expressed | 43 |
| >40-38_stress<br>acttgtaggacaaactgattgtgaaggcgggcctgcccaatcaaat aatttacatggaggaaaaatgaagaacaagcataaatttaatttat tattttcaatcgttgcctttttggcttatttttaacgggaagttcaa atagtaattcatctgctacaaaaaatactgctaaaaatcaaattaca gtcaactatact<br>following genes (40, 39, 38) were induced over 2 fold in the presence of oxalate | 44 |
| >83_stress<br>cagaatatttggctcgtgaaacggcaaaagagatgctgattgatggg gaggcaaatattaacagtgatttaaaaatcattgatacagagccgaa tcacccaacaaaattaattgaaatttagcagttttagcaccttttgt tcatataattttcaaattttatctgtatgatattaggtaatatgagg ggagagttaagt<br>following gene (83) was induced over 2 fold in the presence of ethanol and over 4 fold in the presence of bile | 45 |

TABLE 3F-continued

| Sequence/Expression Profile | SEQ ID NO: |
|---|---|
| >96-97_stress<br>gtaagtcgcaaaaagttctttattcaatggactatcatgcaattcgc tgggttaatcattttgaccttagttggtttaggactactaatgttta gactttaaattttgttcaagaatgcttttatagcattctttttttatt gctctaaagcctataaaaattataaaattatataaatactttttatg gaggattctatc<br>following genes (97, 96) were repressed over 4 fold in the presence of pH 4.5 | 46 |

TABLE 3G

| Sequence/Expression Profile | SEQ ID NO: |
|---|---|
| >166_stress<br>gaagaaaatgggtgtatcaagaaaatgtcaacatggcattttctttt tttatattttttatactagctacaatttattttgtgggagattttg ataatgaataataagtccaaacgtatgagtgcggctggccttcttat cgccatcggtattgtttatggtgatattggtactagtccactttatg tt<u>atgaagt</u>caa<br>following gene (166) was repressed over 2 fold in the presence of bile and ethanol, and repressed over 3 fold in the presence of oxalate and pH 4.5 | 47 |
| >204_stress<br>atcaccctaccaaagcaaactgctggggatgatgataattctatcca gattgattaaattattagattattgcaagaagtctgattaatttaaa tggataattctctaaaacgggttcaatgattgaacccgttttgttt tggcttaaaatagtagttaatttaagaaaagattaaaaatgagaaa<u>a ggagat</u>ttttta<br>following gene (204) was induced over 2 fold in the presence of pH 5.5 | 48 |
| >329_stress<br>attgatggtaaacccaccaatgaaataaatggttatcaagcttggtt tgtcgcagaaggtactgaaccttttaaagttaaatttactaaaagag tcagtcttccaaaaatgttaaatcaaattcattaacaaatctgag gcttgtgaagttggatcaaatgtgtattttaaagcaacagatctcga ggtgattaacta<br>following gene (329) was induced over 4 fold in the presence of ethanol | 49 |
| >396-395_stress<br>gcattggataattttgaataatacagtaaaaagaatacttatttatt tatataaaaagtattcttttttatttgtgtacgcatattataaataa cacaacttattattcaatttgcttgtatctttttttaagaggtgta tcttgaactgtgaaatgcaagatgaaagcattttgggattttgaaa <u>gaaggt</u>ttttc<br>following genes (396, 395) were induced over 3 fold in the presence of pH 5.5 | 50 |
| >397_stress<br>attttattttctccatagttgatcctccaaacgtatctcaagtttg tgaatttacaatcaagcatttctatcataactgttaatataccattt acgcaagtgccagcttcacaaatatactttttttcacatatataattc aaaatagtgagctcagttaattcacatcctgtgataaaatattggtt <u>aggtg</u>aaaaatt<br>following gene (397) was induced over 3 fold in the presence of ethanol | 51 |
| >405-406_stress<br>gatctaaatattcaacatgttaaaactgaataaaaacacaattagca cttttttataaagagtgctaatttttctttgctttttttagtaaac gggttattatcatatttgtaagttagcacttaactaaaaggagtgct aacaatcaaaaatgattataaataataatgaagaaaataaattata<u>a gggga</u>actaaac<br>following genes (405, 406) were induced over 5 fold in the presence of pH 4.5 and bile, and induced over 10 fold in the presence of ethanol | 52 |

TABLE 3G-continued

| Sequence/Expression Profile | SEQ ID NO: |
|---|---|
| >555_stress<br>gtaatagagatatctatgtaaggctttttttgtagtaatgaaaataa<br>agttttttcgatttgttgctgagttcgcatgcttttcatgttcatag<br>tgtattatcccttatatttgtattagttgacatatgaaagcacttac<br>actatcattatagttgtaaatagttgcagatgtgacgattttttgaaa<br>gaagtgtaaact<br>following gene (555) was induced over 2 fold in<br>the presence of pH 4.5 and bile, and induced<br>over 12 fold in the presence of pH 4.5 | 53 |
| >638_stress<br>ataatccacaaatatcaccacacttttaaattttataattttttctt<br>cttttattctac | 54 |

TABLE 3H

| Sequence/Expression Profile | SEQ ID NO: |
|---|---|
| tctttacactaaattttctaaaatattaacattttatttaattctta<br>caaaaaataagttaaattggcgcttagcacttgactaccaagagtgc<br>taaatatataattttggtacagtttaattgaaggcgtaatatat<br>following gene (638) was induced over 5 fold in<br>the presence of bile and induced over 12 fold<br>in the presence of ethanol | |
| >847_stress<br>ttactgacaatgctaagcaagttgctaagtcaaaacttgaagcaaaa<br>gattcagacgataaagaaagcaagtaagactaatttacttattctt<br>aaaaggagcggcttaggccgcttttttttaatgttcaagcttaatat<br>ttactaatattagttaatttatgataatctaatttttggtagatatag<br>gaggaaaagtta<br>following gene (847) was repressed over 2 fold<br>in the presence of oxalate, bile and ethanol,<br>and repressed over 4 fold in the presence of<br>pH 4.5 | 55 |
| >912_stress<br>ttattgtgagctttttagttaataaataataacaagtatagatttg<br>aacatatttcgtaagatattttactttaaaatgatgaaaaaacatt<br>atttatttgaaattattaaaacaaaataaaaagtatataatgag<br>tatgtgaaaaaattcatttatattgattgctttgataaaactaagc<br>aggggaaggaaa<br>following gene (912) was induced over 2 fold in<br>the presence of pH 4.5 and pH 5.5 | 56 |
| >913_stress<br>ggcgacaacaggctatgtaaaacaaagtgaatggtggaagatgaact<br>ttattttaggcgcttatttacatggtgatatttggtatagtaggaact<br>atttggatgaaaattattggtatttggtaaaaataaaggcaatctga<br>tttcatagattgcctttttgcgtgataattgagggggtaggaataga<br>aagaagaaaag<br>following gene (913) was induced over 3 fold in<br>the presence of pH 5.5 | 57 |
| >914_stress<br>gaaaatatacaaactgcaattattcctgaatgcggtcatctacctca<br>ggcggagcgaccagatgaagtatataaaattattagtgattttttga<br>aaaatttaaaaaactagttctaaaattgaaataattaaactgcagga<br>gtacactgttcttgtgaaaaagattacttttattaatgcttagtaa<br>ggtggcacacttt<br>following gene (914) was induced over 4 fold in<br>the presence of pH 5.5 | 58 |
| >1119_stress<br>attatctctaactaacttaattatagtatttttttaagaaatgttaaa<br>gaaagagacacaatgtcactaatacgcaaatattgtgatattatgag<br>caatgtaatcaaacaaagttcggggactttgtaaagcaacttttac<br>atttggaggttttattattggagattgtcaaaactaaatcattaga<br>ttagctgttgct<br>following gene (1119) was induced over 3 fold<br>in the presence of bile, induced over 5 fold in<br>the presence of oxalate and induced over 7 fold<br>in the presence of ethanol | 59 |

TABLE 3H-continued

| Sequence/Expression Profile | SEQ ID NO: |
|---|---|
| >1234_stress<br>atcttttagcagcagcagtaatttgcttttcttcagctaccactaag<br>aaataatgtaattgtttaatattcatcaaatatatcctttttatttt<br>catgagcagtgatattaaaaaaattaatatcatatattttatttttag<br>tattttaatctaagcaatttatatgctaatttagttaaagaagattt<br>ggagggagaaaa<br>the following gene (1234) was induced over<br>9 fold in the presence of oxalate | 60 |
| >1246_stress<br>aatggtggtgctcaaggtgcagctggtcaagcaggtcctcaaggcgg<br>caacccaaatgat | 61 |

TABLE 3I

| Sequence/Expression Profile | SEQ ID NO: |
|---|---|
| ggtaacaatggtggtgcccaagatggtgaattccataaggtagatcc<br>taacaagtaatgggtttataattaaacaaaaagagaaaagaactacc<br>cattgagtagttctttctttgaaaacgataaggagttcaattgc<br>the following gene (1246) was induced over 2<br>fold in the presence of bile and ethanol | |
| >1249-1247_stress<br>agcaagttcaaccagcgatgattttagttgaacatgatgaatactt<br>attgaacgagtagctaatcaaagaattactttaaacttgaagaaaaa<br>agtttaaaataaattagcactcaggttgcattattgctaatttctag<br>tataatataatctgttagcacctgatagatgtgagtgctaaaagtga<br>gggcgatatata<br>the following genes (1249, 1248, 1247) were<br>induced over 2 fold in the presence of bile<br>and ethanol, repressed over 2 fold in the<br>presence of oxalate, and 1249 was also induced<br>over 2 fold in the presence of pH 4.5 | 62 |
| >1339_stress<br>tcttcatctaaaggatatcgttcatttgaacgggcactttacagagc<br>tgaaaatggcttaccggcatatgagggtactcaatcaattgaatata<br>aacaggaagaaattaaataatttattaatattatttttaatttgttgt<br>ggcgagatatatttttttcgttaaaatagaattactaactaaaagaaa<br>ggacgcttactg<br>following gene (1339) was induced over 2 fold<br>in the presence of oxalate and bile, and<br>induced over 4 fold in the presence of ethanol | 63 |
| >1429-1427_stress<br>gtgaagatgaatctcacaattctaaaaaaggtggctttggtattgga<br>ttagctatggctcaagaattaattcatactttccacggtaaaatttc<br>agtaaatcatagagaagaaatatcgttttagtgttagtctaaaaaa<br>ttgtcaaatagatgttcttgatagttgtataatttcaattaaagaat<br>cgaggaattatt<br>following genes (1429, 1428, 1427) were induced<br>over 2 fold in the presence of bile | 64 |
| >1432-2430_stress<br>atcgcttacaaatagattataacgcaataacttataaatttaaaaac<br>atatgacatgttgtcatatgtttcattaagtaaacgtgattttttaca<br>attttaaaataattttatagcaagttataactttttataatattcctg<br>ttactttcaaagaaaaatcaaaaatcattgctataatggcgtaaacg<br>aaagaaaggaca<br>following genes (1432, 1431, 1430) were induced<br>over 2 fold in the presence of bile | 65 |
| >1433_stress<br>tatagcaatgattttttgattttttctttgaaagtaacaggaatattat<br>aaaagttataacttgctataaaattattttaaaattgtaaaaatcac<br>gtttacttaatgaaacatatgacaacatgtcatatgttttttaaattt<br>ataagttattgcgttataatctatttgtaagcgattgcatttttgca<br>aaaggagaaatt<br>following gene (1433) was induced over 2 fold<br>in the presence of bile, and induced over 5<br>fold in the presence of pH 4.5 | 66 |

TABLE 3I-continued

| Sequence/Expression Profile | SEQ ID NO: |
|---|---|
| >1446_stress<br>caaaaagctggtgtaatttattttttctttatattttccattatctct<br>gcctcactaattaaaattaattatattaatttatgttaaattttttca<br>actttagtgtcatattatgtatcatatttgtaagattatttgacaca<br>gattaaaattaggactatattagttaacgatcttaattttcacaaaa<br>ggggatgacac<br>following gene (1446) was induced over 7 fold<br>in the presence of bile, and repressed over 2<br>fold in the presence of pH 4.5 | 67 |

TABLE 3J

| Sequence/Expression Profile | SEQ ID NO: |
|---|---|
| >1683_stress<br>gaagttgataaacctcaattagtataattgacactatgtcactaatg<br>cgctattatattagataatcaatatattgagaagcgcctatgacgct<br>gccaatacacaaatgaaaactgaacaagtttctcaaatggggaatgg<br>cttatgtaagtaggctgttctctattttttttattttatgaaaggagt<br>ggtatatccgat<br>following gene (1683) was induced over 3 fold<br>in the presence of bile and ethanol | 68 |
| >1910_stress<br>gtgaagcattacgagcgctttaatatcaagcgattaaggccaatttt<br>atattttttaatcacaataaagaataaaaatgtggaaaaagttcaaaa<br>taatacttgcaatctgtggataacatgttatacttataaatgtaaag<br>aattagcactcaacgcactagagtgctaatagacttaaattgattgg<br>gagtgtttatat<br>following gene (1910) was induced over 2 fold<br>in the presence of pH 4.5, induced over 5 fold<br>in the presence of bile, and induced over<br>15 fold in the presence of ethanol | 69 |
| >400_sugar<br>aattcactatttatgataacgtattcaaaaaatatgtcaatcgtttg<br>acacattttttttgaatttatttttattaatacttttcttatggtcc<br>aataaggcaagggtagtcaaatataatacgataaacgtttgacacat<br>ttttcataatctactagaattaatattaaagataacgcttacatgga<br>ggcttttttatt<br>following gene (400) was induced in the<br>presence of sucrose | 70 |
| >401_sugar<br>tattaattctagtagattatgaaaaatgtgtcaaacgtttatcatat<br>tatatttgactacccttgccttattggaccataagaaaagtattaat<br>aaaaaataaattcaaaaaaatgtgtcaaacgattgacatattttttg<br>aatacgttatcataaatagtgaattgagaataaaagcgtttacatag<br>gaggaaacaaat<br>following gene (401) was induced in the<br>presence of sucrose | 71 |
| >502-507_sugar<br>aactgttgacaagttgtgaaagcgatattatcatttaattgtaaatt<br>gaaacgtttccaaagtgttcaaatagttttttgctaaataattatt<br>tttttgtagcgaaatagaaacgtttcaattaatttaaaacaattaga<br>tcttagtaggaaaccttttaattttgtgcaaaattgaaacgtttca<br>aaaggaggaaaa<br>following genes (502, 503, 504, 505, 506, 507)<br>were induced in the presence of FOS | 72 |
| >1012_sugar<br>ctgattttgattccgtcatttatgtctttcctttctttgtacattta<br>ttatattcataaatgtatagacaagtaaagcataatttaagttacta<br>taaagtaaatattgtgatcgctttcaaaaaatatattgacaacttgt<br>atatacaagtttaatataatagctaaatctaatgaaaacgcttata<br>caggagaaaaca<br>following gene (1012) was induced in the<br>presence of trehalose | 73 |

TABLE 3J-continued

| Sequence/Expression Profile | SEQ ID NO: |
|---|---|
| >1013_sugar<br>ttcattgttttcattcattgtttttctcctgtataaagcgttttcat<br>tagatttagctattatattaaacttgtatatacaagttgtcaatata<br>tttttgaaagcgatcacaatatttactttatagtaacttaaattat<br>gctttacttgtctatacatttatgaatataataaatgtacaaagaaa<br>ggaaagacataa<br>following genes (1013, 1014) were induced in<br>the presence of trehalose | 74 |
| >1442-1437_sugar<br>gtattctaacatttgcttttattgcttacaatacaccgattagtaaa<br>ttaaatatgtcaaaatgtttataaggccaaatgacaataatgctaat<br>gaaaatactatggtttacatacatag | 75 |

TABLE 3K

| Sequence/Expression Profile | SEQ ID NO: |
|---|---|
| aatacgcaataattaaatatgtaatttatgaaagcgcttaaaatt<br>gaatgctatttatttagttattgaggagtgatctt<br>following genes (1442, 1441, 1440, 1439, 1438,<br>1437) were induced in the presence of raffinose | |
| >1459-1457_sugar<br>ttggtatcgtgatgtgataaaagaaaatggacaaaatttaaaata<br>attagtttaaaaaagaaaatattcttacagaatgtttccttttt<br>attatataaaattaaataatttatttatttgagtaaaccatttac<br>caaaaacaaataagagtatatactattatctgaaaacgattacag<br>taaaaattgaggtaaaaacg<br>following genes (1459, 1458, 1457) were induced<br>in the presence of lactose and galactose | 76 |
| >1463-1462_sugar<br>ataaaaagaaataaagacaacggggctggctaagcccttaaactg<br>taagagctggtcaatgtgattactcccaagtggaatatcagaata<br>ctagtgaagacgacagtaagtgaaacaaagaaaggaaaaatatat<br>ctttctgatatgtagaaaattcgtcttcttctacatatttccatg<br>ttttatatagcaggaatatt<br>following genes (1463, 1362) were induced in<br>the presence of lactose and galactose | |
| >1467-1468_sugar<br>acttacttacgtttattatacaaaatatttactcaattccaataa<br>atattaattttagcaaaaacaaatttttttaagaatcttcgtaata<br>aatattttactgttttagataaatattttattttattggttaat<br>tttttatttggtgatataataaaagcgttttcaaaaataatttat<br>tatagaaatcaggtattagt<br>following genes (1467, 1468) were induced in<br>the presence of lactose and galactose | 78 |
| >1469_sugar<br>tagttattgctggagctgtgcgcggcgttggtggtatcgacagct<br>ggggtgctgatgttgaaaagcaatatcacattaatcctgaaaaag<br>actacgaatttctcttcaatcttaattaaatattttatcaataat<br>agtaaatgttttactgatttatgtgttataatgtaatcgatttca<br>agaaaacaaaggagtaaaca<br>following gene (1469) was induced in the<br>presence of lactose and galactose | 79 |
| >1467-1468_sugar<br>gtggcaggtg aataacccga tttttgtgca atctctttaa<br>tagttgtcat agttaatttc tttttcttttt aaaaaactta<br>cttacgttta ttatacaaaa tatttactca attccaataa<br>atattaattt tagcaaaaac aaatttttta agaatcttcg<br>taataaaatat tttactgttt l ttagataaat<br>atttttatttt attggttaat tttttatttg gtgatataat<br>aaaagcgttt tcaaaaataa ttattatag aaatcaggta<br>ttagtcaagc aaacataaaa tggcttg<br>following genes (1467, 1468) were induced in<br>the presence of lactose and galactose, promoter | 80 |

TABLE 3K-continued

| Sequence/Expression Profile | SEQ ID NO: |
|---|---|
| sequence comprises the repressor sequence which allows for tight transcriptional regulation | |

TABLE 4

CRE ELEMENTS IN PROMOTERS REGULATING SUGAR UTILIZATION

| | | | | SEQ ID NO: |
|---|---|---|---|---|
| La400 | cre1 | TGataaaCGtttgaCA | -72 bp | 90 |
|  | cre2 | AGataaCGcttaCA | -17 bp | 91 |
| La401 | cre1 | TGaataCGttatCA | -48 bp | 92 |
|  | cre2 | TAaaagCGtttaCA | -17 bp | 93 |
| La452 | cre1 | TAaaagCGgattCA | -27 bp | 94 |
| La502 | cre1 | TGaaagCGatatTA | -172 bp | 95 |
|  | cre2 | TGaaaaCGtttcCA | -140 bp | 96 |
|  | cre3 | TAgaaaCGtttcAA | -78 bp | 97 |
|  | cre4 | TTcaaaCGtttcAA | -14 bp | 98 |
| La1012 | cre1 | TGtgatCGctttCA | -82 bp | 99 |
|  | cre2 | TGaaaaCGctttAT | -15 bp | 100 |
| La1013 | cre1 | ATaaagCGttttCA | -155 bp | 101 |
|  | cre2 | TGaaagCGatcaCA | -88 bp | 102 |
| La1442 | cre1 | AGaataCGcaatAA | -69 bp | 103 |
|  | cre2 | TGaaagCGcttaAA | -38 bp | 104 |
| La1459 | cre1 | TGaaaaCGattaCA | -27 bp | 105 |
| La1463 | cre1 | AAaattCGtcttCT | -36 bp | 106 |
| La1467 | cre1 | TAaaagCGttttCA | -32 bp | 107 |
| La1469 | cre1 | TGtaatCGatttCA | -21 bp | 108 |
|  |  |  |  | 109 |
|  |  |  |  | 110 |
|  |  |  |  | 111 |

43 HIGH promoters involved in the expression of 88 genes

26 STRESS promoters involved in the expression of 37 genes

10 SUGAR promoters involved in the expression of 25 genes

79 TOTAL promoters involved in the expression of 150 genes

TABLE 5

| ORF | pH 5.5 | pH 4.5 | Oxalate (1%) | Oxgall (0.5%) | Ethanol (15%) |
|---|---|---|---|---|---|
| 38, 39, 40 | | | ▓ | | |
| 83 | | | | 4 | ▓ |
| 96, 97 | | 4 | | | |
| 166 | | 3 | 3 | ▓ | ▓ |
| 204 | ▓ | | | | |
| 329 | | | | | 4 |
| 395, 396 | 3 | | | | 3 |
| 397 | | | | | |
| 405, 406 | | | | | 10 |
| 555 | ▓ | 12 | | | |
| 638 | | | | | 12 |
| 847 | | 4 | ▓ | ▓ | ▓ |
| 912 | ▓ | ▓ | | | |
| 913 | 3 | | | | |
| 914 | 4 | | | | |
| 1119 | | | | 3 | 7 |
| 1234 | | | 9 | | |
| 1246 | | | | ▓ | ▓ |
| 1247, 1248, 1249 | | ▓ | .5 | ▓ | ▓ |
| 1339 | | | ▓ | ▓ | 4 |
| 1427, 1428, 1429 | | | | ▓ | |
| 1430, 1431, 1432 | | | | ▓ | |
| 1433 | | 5 | | | |
| 1446 | | .5 | | 7 | |
| 1683 | | | | 3 | 3 |
| 1910 | ▓ | | | | 15 |

| | | |
|---|---|---|
| REPRESSION | <1 | white |
| INDUCTION | 2 | ▓ |
| | 3 | Gray |
| | 4 | Gray |
| | 5 | ■ |
| | 6-10 | Gray |
| | >10 | Gray |

The foregoing is considered as illustrative only of the principles of the invention. Further, since numerous modifications and changes will readily occur to those skilled in the art, it is not desired to limit the invention to the exact construction and operation shown and described herein. Therefore, accordingly, all suitable modifications and equivalents fall within the scope of the invention.

All publications, patent applications, patents and other references cited herein are incorporated by reference in their entireties for the teachings relevant to the sentence and/or paragraph in which the reference is presented.

That which is claimed is:

1. An isolated nucleic molecule comprising the nucleotide sequence set forth in SEQ ID NO: 6, wherein the nucleic acid molecule is operably associated with a heterologous nucleic acid of interest.

2. The isolated nucleic acid molecule of claim 1, wherein said heterologous nucleic acid of interest encodes a protein or peptide.

3. The isolated nucleic acid molecule according to claim 1, wherein said heterologous nucleic acid of interest encodes an antisense oligonucleotide.

4. The isolated nucleic acid molecule according to claim 1, wherein said heterologous nucleic acid of interest encodes a ribozyme or interfering RNA.

5. A plasmid comprising the nucleotide sequence of SEQ ID NO: 6, wherein said nucleotide sequence is heterologous with respect to the plasmid.

6. A method of transforming a cell comprising introducing a nucleic acid molecule comprising the nucleotide sequence of SEQ ID NO:6 into a cell.

7. A non-human cell comprising a nucleic acid molecule comprising the nucleotide sequence of SEQ ID NO:6, wherein the nucleotide acid molecule is operably associated with a heterologous nucleic acid of interest.

8. A non-human cell comprising a plasmid comprising the nucleotide sequence of SEQ ID NO: 6, wherein said nucleotide sequence is heterologous with respect to the plasmid.

9. The cell according to claim 7, wherein said cell is a lactic acid producing bacterial cell.

10. The cell according to claim 7, wherein said cell is selected from the group consisting of a cell of a gram positive bacterium, a lactic acid bacteria, *Lactobacillus acidophilus*, *Lactococcus lactis* or *Lactobacillus gasseri*.

* * * * *

UNITED STATES PATENT AND TRADEMARK OFFICE
CERTIFICATE OF CORRECTION

PATENT NO. : 7,495,092 B2  
APPLICATION NO. : 11/330471  
DATED : February 24, 2009  
INVENTOR(S) : Barrangou et al.

It is certified that error appears in the above-identified patent and that said Letters Patent is hereby corrected as shown below:

Column 9,
Line 34, "TTTTT nAAAAn" should read --TTTTnnAAAAnnn--.

Column 11,
Line 59, "finctional" should read --functional--.

Column 15,
Line 11, "Lacd" should read --LacI--.

Column 18,
Line 31, "Coming" should read --Corning--.

Column 90,
Line 13, "nucleotide" should read --nucleic--.

Signed and Sealed this

Fourteenth Day of July, 2009

JOHN DOLL  
*Acting Director of the United States Patent and Trademark Office*

SEQUENCE LISTING

<160> NUMBER OF SEQ ID NOS: 111

<210> SEQ ID NO 1
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)

-continued

```
<223> OTHER INFORMATION: Promoter region for ORF 8

<400> SEQUENCE: 1
gtcgtttcgc atatgaaatt gataagtatc gtgaaggtac ttaccacatt atgactttca      60
ctgctgacaa cgctgacgca gttaacgaat ttagccgttt gtcaaagatc gacaacgcta    120
tcttgcgttc aatgaccgtt aagttagaca agtaatttta atttattgtt ttcgtgattt    180
aggaaaggat ggacaaaggt                                                 200

<210> SEQ ID NO 2
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 55

<400> SEQUENCE: 2
atcatctcta tttgttgcgt tgtttttgt tatgagtata tattacattt taaatgacaa      60
tgtgtcacca tttatttact tgtcttaata aattctttat agttttcat ttgttttcaa    120 tgatgtttca cgtgcaactg cttttttaga aaaatattgt ttttgtgttt tgttgaacaa    180
acggaagtgt ataatgagga                                                 200

<210> SEQ ID NO 3
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 151-154

<400> SEQUENCE: 3
agcaatttaa aggttttaat gaaaaattta ttgttttggg caagtcttcc actcgtgagg      60
acgttttttc tgttcgtttg attaataata tcgttaacaa gcaggcttaa ttactgatcg    120
tttttgacga cccgtaatta agccttttt gtgggcgaat agtttgtttt atcactattt    180
tatgttttat ggaggacata                                                 200

<210> SEQ ID NO 4
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 169

<400> SEQUENCE: 4
atatgaatcg tggtaagtaa taggacgtgc ttcaggcgtg ttgcctgtac gcatgctgat      60
tcttcagcaa gactactacc tcatgagagt tatagactca tggatcttgc tttgaagggt    120
tttgtacatt ataggctcct atcacatgct gaacctatgg cctattacat ttttttatat    180
ttcaaggagg aaaagaccac                                                 200

<210> SEQ ID NO 5
<211> LENGTH: 200
<212> TYPE: DNA
<213> ORGANISM: Lactobacillus acidophilus
<220> FEATURE:
<221> NAME/KEY: misc_feature
```

<222> LOCATION: (1)..(200)
<223> OTHER INFORMATION: Promoter region for ORF 175

<400> SEQUENCE: 5

```
ctcccaccca agacaattaa taggacgcgc ttcaggcgtg ttgcctgtac gcatgctgat      60
tcttcagcaa gactactacc tcatgagagt tatagactca tggatcttgc tttgaagggt     120
tttgtacatt ataggctcct atcacatgct gaacctatgg cctattacat ttttttatat    180
ttcaaggagg aaaagaccac                                                 200
```

<210> SEQ ID NO 6
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 185

<400> SEQUENCE: 6

```
aaaacaacta caaatatttt cttttgttt tcatgattt ttacacttct cttagtatgc       60
ttttgttata agttagcaca aaaaagcaga aaataaaaag tagaaataaa aaaagatgtt    120
tttttgccca tatctctatg aaaaaaactg tgaaatgtgt aaaatatgga tgaaacattg    180
aatttaaaag gagatatttc                                                200
```

<210> SEQ ID NO 7
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 271

<400> SEQUENCE: 7

```
accagtatta tgtttggtct tatcatattt ttgacccgga ttacccaaac ctgcaattat     60
cttcatctta tttaccccctc attaataata atctcaacta taatagcaca aacacaaaat  120 aataattta ttaatgctct tcaacatggt ataattttct ttgttaaaat tatcactaat    180
aaaaaaggag acttattgtt                                                200
```

<210> SEQ ID NO 8
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 278

<400> SEQUENCE: 8

```
tgtttagcaa tttatgctga tcgagaacca attttcgttg aaaatacgta tcaaaatcaa     60
aattggataa aaaatggcaa acattatttt ctatatgcta attaatttat cagtaaaatat   120 agttgaaaat attagtggtc ggaacttgtt ttgtgataaa attttaaacg tataacttaa   180
agactttgcg gaggttttt                                                 200
```

<210> SEQ ID NO 9
<211> LENGTH: 200
<212> TYPE: DNA
<213> ORGANISM: Lactobacillus acidophilus
<220> FEATURE:

<221> NAME/KEY: misc_feature
<222> LOCATION: (1)..(200)
<223> OTHER INFORMATION: Promoter region for ORF 280-281

<400> SEQUENCE: 9
agatatgatc aatgaagatc atggagcaga acttatttgc aacttctgtg gtaacaaata    60
ccattacact gaagatgaat tgaaagagat tttagctaag aaaaaagacg ataaagatta   120
ttaattaaat ttaaagaggc ctaaggtttt aacctttagg gcttttttga tattataata   180
aagtattttg aaaggatgat                                               200

<210> SEQ ID NO 10
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 284-285

<400> SEQUENCE: 10
aaaaataaaa aaatattata caattttttgc tgatttaaaa agactgagat tcaggatttt    60
gctgatctat tgtccagcaa aatgataagg acaaaaacga cacttgttgt ttttgtcttt   120
tttatgccta aaattgcggt ttttgaatt tgtaacagaa atgtaatatt tgcttcctta   180
gacagaaagg atgttttcc                                                200

<210> SEQ ID NO 11
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 287-289

<400> SEQUENCE: 11
aattaagtaa aaatatatt gagttcaaaa aatcacctca ttgtttatta cgcaaaattc    60
aaaaaattct ttttaaaaag tttgatttct attaaaaacc gagtacaata gtctttgtat   120
gttttgaaca gtctattcgc gagtataaaa agaaactccc ggatgtgtga acaaaatagt   180 attttttagga ggaaaaatta                                              200

<210> SEQ ID NO 12
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 290-294

<400> SEQUENCE: 12
ttgtaaccct tgatatttaa ggacatacca agtacaatag tctttgtgct taaggggcga    60
ttgcgcccta agcgagtaat attgttgtag agcgttgacg caaaaggttg cggcacgcca   120
ggctgcattg ccacagtggc gtgcggggaa ttttttgccga gcgagtcatc ttttaaagaa   180
gacgttaagg aggtaattta                                               200

<210> SEQ ID NO 13
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 295-298

<400> SEQUENCE: 13

| | | |
|---|---|---|
| taaggctcca gttggtcgtc cacaacctat gactccatgg ggtaagaagg ctcgtggtat | 60 |
| taagactaga gatgtcaaga aggctagcga gaagttaatc attcgtcacc gtaagggtag | 120 |
| caagtaatag aaggagggtt aattaatgag ccgtagtatt aaaaaaggtc cttttgctga | 180 |
| tgcgtcattg ttaaagaagg | 200 |

<210> SEQ ID NO 14
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 317-318

<400> SEQUENCE: 14

| | | |
|---|---|---|
| aacatgtaga agtttctgtt aaaggtcctg gtgctggtcg tgaatctgct attagatcac | 60 |
| ttcaagcaac tggtcttgaa attactgcaa ttcgtgacgt tacgccagtt ccccacaatg | 120 |
| gttccagacc accaaaacgt cgtcgtgctt aattttgtcc atgatattat aggacgttac | 180 |
| gttttgaaag gggcccagta | 200 |

<210> SEQ ID NO 15
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 360

<400> SEQUENCE: 15

| | | |
|---|---|---|
| agaccaagtc aaggaaattg ctgagactaa gatgaaagac cttaacgctg ctgatattga | 60 |
| agctgctatg cgcatggttg aaggtaccgc tagaagtatg ggtatcgaag tcgaagacta | 120 |
| atcctgttat ttagttaaca cattaggtgg gagagttaag agaagctcgt ttgaccacat | 180 |
| atacaaggag gaattcacac | 200 |

<210> SEQ ID NO 16
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 369

<400> SEQUENCE: 16

| | | |
|---|---|---|
| tttatccttg ctatctttga taatgcctgc tacaatagtt aattgtaaat tctacctaag | 60 |
| actcgggtgg catgacgcct caaaatcccg ccgaggccag aagataatga agattttat | 120 |
| gctccatgtc tttcggcatg gagttttgc tttaaaaggc cttatagaat ttattaatgc | 180 |
| gattatggag gtgaaattaa | 200 |

<210> SEQ ID NO 17
<211> LENGTH: 200
<212> TYPE: DNA

<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 452, 455 and 456

<400> SEQUENCE: 17

```
aaaatccctt tttatgacaa aataaaaggg attttttttat tagactaatt tgagcatttg    60
gcttgaaccg caaggctttt cgtcttattt gaaatttatt tatattgtat gaaattattt   120
ccaaaaagta ctttgtaaaa gtgtgtattt atcgtataat aaaagcggat tcattttttt   180
gatctagagg aggaaattac                                                200
```

<210> SEQ ID NO 18
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 639-640

<400> SEQUENCE: 18

```
gaaattatgg caaacgacaa tatattaccg gcagggccga agaggcggga tctatcgtct    60
atactgcgac aaataccgat gattgaatga tgtaaactgt tacattattg ttgtctaaac   120
tgtaaaaaca tgataatcta ttactcgaat gggtatttat taccagttta attttttttca  180
atttaaagga gatattcata                                                200
```

<210> SEQ ID NO 19
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 655-656

<400> SEQUENCE: 19

```
ttaataacat tttcaatact gtgccgctga atggggtaga ctggttgttt ctcttccttc    60
ttcctattcc gctagttcta ttagatgaag taagaaagtg gttaatgtat tacaacaaaa   120
atattaatta atttttatgt aacttaagtg tttaactgac ctttcttatg ctagaattga   180
ctttaaggag atatataatt                                                200
```

<210> SEQ ID NO 20
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 697

<400> SEQUENCE: 20

```
aattatttca ctcttcttag gatattttta aaatagcaca tctttttctt gaattactaa    60
aaataccttg ttatactaac agtgtcgatt gggaaatgta tgaattgaag aatcgtacgt   120
ttctcttata ttttttaagta atctgggaca gaaagtgaca cagggggtggt caatatacgt  180
cccagggaaa ggagggaacg                                                200
```

<210> SEQ ID NO 21
<211> LENGTH: 200

```
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 698

<400> SEQUENCE: 21
aatctatata aaatacccca catatttgcc tttgcttgcg gtgctaaaaa agctaaagca      60
attaaagcat atatgcccaa tgcacctcat caaacctggt taattactga tgaaggggcc     120
tcaaatatga ttttaaaggg gaaatgaaat cccgtttaaa ataaattgtt gtttatagtt     180
cttaaggagg actttaggtt                                                 200

<210> SEQ ID NO 22
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 699

<400> SEQUENCE: 22
ttagttaaga ctgttgcttg gtacgacaat gaatactcat tcacttgcca aatggttcgt      60
actttgttac actttgctac tctttaatca ttaattttaa ttaactgatt atagttaagt     120
ggtaatcgag aaggcggagg gagattcttc cttccgcctt tttttgaaga aaaaataaat     180 atttttgag gagaatatta                                                  200

<210> SEQ ID NO 23
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 752

<400> SEQUENCE: 23
gaaacgctac agttttttatt aatgacaggt gttagtgata ttgatgacgt gttttttaac     60
acttgtggcg ctattttagg ctatttaata tatattcttt tcaaaaaaag gtgaatgcgc    120
ttataattgg tactggtatt caagaaataa gattgttaaa ataaaaatgt taaaattttt    180
aatagttagg aagcagattt                                                200

<210> SEQ ID NO 24
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 772-779

<400> SEQUENCE: 24
gatgataaat tgctggacaa tggttacatt ttccctggtt tgggagatgc cggtgacaga      60
ctcttcggta ctaagtaaac accttttcac aaaaaatatt tactctaatg cgctttcatt    120
ttacacaaag aagatatttg gtgttaagat gatttacgtg ttcgagtttt attcaacacg    180
agaagggagg tcacgaagta                                                200

<210> SEQ ID NO 25
```

```
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 817

<400> SEQUENCE: 25
tagtggcgat tcagcgagtt agagatggtg tgagactaac ataagtgccc aaaagttgat      60
cggctgccat attgatctaa gcgttttttg cacgttacgc aaaagtaagt ggaattcttt     120
ttagaattca atttaggtgg taccacgatt aacctcgtcc taatttggac gaggttttct     180
ttttagaaag gattttatta                                                 200

<210> SEQ ID NO 26
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 845

<400> SEQUENCE: 26
taccaaatta aaataataag caaaaaaggt ttacattttc gaactattta gtataattag      60
caaaggatat tttcgttagg catatcgctt aatcttttt actaggcatt tgccgaagaa     120
agtagtacaa tattcaacag agaattatcc tttaacttat ctcaacggac ttcttgcaaa     180
tttacaggag ggtcattta                                                  200

<210> SEQ ID NO 27
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 846

<400> SEQUENCE: 27
ccgtgaaggt ggtcgtaccg ttggtgccgg tcaagttact gaaatccttg actaatttct      60
aacgatatag ttaaaaaaga tgcacttctt cactggagcg catcttttt cttttatatt     120 tgttttttgt gctagtttaa ggtaagataa cttagtatgc aagaagcaaa ctcaaaattg     180
acattggagg tattttatta                                                 200

<210> SEQ ID NO 28
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 889

<400> SEQUENCE: 28
agttacgtta tacatatatt atagctcttt gatatagcat ttttactgt gctttactat      60 tttttaaaat gtaaaccgct ttcatatgtt tacacgatca caagttagg ctaaaatttg     120 tgttgtaaag cggagcaaaa attgttccgt atggcatgca aaatttttgt tacatgccat     180 aattttgag gaggtttata                                                  200
```

<210> SEQ ID NO 29
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 956-957

<400> SEQUENCE: 29

```
aaccaattta cgtaaagtaa actttaaaga ataattgtct actttaaaga attgaattat      60
caatatatgt aagtgctaac ataaactctg aagtgagaaa caataaatta gcccaatttt     120
tgtgagattt ttggtctaaa aaatgttaat atttacttga tgtgagaaat tacacaaaat    180
aatcatgatg aggtgaattc                                                 200
```

<210> SEQ ID NO 30
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 958

<400> SEQUENCE: 30

```
agatttctga cggttcaact attactgttg atgctcgtcg tggtgctatt taccaaggtg      60
aaatctcaaa cctttaataa tatataaata aaacagatta gctaatcaaa aaatagtcag     120
cttttgagct ggctatttta ttttgttcga atatctctta tacttatata taaagaatat    180
gtaaagtagg agattttta                                                 200
```

<210> SEQ ID NO 31
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 968

<400> SEQUENCE: 31

```
ctcatcgcaa ggtttcacca ctaaaaaagg cagatgatgc tattgaaatt gatactacaa      60
atatgtcaat tgaccaggtt gtagatgcaa ttttagctaa aatcaaagaa aattaaaaaa     120
tttttttaaa aaaacagcac aaaatagtag aaaaatatca cagtttcctt taaaatggga    180
catgatattg ggaggtacat                                                 200
```

<210> SEQ ID NO 32
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1199-1196

<400> SEQUENCE: 32

```
ataatgagga ttagaaaagt actagttcag cgaatgtcgt ttggtgagag gacatctagg      60
aaaaggcccc tctagtcata ctcaattaag tgcaggaaga agacttcctg aattagggtg     120
gaaccgcgag atatttcgtc cctatgcaaa attttgcata ggcttttttt atggcctagt    180
gcaggaggag aataaggaaa                                                 200
```

<210> SEQ ID NO 33
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1201-1204

<400> SEQUENCE: 33

```
taacaaaatt taaaaatatt tagtagtcat aaaataagat aatctggtat taagtattta      60
agccttgaat aaaggataca ataatttagt tttcaataaa aatattccat ataatagtaa     120
ataatcaata gttttatttt agttatgtag atagtttgtt ataatactat tgggttttta     180
atagaaagaa ggataccaga                                                 200
```

<210> SEQ ID NO 34
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1237-1238

<400> SEQUENCE: 34

```
actaatgaat atttcgccca acaatcatct tggttgaagt tcaagcaata cttctctaga      60
ctactttcac ctatttttta ataatatatt tcaaactgac aaaatatttt gtcagttttt     120
tctttaagtg ttttccttt acttaatttt taataagctg tataattaac ccaactatta     180
ataagtaagg aggtaaaatc                                                 200
```

<210> SEQ ID NO 35
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1511

<400> SEQUENCE: 35

```
taccettgtt tatatcccgt ggatattctt agttggtatc ctaattagcc tcttaactat      60
tataatttta ttaagaattg gataaaaagc aggcatgata acgctaacag caaaaataat     120
gctggaccaa ccacccaaaa atgtaataaa atgtatacgt tatcattcgg ataaattaat     180
aacagaaaga agatttgaat                                                 200
```

<210> SEQ ID NO 36
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1552-1559

<400> SEQUENCE: 36

```
ctttgaaaaa gagagctata aagctctctt tttttgttca attcttacaa aacacgaacg      60
attatttata ctatcatttt taatattcaa taaatcattg acattacaga cacttattga     120
taatattgtt agcataaaag tgaacgaata attattcgct tgccagaaat gttcgtgttt     180
tttaccaagg agaaagaaaa                                                 200
```

<210> SEQ ID NO 37
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1599

<400> SEQUENCE: 37

```
ttggtgctcg ccttgcttta gttcaggcta catcaatcgt tttgactgaa tcacttagac    60
ttttaggtgt aaatgctcct aaggaaatgt aaagatttca atgaaaagta aaaaatagcg   120
cttacatttt gtgaaaaatt gttcataatc gaattaataa ggtacaatat gcatgtaaga   180
tatttaggag gtatttttta                                                200
```

<210> SEQ ID NO 38
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1641

<400> SEQUENCE: 38

```
catgctgatg aaggagaact caaagaaatt attggcggga ttcagccagc tgttttggta    60
ccggtgcaca cactgcatcc ggagctggaa gagaatccat ttggagaacg gattttacct   120
aaacgtggcc aaactgtcac gctttagtga atcaaaaaat atattgttgt ttagttttat   180 ttttaggag gatttatcca                                                 200
```

<210> SEQ ID NO 39
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1645-1642

<400> SEQUENCE: 39

```
aaatacgaac aaaaagacaa aaaagtagtt tttgatttat aaaatacgaa ccagatacga    60
atgctaagtg aaaaatattt catcaataag ggataactac gaatttttta catgaaatat   120
ttgtgatttt tgtccatata gcttagaatt aataaggaat tttataaaaa taaatcaata   180
tatagtggtg tgtgaaactt                                                200
```

<210> SEQ ID NO 40
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1763

<400> SEQUENCE: 40

```
taatcttctc tacgtttgga atttggatcc attctttgta tcgtttccct tcaaaattaa    60
tacaagttta tttgtatcac ttttaatctc tatgataaaa taaaattatc gataattaat   120
aataacttag tttttgagtt aaattctaca tcgaaatgca tctttaacaa agatggaata   180
```

```
tttttcagga ggaaacaaat                                               200

<210> SEQ ID NO 41
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1779

<400> SEQUENCE: 41
attcttagtc aaaccaaaa aaatgactaa gaataattca aaatgacgaa gaaaagatgt     60
cgtttcaatc aaaaaacggc atctttttg catataaatg aatttattg aatgataata    120 aataaaaatg acgcttttg aagaaaaatg gttgatttg atggagaaag cgaatacaat    180
gtttatcgag gtgagaaata                                              200

<210> SEQ ID NO 42
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1783-1782

<400> SEQUENCE: 42
ggtaatgcga cacaaaacat cggatggtta tcaactaaga tttactcgta aatctaccaa    60
agtatatcct cattttggc aagcatattg gtgtcaagcg ttgctgaata ttttggatgt   120
atgtgatatt ttatttctat ataattaaat ttagatacta aaaatatcga atcaatatca   180 aaaagttga ggaaaaaatc                                              200

<210> SEQ ID NO 43
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1892-1891

<400> SEQUENCE: 43
aatttgattt gctccctta ttttctgctt accaaacgag aactactata tttgataaaa    60 gtattttgt caatataaaa atcgaactat gaaataaatt aaaaataaaa taattcggtt   120
tttgcattga ctaataatta acaaattgct agactatcat acgtaatatt tatagagatt   180
ttttatgagg tgaatttcaa                                              200

<210> SEQ ID NO 44
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 40-38

<400> SEQUENCE: 44
acttgtagga caaactgatt gtgaaggcgg ggcctgccca atcaaataat ttacatggag    60
gaaaaaatga agaacaagca taaatttaat ttattatttt caatcgttgc cttttggct   120 tattttaac gggaagttca aatagtaatt catctgctac aaaaaatact gctaaaaatc   180
```
aaattacagt caactatact                                                  200

<210> SEQ ID NO 45
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 83

<400> SEQUENCE: 45
cagaatattt ggctcgtgaa acggcaaaag agatgctgat tgatggggag gcaaatatta     60
acagtgattt aaaaatcatt gatacagagc cgaatcaccc aacaaaatta attgaaattt    120
agcagtttta gcacctttg ttcatataat tttcaaattt tatctgtatg atattaggta     180
atatgagggg agagttaagt                                                  200

<210> SEQ ID NO 46
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 96-97

<400> SEQUENCE: 46
gtaagtcgca aaagttctt tattcaatgg actatcatgc aattcgctgg gttaatcatt      60
ttgaccttag ttggtttagg actactaatg tttagacttt aaattttgtt caagaatgct    120
tttatagcat tcttttttat tgctctaaag cctataaaaa ttataaaatt atataaatac    180
tttttatgga ggattctatc                                                  200

<210> SEQ ID NO 47
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 166

<400> SEQUENCE: 47
gaagaaaatg ggtgtatcaa gaaaatgtca acatggcatt ttcttttttt atatttttta     60
tactagctac aatttatttt gtgggagatt tttgataatg aataataagt ccaaacgtat    120
gagtgcggct ggccttctta tcgccatcgg tattgtttat ggtgatattg gtactagtcc    180
actttatgtt atgaagtcaa                                                  200

<210> SEQ ID NO 48
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 204

<400> SEQUENCE: 48
atcaccctac caaagcaaac tgctggggat gatgataatt ctatccagat tgattaaatt     60
attagattat tgcaagaagt ctgattaatt taaatggata attctctaaa acgggttcaa    120
tgattgaacc cgttttttgtt ttggcttaaa atagtagtta atttaagaaa agattaaaaa   180
tgagaaaagg agattttta                                                200

<210> SEQ ID NO 49
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 329

<400> SEQUENCE: 49
attgatggta aacccaccaa tgaaataaat ggttatcaag cttggtttgt cgcagaaggt    60
actgaacctt ttaaagttaa atttactaaa agagtcagtc ttccaaaaat gttaaatcaa   120
atttcattaa caaatcttga ggcttgtgaa gttggatcaa atgtgtattt taaagcaaca   180
gatctcgagg tgattaacta                                               200

<210> SEQ ID NO 50
<211> LENGTH: 200
<212> TYPE: DNA
<213> ORGANISM: Lactobacillus acidophilus
<220> FEATURE:
<221> NAME/KEY: misc_feature
<222> LOCATION: (1)..(396)
<223> OTHER INFORMATION: Promoter region for ORF 396-395
<220> FEATURE:
<221> NAME/KEY: misc_feature
<222> LOCATION: (1)..(200)
<223> OTHER INFORMATION: Promoter region for ORF 396-395

<400> SEQUENCE: 50
gcattggata attttgaata atacagtaaa aagaatactt atttatttat ataaaaaagt    60
attcttttta tttgtgtacg catattataa ataacacaac ttattattca atttgcttgt   120 atctttttt taagaggtgt atcttgaact tgaaatgcaa gatgaaagca ttttgggat    180 ttttgaaaga aggttttttc                                               200

<210> SEQ ID NO 51
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 397

<400> SEQUENCE: 51 atttttatt tctccatagt tgatcctcca aacgtatctc aagtttgtga atttacaatc    60
aagcatttct atcataactg ttaatatacc atttacgcaa gtgccagctt cacaaatata   120 ctttttcac atatataatt caaaatagtg agctcagtta attcacatcc tgtgataaaa   180
tattggttag gtgaaaaatt                                               200

<210> SEQ ID NO 52
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 405-406

<400> SEQUENCE: 52

```
gatctaaata ttcaacatgt taaaactgaa taaaaacaca attagcactt ttttataaag      60
agtgctaatt ttttcttgct ttttttagt aaacgggtta ttatcatatt tgtaagttag     120
cacttaacta aaaggagtgc taacaatcaa aatgattat aataataat gaagaaaata      180 aattataagg gggactaaac                                                 200

<210> SEQ ID NO 53
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 555

<400> SEQUENCE: 53
gtaatagaga tatctatgta aggcttttt tgtagtaatg aaaataaagt tttttcgatt      60
tgttgctgag ttcgcatgct tttcatgttc atagtgtatt atcccttata tttgtattag    120
ttgacatatg aaagcactta cactatcatt atagttgtaa atagttgcag atgtgacgat    180
ttttgaaaga agtgtaaatt                                                200

<210> SEQ ID NO 54
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 638

<400> SEQUENCE: 54
ataatccaca aatatcacca cacttttta atttatataat ttttcttctt tttattctac    60
tctttacact aaattttcta aaatattaac attttattta attcttacaa aaaataagtt   120
aaattggcgc ttagcacttg actaccaaga gtgctaaata tataattttg gtacagttta   180
attgaaaggc ggtaatatat                                                200

<210> SEQ ID NO 55
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 847

<400> SEQUENCE: 55
ttactgacaa tgctaagcaa gttgctaagt caaaacttga agcaaaagat tcagacgata    60
aagaaagcaa gtaagactaa tttacttatt tcttaaaagg agcggcttta ggccgctttt   120
tttaatgttc aagcttaata tttactaata ttagttaatt tatgataatc taattttggt   180
agatatagga ggaaaagtta                                                200

<210> SEQ ID NO 56
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 912
```

```
<400> SEQUENCE: 56
ttattgtgag cttttttagt taataaataa taacaagtat agatttgaac atatttcgta      60
agatatttta cttttaaaat gatgaaaaaa cattatttat tttgaaatta tttaaaaaca     120
aaataaaaag tatataatga gtatgtgaaa aaattcattt tatattgatt gctttgataa     180
aactaagcag gggaaggaaa                                                 200

<210> SEQ ID NO 57
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 913

<400> SEQUENCE: 57
ggcgacaaca ggctatgtaa aacaaagtga atggtggaag atgaacttta ttttagggct      60
tatttacatg gtgatatttg gtatagtagg aactatttgg atgaaaatta ttggtatttg     120
gtaaaaataa aggcaatctg atttcataga ttgccttttt tgcgtgataa ttgaggggta     180
ggaatagaaa gaagaaaaag                                                 200

<210> SEQ ID NO 58
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 914

<400> SEQUENCE: 58
gaaaatatac aaactgcaat tattcctgaa tgcggtcatc tacctcaggc ggagcgacca      60
gatgaagtat ataaaattat tagtgatttt ttgaaaaatt taaaaaacta gttctaaaat     120
tgaaataatt aaactgcagg agtacactgt tcttgtgaaa aagattactt tttattaatg     180
cttagtaagg tggcacattt                                                 200

<210> SEQ ID NO 59
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1119

<400> SEQUENCE: 59
attatctcta actaacttaa ttatagtatt ttttaagaaa tgttaaagaa agagacacaa      60
tgtcactaat acgcaaatat tgtgatatta tgagcaatgt aatcaaacaa agttcgggga     120
ctttgtaaag caacttttta catttggagg ttttattatt ggagattgtc aaaactaaat     180
catttagatt agctgttgct                                                 200

<210> SEQ ID NO 60
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1234
```

<400> SEQUENCE: 60

```
atcttttagc agcagcagta atttgctttt cttcagctac cactaagaaa taatgtaatt      60
gtttaatatt catcaaatat atcctttta ttttcatgag cagtgatatt aaaaaaatta     120
atatcatata ttttatttta gtattttaat ctaagcaatt tatatgctaa tttagttaaa    180
gaagatttgg agggagaaaa                                                 200
```

<210> SEQ ID NO 61
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1246

<400> SEQUENCE: 61

```
aatggtggtg ctcaaggtgc agctggtcaa gcaggtcctc aaggcggcaa cccaaatgat     60
ggtaacaatg gtggtgccca agatggtgaa ttccataagg tagatcctaa caagtaatgg    120
gtttataatt aaacaaaaag agaaaagaac tacccattga gtagttcttt tcttttgaaa    180
acgataagga gttcaattgc                                                 200
```

<210> SEQ ID NO 62
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1249-1247

<400> SEQUENCE: 62

```
agcaagttca accagcgatg attttagttg aacatgatga atactttatt gaacgagtag     60
ctaatcaaag aattacttta aacttgaaga aaaagtttta aaataaatta gcactcaggt    120
tgcattattg ctaatttcta gtataatata atctgttagc acctgataga tgtgagtgct    180
aaaagtgagg gcgatatata                                                 200
```

<210> SEQ ID NO 63
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1339

<400> SEQUENCE: 63

```
tcttcatcta aaggatatcg ttcatttgaa cgggcacttt acagagctga aaatggctta     60
ccggcatatg agggtactca atcaattgaa tataaacagg aagaaattaa ataatttatt    120
aatattattt taatttgttg tggcgagata tattttttcg ttaaaataga attactaact    180
aaaagaaagg acgcttactg                                                 200
```

<210> SEQ ID NO 64
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)

<223> OTHER INFORMATION: Promoter region for ORF 1429-1427

<400> SEQUENCE: 64

```
gtgaagatga atctcacaat tctaaaaaag gtggctttgg tattggatta gctatggctc    60
aagaattaat tcatactttc cacggtaaaa tttcagtaaa tcatagagaa gaaaatatcg   120
tttttagtgt tagtctaaaa attgtcaaat agatgttctt gatagttgta taatttcaat   180
taaagaatcg aggaattatt                                               200
```

<210> SEQ ID NO 65
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1432-1430

<400> SEQUENCE: 65

```
atcgcttaca aatagattat aacgcaataa cttataaatt taaaaacata tgacatgttg    60
tcatatgttt cattaagtaa acgtgatttt tacaatttta aataattttt atagcaagtt   120
ataacttttta taatattcct gttacttca aagaaaaatc aaaaatcatt gctataatgg   180
cgtaaacgaa agaaaggaca                                               200
```

<210> SEQ ID NO 66
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1433

<400> SEQUENCE: 66

```
tatagcaatg attttttgatt tttctttgaa agtaacagga atattataaa agttataact    60
tgctataaaa ttatttttaaa attgtaaaaa tcacgtttac ttaatgaaac atatgacaac   120
atgtcatatg ttttttaaatt tataagttat tgcgttataa tctatttgta agcgattgca   180
ttttttgcaaa aggagaaatt                                              200
```

<210> SEQ ID NO 67
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region to ORF 1446

<400> SEQUENCE: 67

```
caaaaagctg gtgtaattta ttttttcttta tattttccat tatctctgcc tcactaatta    60
aaattaatta tattaattta tgttaaattt ttcaacttta gtgtcatatt atgtatcata   120
tttgtaagat tatttgacac agattaaaat taggactata ttagttaacg atcttaattt   180
tcacaaaagg gggatgacac                                               200
```

<210> SEQ ID NO 68
<211> LENGTH: 200
<212> TYPE: DNA
<213> ORGANISM: Lactobacillus acidophilus
<220> FEATURE:
<221> NAME/KEY: misc_feature

```
<222> LOCATION: (1)..(200)
<223> OTHER INFORMATION: Promoter region for ORF 1683

<400> SEQUENCE: 68
gaagttgata aacctcaatt agtataattg acactatgtc actaatgcgc tattatatta      60
gataatcaat atattgagaa gcgcctatga cgctgccaat acacaaatga aaactgaaca     120
agtttctcaa atggggaatg gcttatgtaa gtaggctgtt ctctattttt ttattttatg     180
aaaggagtgg tatatccgat                                                  200

<210> SEQ ID NO 69
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1910

<400> SEQUENCE: 69
gtgaagcatt acgagcgctt taatatcaag cgattaaggc caatttttata tttttaatca      60 caataaagaa taaaaatgtg gaaaaagttc aaaataatac ttgcaatctg tggataacat     120
gttatactta taaatgtaaa gaattagcac tcaacgcact agagtgctaa tagacttaaa     180
ttgattggga gtgtttatat                                                  200

<210> SEQ ID NO 70
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 400

<400> SEQUENCE: 70
aattcactat ttatgataac gtattcaaaa aatatgtcaa tcgtttgaca cattttttg       60 aatttatttt ttattaatac ttttcttatg gtccaataag gcaagggtag tcaaatataa     120
tatgataaac gtttgacaca ttttcataa tctactagaa ttaatattaa agataacgct     180
tacatggagg cttttttatt                                                  200

<210> SEQ ID NO 71
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 401

<400> SEQUENCE: 71
tattaattct agtagattat gaaaaatgtg tcaaacgttt atcatattat atttgactac      60
ccttgcctta ttggaccata agaaaagtat taataaaaaa taattcaaa aaaatgtgtc     120 aaacgattga catatttttt gaatacgtta tcataaatag tgaattgaga ataaaagcgt     180
ttacatagga ggaaacaaat                                                  200

<210> SEQ ID NO 72
<211> LENGTH: 200
<212> TYPE: DNA
<213> ORGANISM: Lactobacillus acidophilus
<220> FEATURE:
```

<221> NAME/KEY: misc_feature
<222> LOCATION: (1)..(200)
<223> OTHER INFORMATION: Promoter region for ORF 502-507

<400> SEQUENCE: 72

```
aactgttgac aagttgtgaa agcgatatta tcatttaatt gtaaattgaa aacgtttcca      60
aagtgttcaa atagtttttt gctaaataat tattttttg tagcgaaata gaaacgtttc     120
aattaattta aaacaattag atcttagtag gaaacctttt aattttttgtg caaaattgaa    180
acgtttcaaa aggaggaaaa                                                  200
```

<210> SEQ ID NO 73
<211> LENGTH: 201
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1012

<400> SEQUENCE: 73

```
ctgattttga ttccgtcatt tatgtctttc ctttctttgt acatttatta tattcataaa     60
tgtatagaca agtaaagcat aatttaagtt actataaagt aaatattgtg atcgctttca    120
aaaaatatat tgacaacttg tatatacaag tttaatataa tagctaaatc taatgaaaac    180
gctttataca ggagaaaaac a                                               201
```

<210> SEQ ID NO 74
<211> LENGTH: 200
<212> TYPE: DNA
<213> ORGANISM: Lactobacillus acidophilus
<220> FEATURE:
<221> NAME/KEY: misc_feature
<222> LOCATION: (1)..(2)
<223> OTHER INFORMATION: Promoter region for ORF 1013-1014

<400> SEQUENCE: 74

```
ttcattgttt tcattcattg ttttctcct gtataaagcg ttttcattag atttagctat     60
tatattaaac ttgtatatac aagttgtcaa tatatttttt gaaagcgatc acaatattta   120
ctttatagta acttaaatta tgctttactt gtctatacat ttatgaatat aataaatgta   180
caaagaaagg aaagacataa                                                200
```

<210> SEQ ID NO 75
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1442-1437

<400> SEQUENCE: 75

```
gtattctaac atttgctttt attgcttaca atacaccgat tagtaaatta aatatgtcaa    60
aatgtttata aggccaaatg acaataatgc taatgaaaat actatggttt acatacatag  120
aatacgcaat aattaaatat gtaatttatg aaagcgctta aaattgaatg ctatttattt  180
agttattgag gagtgatctt                                                200
```

<210> SEQ ID NO 76
<211> LENGTH: 200
<212> TYPE: DNA
<213> ORGANISM: Lactobacillus acidophilus

```
<220> FEATURE:
<221> NAME/KEY: misc_feature
<222> LOCATION: (1)..(200)
<223> OTHER INFORMATION: Promoter region for ORF 1459-1457

<400> SEQUENCE: 76
ttggtatcgt gatgtgataa agaaaatgg acaaaattta aataattag tttaaaaaag    60 aaaatattct tacagaatgt ttccttttt attatataaa attaaataat ttatttattt   120
gagtaaacca tttaccaaaa acaaataaga gtatatacta ttatctgaaa acgattacag  180
taaaaattga ggtaaaaacg                                              200

<210> SEQ ID NO 77
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1463-1462

<400> SEQUENCE: 77
ataaaaagaa ataaagacaa cggggctggc taagccctta aactgtaaga gctggtcaat   60
gtgattactc ccaagtggaa tatcagaata ctagtgaaga cgacagtaag tgaaacaaag  120
aaaggaaaaa tatatctttc tgatatgtag aaaattcgtc ttcttctaca tatttccatg  180
ttttatatag caggaatatt                                              200

<210> SEQ ID NO 78
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1467-1468

<400> SEQUENCE: 78
acttacttac gtttattata caaaatattt actcaattcc aataaatatt aattttagca   60
aaaacaaatt ttttaagaat cttcgtaata aatatttac tgttttttaga taaatatttt  120 attttattgg ttaattttt atttggtgat ataataaaag cgttttcaaa ataatttat   180 tatagaaatc aggtattagt                                              200

<210> SEQ ID NO 79
<211> LENGTH: 200
<212> TYPE: DNA
<213> ORGANISM: Lactobacillus acidophilus
<220> FEATURE:
<221> NAME/KEY: misc_feature
<222> LOCATION: (1)..(200)
<223> OTHER INFORMATION: Promoter region for ORF 1469

<400> SEQUENCE: 79
tagttattgc tggagctgtg cgcggcgttg gtggtatcga cagctggggt gctgatgttg   60
aaaagcaata tcacattaat cctgaaaaag actacgaatt ttctttcaat cttaattaaa  120
tattttatca ataatagtaa atgttttact gatttatgtg ttataatgta atcgatttca  180
agaaaacaaa ggagtaaaca                                              200

<210> SEQ ID NO 80
<211> LENGTH: 297
<212> TYPE: DNA
```

<213> ORGANISM: Lactobacillus acidophilus
<220> FEATURE:
<221> NAME/KEY: misc_feature
<222> LOCATION: (0)...(0)
<223> OTHER INFORMATION: promoter region for ORFS 1467-1468 including
      repressor sequences

<400> SEQUENCE: 80
gtggcaggtg aataacccga tttttgtgca atctctttaa tagttgtcat agttaatttc  60
ttttcttttt aaaaaactta cttacgttta ttatacaaaa tatttactca attccaataa  120
atattaattt tagcaaaaac aaattttta agaatcttcg taataaatat ttactgtttt  180
ttagataaat atttttatttt attggttaat tttttatttg gtgatataat aaaagcgttt  240
tcaaaaataa tttattatag aaatcaggta ttagtcaagc aaacataaaa tggcttg  297

<210> SEQ ID NO 81
<211> LENGTH: 22
<212> TYPE: DNA
<213> ORGANISM: Artificial
<220> FEATURE:
<223> OTHER INFORMATION: Consensus UP element
<220> FEATURE:
<221> NAME/KEY: misc_feature
<222> LOCATION: (1)..(2)
<223> OTHER INFORMATION: n= a, c, g, or t
<220> FEATURE:
<221> NAME/KEY: misc_feature
<222> LOCATION: (14)..(15)
<223> OTHER INFORMATION: n= a, c, g, or t
<220> FEATURE:
<221> NAME/KEY: misc_feature
<222> LOCATION: (20)..(22)
<223> OTHER INFORMATION: n= a, c, g, or t

<400> SEQUENCE: 81
nnaaawwtwt tttnnaaaan nn                                            22

<210> SEQ ID NO 82
<211> LENGTH: 14
<212> TYPE: DNA
<213> ORGANISM: Artificial
<220> FEATURE:
<223> OTHER INFORMATION: Consensus UP element
<220> FEATURE:
<221> NAME/KEY: misc_feature
<222> LOCATION: (1)..(2)
<223> OTHER INFORMATION: n= a, c, g, or t
<220> FEATURE:
<221> NAME/KEY: misc_feature
<222> LOCATION: (14)..(14)
<223> OTHER INFORMATION: n= a, c, g, or t

<400> SEQUENCE: 82
nnawwwwwtt tttn                                                     14

<210> SEQ ID NO 83
<211> LENGTH: 9
<212> TYPE: DNA
<213> ORGANISM: Artificial
<220> FEATURE:
<223> OTHER INFORMATION: Consensus UP element
<220> FEATURE:
<221> NAME/KEY: misc_feature
<222> LOCATION: (8)..(8)
<223> OTHER INFORMATION: n= a, c, g, or t

<400> SEQUENCE: 83 aaaaaarnr                                                            9

<210> SEQ ID NO 84
<211> LENGTH: 22
<212> TYPE: DNA
<213> ORGANISM: Artificial
<220> FEATURE:
<223> OTHER INFORMATION: Consensus UP element
<220> FEATURE:
<221> NAME/KEY: misc_feature
<222> LOCATION: (1)..(2)
<223> OTHER INFORMATION: n= a, c, g, or t
<220> FEATURE:
<221> NAME/KEY: misc_feature
<222> LOCATION: (14)..(16)
<223> OTHER INFORMATION: n= a, c, g, or t
<220> FEATURE:
<221> NAME/KEY: misc_feature
<222> LOCATION: (20)..(22)
<223> OTHER INFORMATION: n= a, c, g, or t

<400> SEQUENCE: 84
nnaaawwtwt tttnnnaaan nn                                    22

<210> SEQ ID NO 85
<211> LENGTH: 18
<212> TYPE: DNA
<213> ORGANISM: Artificial
<220> FEATURE:
<223> OTHER INFORMATION: Consensus UP element
<220> FEATURE:
<221> NAME/KEY: misc_feature
<222> LOCATION: (13)..(15)
<223> OTHER INFORMATION: n= a, c, g, or t

<400> SEQUENCE: 85
aaawwwtwtt ttnnnaaa                                         18

<210> SEQ ID NO 86
<211> LENGTH: 52
<212> TYPE: DNA
<213> ORGANISM: Artificial
<220> FEATURE:
<223> OTHER INFORMATION: Consensus UP element
<220> FEATURE:
<221> NAME/KEY: misc_feature
<222> LOCATION: (2)..(2)
<223> OTHER INFORMATION: n= a, c, g, or t
<220> FEATURE:
<221> NAME/KEY: misc_feature
<222> LOCATION: (11)..(11)
<223> OTHER INFORMATION: n= a, c, g, or t
<220> FEATURE:
<221> NAME/KEY: misc_feature
<222> LOCATION: (14)..(14)
<223> OTHER INFORMATION: n= a, c, g, or t
<220> FEATURE:
<221> NAME/KEY: misc_feature
<222> LOCATION: (22)..(22)
<223> OTHER INFORMATION: n= a, c, g, or t
<220> FEATURE:
<221> NAME/KEY: misc_feature
<222> LOCATION: (29)..(46)
<223> OTHER INFORMATION: n= a, c, g, or t

<400> SEQUENCE: 86
gnaaaaatwt nttnaaaaaa mncttgmann nnnnnnnnnn nnnnnntata at   52

<210> SEQ ID NO 87
<211> LENGTH: 14
<212> TYPE: DNA
<213> ORGANISM: Artificial
<220> FEATURE:
<223> OTHER INFORMATION: Consensus cre sequence

```
<220> FEATURE:
<221> NAME/KEY: misc_feature
<222> LOCATION: (6)..(6)
<223> OTHER INFORMATION: n= a, c, g, or t
<220> FEATURE:
<221> NAME/KEY: misc_feature
<222> LOCATION: (9)..(9)
<223> OTHER INFORMATION: n= a, c, g, or t
<220> FEATURE:
<221> NAME/KEY: misc_feature
<222> LOCATION: (11)..(11)
<223> OTHER INFORMATION: n= a, c, g, or t

<400> SEQUENCE: 87
tgwaancgnt nwca                                                            14

<210> SEQ ID NO 88
<211> LENGTH: 21
<212> TYPE: DNA
<213> ORGANISM: Artificial
<220> FEATURE:
<223> OTHER INFORMATION: Consensus cre sequence
<220> FEATURE:
<221> NAME/KEY: misc_feature
<222> LOCATION: (16)..(16)
<223> OTHER INFORMATION: n= a, c, g, or t

<400> SEQUENCE: 88
wwwwtgwaar cgytwncwww w                                                    21

<210> SEQ ID NO 89
<211> LENGTH: 18
<212> TYPE: DNA
<213> ORGANISM: Artificial
<220> FEATURE:
<223> OTHER INFORMATION: Consensus cre sequence
<220> FEATURE:
<221> NAME/KEY: misc_feature
<222> LOCATION: (5)..(5)
<223> OTHER INFORMATION: n= a, c, g, or t
<220> FEATURE:
<221> NAME/KEY: misc_feature
<222> LOCATION: (11)..(11)
<223> OTHER INFORMATION: n= a, c, g, or t

<400> SEQUENCE: 89
wwtgnaarcg nwwwcaww                                                        18

<210> SEQ ID NO 90
<211> LENGTH: 16
<212> TYPE: DNA
<213> ORGANISM: Artificial Sequence
<220> FEATURE:
<223> OTHER INFORMATION: Cre promoter element

<400> SEQUENCE: 90
tgataaacgt ttgaca                                                          16

<210> SEQ ID NO 91
<211> LENGTH: 14
<212> TYPE: DNA
<213> ORGANISM: Artificial sequence
<220> FEATURE:
<223> OTHER INFORMATION: Cre promoter element

<400> SEQUENCE: 91
agataacgct taca                                                            14

<210> SEQ ID NO 92
```

```
<211> LENGTH: 14
<212> TYPE: DNA
<213> ORGANISM: Artificial Sequence
<220> FEATURE:
<223> OTHER INFORMATION: Cre promoter element

<400> SEQUENCE: 92
tgaatacgtt atca                                                    14

<210> SEQ ID NO 93
<211> LENGTH: 14
<212> TYPE: DNA
<213> ORGANISM: Artificial Sequence
<220> FEATURE:
<223> OTHER INFORMATION: Cre promoter element

<400> SEQUENCE: 93
taaaagcgtt taca                                                    14

<210> SEQ ID NO 94
<211> LENGTH: 14
<212> TYPE: DNA
<213> ORGANISM: Artificial Sequence
<220> FEATURE:
<223> OTHER INFORMATION: Cre promoter element

<400> SEQUENCE: 94
taaaagcgga ttca                                                    14

<210> SEQ ID NO 95
<211> LENGTH: 14
<212> TYPE: DNA
<213> ORGANISM: Artificial Sequence
<220> FEATURE:
<223> OTHER INFORMATION: Cre promoter element

<400> SEQUENCE: 95
tgaaagcgat atta                                                    14

<210> SEQ ID NO 96
<211> LENGTH: 14
<212> TYPE: DNA
<213> ORGANISM: Artificial Sequence
<220> FEATURE:
<223> OTHER INFORMATION: Cre promoter element

<400> SEQUENCE: 96
tgaaaacgtt tcca                                                    14

<210> SEQ ID NO 97
<211> LENGTH: 14
<212> TYPE: DNA
<213> ORGANISM: Artificial sequence
<220> FEATURE:
<223> OTHER INFORMATION: Cre promoter element

<400> SEQUENCE: 97
tagaaacgtt tcaa                                                    14

<210> SEQ ID NO 98
<211> LENGTH: 14
<212> TYPE: DNA
<213> ORGANISM: Artificial Sequence
<220> FEATURE:
<223> OTHER INFORMATION: Cre promoter element

<400> SEQUENCE: 98
```

-continued ttcaaacgtt tcaa                                                     14

<210> SEQ ID NO 99
<211> LENGTH: 14
<212> TYPE: DNA
<213> ORGANISM: Artificial Sequence
<220> FEATURE:
<223> OTHER INFORMATION: Cre promoter element

<400> SEQUENCE: 99
tgtgatcgct ttca                                                     14

<210> SEQ ID NO 100
<211> LENGTH: 14
<212> TYPE: DNA
<213> ORGANISM: Artificial Sequence
<220> FEATURE:
<223> OTHER INFORMATION: Cre promoter element

<400> SEQUENCE: 100
tgaaaacgct ttat                                                     14

<210> SEQ ID NO 101
<211> LENGTH: 14
<212> TYPE: DNA
<213> ORGANISM: Artificial sequence
<220> FEATURE:
<223> OTHER INFORMATION: Cre promoter element

<400> SEQUENCE: 101
ataaagcgtt ttca                                                     14

<210> SEQ ID NO 102
<211> LENGTH: 14
<212> TYPE: DNA
<213> ORGANISM: Artificial Sequence
<220> FEATURE:
<223> OTHER INFORMATION: Cre promoter element

<400> SEQUENCE: 102
tgaaagcgat caca                                                     14

<210> SEQ ID NO 103
<211> LENGTH: 14
<212> TYPE: DNA
<213> ORGANISM: Artificial Sequence
<220> FEATURE:
<223> OTHER INFORMATION: Cre promoter element

<400> SEQUENCE: 103
agaatacgca ataa                                                     14

<210> SEQ ID NO 104
<211> LENGTH: 14
<212> TYPE: DNA
<213> ORGANISM: Artificial Sequence
<220> FEATURE:
<223> OTHER INFORMATION: Cre promoter element

<400> SEQUENCE: 104
tgaaagcgct taaa                                                     14

<210> SEQ ID NO 105
<211> LENGTH: 14
<212> TYPE: DNA

<213> ORGANISM: Artificial Sequence
<220> FEATURE:
<223> OTHER INFORMATION: Cre promoter element

<400> SEQUENCE: 105
tgaaaagcat taca                                                         14

<210> SEQ ID NO 106
<211> LENGTH: 14
<212> TYPE: DNA
<213> ORGANISM: Artificial Sequence
<220> FEATURE:
<223> OTHER INFORMATION: Cre promoter element

<400> SEQUENCE: 106
aaaattcgtc ttct                                                         14

<210> SEQ ID NO 107
<211> LENGTH: 14
<212> TYPE: DNA
<213> ORGANISM: Artificial Sequence
<220> FEATURE:
<223> OTHER INFORMATION: Cre promoter element

<400> SEQUENCE: 107
taaaagcgtt ttca                                                         14

<210> SEQ ID NO 108
<211> LENGTH: 14
<212> TYPE: DNA
<213> ORGANISM: Artificial Sequence
<220> FEATURE:
<223> OTHER INFORMATION: Cre promoter element

<400> SEQUENCE: 108
tgtaatcgat ttca                                                         14

<210> SEQ ID NO 109
<211> LENGTH: 6
<212> TYPE: DNA
<213> ORGANISM: Artificial Sequence
<220> FEATURE:
<223> OTHER INFORMATION: Hexamer found at position -10 of promoter
      sequences

<400> SEQUENCE: 109 tataat                                                                   6

<210> SEQ ID NO 110
<211> LENGTH: 6
<212> TYPE: DNA
<213> ORGANISM: Artificial Sequence
<220> FEATURE:
<223> OTHER INFORMATION: Hexamer found at position -35 of promoter
      sequences

<400> SEQUENCE: 110 ttgaca                                                                   6

<210> SEQ ID NO 111
<211> LENGTH: 9
<212> TYPE: DNA
<213> ORGANISM: Artificial Sequence
<220> FEATURE:
<223> OTHER INFORMATION: Hexamer found at position -35 of promoter
      sequences

```
<400> SEQUENCE: 111 tcttgacat                                                                9
```